(12) United States Patent
Poree et al.

(10) Patent No.: US 9,078,446 B2
(45) Date of Patent: *Jul. 14, 2015

(54) USE OF N-(TETRAZOL-4-YL)- OR N-(TRIAZOL-3-YL)ARYLCARBOXAMIDES OR THEIR SALTS FOR CONTROLLING UNWANTED PLANTS IN AREAS OF TRANSGENIC CROP PLANTS BEING TOLERANT TO HPPD INHIBITOR HERBICIDES

(75) Inventors: Fabien Poree, Frankfurt (DE); Andreas Almsick, Karben (DE); Ralf Braun, Ramberg (DE); Bernd Laber, Idstein (DE); Ruediger Hain, Frankfurt (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/006,049

(22) PCT Filed: Mar. 21, 2012

(86) PCT No.: PCT/EP2012/054981
§ 371 (c)(1),
(2), (4) Date: Oct. 8, 2013

(87) PCT Pub. No.: WO2012/130685
PCT Pub. Date: Oct. 4, 2012

(65) Prior Publication Data
US 2014/0024530 A1    Jan. 23, 2014

Related U.S. Application Data

(60) Provisional application No. 61/467,619, filed on Mar. 25, 2011.

(30) Foreign Application Priority Data

Mar. 25, 2011    (EP) .................................... 11159755

(51) Int. Cl.
| | | |
|---|---|---|
| A01P 13/00 | (2006.01) | |
| A01N 43/653 | (2006.01) | |
| A01N 43/713 | (2006.01) | |
| C07D 249/14 | (2006.01) | |
| A01N 57/24 | (2006.01) | |
| A01N 43/80 | (2006.01) | |
| A01N 47/28 | (2006.01) | |
| A01N 47/34 | (2006.01) | |

(52) U.S. Cl.
CPC .............. *A01N 57/24* (2013.01); *A01N 43/653* (2013.01); *A01N 43/713* (2013.01); *A01N 43/80* (2013.01); *A01N 47/28* (2013.01); *A01N 47/34* (2013.01)

(58) Field of Classification Search
CPC . A01N 43/653; A01N 43/713; C07D 401/02; C07D 249/14; C07D 257/06

USPC ............. 514/340; 546/272.4, 268.4; 548/251, 548/264.8

See application file for complete search history.

(56) References Cited

U.S. PATENT DOCUMENTS

| | | | |
|---|---|---|---|
| 4,474,792 A * | 10/1984 | Erickson ........................ | 514/381 |
| 6,268,549 B1 | 7/2001 | Sailland et al. | |
| 6,812,010 B1 | 11/2004 | Derose et al. | |
| 8,481,749 B2 | 7/2013 | Braun et al. | |
| 8,822,378 B2 * | 9/2014 | Braun et al. ................... | 504/105 |
| 2005/0257283 A1 | 11/2005 | Matringe et al. | |
| 2011/0039706 A1 | 2/2011 | Busch et al. | |
| 2011/0191897 A1 | 8/2011 | Poree et al. | |
| 2011/0197307 A1 | 8/2011 | Poree et al. | |
| 2011/0197308 A1 | 8/2011 | Poree et al. | |
| 2011/0197309 A1 | 8/2011 | Poree et al. | |

(Continued)

FOREIGN PATENT DOCUMENTS

| | | |
|---|---|---|
| EP | 0496630 | 7/1992 |
| WO | 96/38567 | 12/1996 |
| WO | 99/24585 | 5/1999 |

(Continued)

OTHER PUBLICATIONS

Matyk; II Farmaco, 2005, 60, 399-408.*
STN result for registry No. 639048-78-5, entered STN Jan. 19, 2004.*

(Continued)

*Primary Examiner* — John Mabry
*Assistant Examiner* — Daniel Carcanague
(74) *Attorney, Agent, or Firm* — Miles and Stockbridge

(57) ABSTRACT

Use of N-(tetrazol-4-yl)- or N-(triazol-3-yl)arylcarboxamides of formula (I) or salts thereof

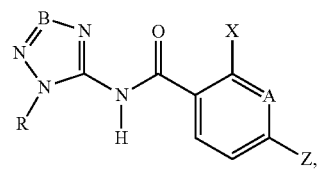

(I)

for controlling unwanted plants in areas of transgenic crop plants being tolerant to HPPD inhibitor herbicides by containing one or more chimeric gene(s) comprising (I) a DNA sequence encoding hydroxyphenylpyruvate dioxygenase (HPPD) derived from a member of a group of organisms consisting of (a) *Avena*, (b) *Pseudomonas*, (c) *Synechococcoideae*, (d) *Blepharismidae*, (e) *Rhodococcus*, (f) Picrophilaceae, (g) Kordia, or (II) comprising one or more mutated DNA sequences of HPPD encoding genes of the before defined organisms.

11 Claims, No Drawings

(56) References Cited

U.S. PATENT DOCUMENTS

| | | |
|---|---|---|
| 2011/0197310 A1 | 8/2011 | Poree et al. |
| 2012/0058892 A1 | 3/2012 | Braun et al. |

FOREIGN PATENT DOCUMENTS

| | | |
|---|---|---|
| WO | 02/46387 | 6/2002 |
| WO | 2004/024928 | 3/2004 |
| WO | 2008/150473 | 12/2008 |
| WO | 2009/144079 | 12/2009 |
| WO | 2010/085705 | 7/2010 |
| WO | 2011/076877 | 6/2011 |
| WO | 2011/076882 | 6/2011 |
| WO | 2011/076885 | 6/2011 |
| WO | 2011/076889 | 6/2011 |
| WO | 2011/076892 | 6/2011 |
| WO | 2012/028579 | 3/2012 |

OTHER PUBLICATIONS

International Search Report From PCT/EP2012/054981 Mailed May 3, 2012.

* cited by examiner

USE OF N-(TETRAZOL-4-YL)- OR N-(TRIAZOL-3-YL)ARYLCARBOXAMIDES OR THEIR SALTS FOR CONTROLLING UNWANTED PLANTS IN AREAS OF TRANSGENIC CROP PLANTS BEING TOLERANT TO HPPD INHIBITOR HERBICIDES

CROSS REFERENCE TO RELATED APPLICATIONS

This application is a §371 National Stage Application of PCT/EP2012/054981, filed Mar. 21, 2012, which claims priority to European Application No. 11159755.5, filed Mar. 25, 2011, and U.S. Provisional Application No. 61/467,619, filed Mar. 25, 2011.

BACKGROUND OF THE INVENTION

1. Field of the Invention

The invention relates to the use of N-(tetrazol-4-yl)- or N-(triazol-3-yl)arylcarboxamides or their for controlling unwanted plants in areas of transgenic crop plants being tolerant to HPPD inhibitor herbicides.

2. Description of Related Art

EP 10174893 (being filed in the name of Bayer CropScience AG at the EPO on Sep. 1, 2010) and its corresponding international application PCT/EP2011/064820 disclose several new N-(tetrazol-4-yl)- or N-(triazol-3-yl)arylcarboxamides and their use as HPPD inhibitor herbicides for weed control.

However, the herbicidal activity of N-(tetrazol-4-yl)- or N-(triazol-3-yl)arylcarboxamides might cause damages on several crop plants which limit their use in such crop growing areas as herbicides for weed control.

HPPD inhibitor herbicides can be used against grass and/or broad leaf weeds in crop plants that display metabolic tolerance, such as maize (Zea mays) in which they are rapidly degraded (Schulz et al., (1993). FEBS letters, 318, 162-166; Mitchell et al., (2001) Pest Management Science, Vol 57, 120-128; Garcia et al., (2000) Biochem., 39, 7501-7507; Pallett et al., (2001) Pest Management Science, Vol 57, 133-142). In order to extend the scope of these HPPD inhibitor herbicides, several efforts have been developed in order to confer to plants, particularly plants without or with an under-performing metabolic tolerance, a tolerance level acceptable under agronomic field conditions.

Meanwhile transgeninc plants have been engineered by by-passing HPPD-mediated production of homogentisate (U.S. Pat. No. 6,812,010), overexpressing the sensitive enzyme so as to produce quantities of the target enzyme in the plant which are sufficient in relation to the herbicide has been performed (WO96/38567).

Alternatively, transgenic plants have been generated expressing HPPD proteins that have been mutated at various positions in order to obtain a target enzyme which, while retaining its properties of catalysing the transformation of HPP into homogentisate, is less sensitive to HPPD inhibitor herbicides than is the native HPPD before mutation (for example see at EP496630, WO 99/24585).

More recently, the introduction of a Pseudomonas HPPD gene into the plastid genome of tobacco and soybean has shown to be more effective than nuclear transformation, conferring even tolerance to post-emergence application of at least one HPPD inhibitor (Dufourmantel et al., 2007, Plant Biotechnol J. 5(1):118-33).

In WO 2009/144079, a nucleic acid sequence encoding a mutated hydroxyphenylpyruvate dioxygenase (HPPD) at position 336 of the Pseudomonas fluorescens HPPD protein and its use for obtaining plants which are tolerant to HPPD inhibitor herbicides is disclosed.

In WO 04/024928, the inventors have sought to increase the prenylquinone biosynthesis (e.g., synthesis of plastoquinones, tocopherols) in the cells of plants by increasing the flux of the HPP precursor into the cells of these plants. This has been done by connecting the synthesis of said precursor to the "shikimate" pathway by overexpression of the prephenate-dehydrogenase (PDH). They have also noted that the transformation of plants with a gene encoding a PDH enzyme makes it possible to increase the tolerance of said plants to HPPD inhibitors.

In WO 2002/046387, an gene obtained from Avena sativa encoding an HPPD was described to generate plants overexpressing such gene and thereby causing tolerance to various HPPD-inhibitor herbicides.

In WO 2008/150473, the combination of two distinct tolerance mechanisms—a modified Avena sativa gene coding for a mutant HPPD enzyme and a CYP450 Maize monooxygenase (nsf1 gene)—was exemplified in order to obtain an improved tolerance to HPPD inhibitor herbicides, but no data have been disclosed demonstrating the synergistic effects based on the combination of both proteins.

In WO 2010/085705, several mutants of the Avena sativa HPPD were described as well as plants comprising genes encoding such mutated HPPD and thereby causing an increased tolerance to various HPPD-inhibitor herbicides compared to non-mutated HPPD.

Recently, several new genes encoding HPPD enzymes from various organisms have been identified and employed for obtaining crop plants that show an agronomically useful level of tolerance concerning the application of various HPPD inhibitor herbicides.

The work concerning the implementation of such tolerance against HPPD inhibitor herbicides have extensively been described in the PCT-applications being filed in the name of Bayer CropScience AG on Dec. 22, 2010, having the filing numbers (PCT/EP2010/070561 (published as WO 2011/076877; relates to nucleic acid sequences encoding a hydroxyphenylpyruvate dioxygenase (HPPD) obtained from bacteria belonging to the subfamily Synechococcoideae and certain mutants thereof); PCT/EP2010/070567 (published as WO 2011/076882; encoding a hydroxyphenylpyruvate dioxygenase obtained from protists belonging to the family Blepharismidae); PCT/EP2010/070578 (published as WO 2011/076892; encoding a hydroxyphenylpyruvate dioxygenase obtained from bacteria belonging to the genus Rhodococcus and certain mutants thereof); PCT/EP2010/070570 (published as WO 2011/076885; encoding a hydroxyphenylpyruvate dioxygenase obtained from Euryarchaeota belonging to the family Picrophilaceae and certain mutants thereof); PCT/EP2010/070575 (published as WO 2011/076889; encoding a hydroxyphenylpyruvate dioxygenase obtained from bacteria belonging to the genus Kordia and certain mutants thereof) and which are hereby incorporated by reference concerning the production of the respective transgenic plants conferring tolerance to HPPD inhibitor heribicides.

SUMMARY

It has now been found that N-(tetrazol-4-yl)- or N-(triazol-3-yl)arylcarboxamides can be employed on transgenic crop plants being tolerant to HPPD inhibitor herbicides by containing one or more genes conferring tolerance to HPPD inhibitor herbicides.

Subject matter of the present invention is the use of N-(tetrazol-4-yl)- or N-(triazol-3-yl)arylcarboxamides of the formula (I) or their salts

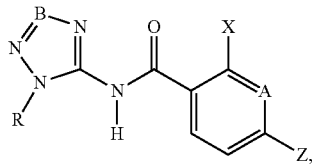

in which
A is N or CY,
B is N or CH,
X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1$, $R_2$, $P(O)(OR^5)_2$, $CH_2P(O)(OR^5)_2$, $(C_1-C_6)$-alkyl-heteroaryl, $(C_1-C_6)$-alkyl-heterocyclyl, the two last-mentioned radicals being substituted in each case by s halogen, $(C_1-C_6)$-alkyl, halo-$(C_1-C_6)$-alkyl, $S(O)_n$—$(C_1-C_6)$-alkyl, $(C_1-C_6)$-alkoxy and/or halo-$(C_1-C_6)$-alkoxy radicals, and where heterocyclyl carries 0 to 2 oxo groups,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, the last 6 radicals being substituted in each case by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries 0 to 2 oxo groups,
Z is halogen, cyano, thiocyanato, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, heteroaryl, heterocyclyl or phenyl, the last three radicals being substituted in each case by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy or halo-$(C_1-C_6)$-alkoxy, and where heterocyclyl carries 0 to 2 oxo groups, or
Z may else be hydrogen, $(C_1-C_6)$-alkyl or $(C_1-C_6)$-alkoxy if Y is the radical $S(O)_nR^2$,
R is $(C_1-C_6)$-alkyl, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $CH_2R^6$, heteroaryl, heterocyclyl or phenyl, the last three radicals being substituted in each case by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl,
$R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, the 21 last-mentioned radicals being substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries 0 to 2 oxo groups,
$R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, the 21 last-mentioned radicals being substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries 0 to 2 oxo groups,
$R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl,
$R^4$ is $(C_1-C_6)$-alkyl, $(C_2-C_6)$-alkenyl or $(C_2-C_6)$-alkynyl,
$R^5$ is methyl or ethyl,
$R^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy or $(C_3-C_6)$-cycloalkyl or is heteroaryl, heterocyclyl or phenyl substituted in each case by s radicals from the group consisting of methyl, ethyl, methoxy, trifluoromethyl, and halogen,
n is 0, 1 or 2,
s is 0, 1, 2 or 3, for controlling unwanted plants in areas of transgenic crop plants being tolerant to HPPD inhibitor herbicides by containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

DETAILED DESCRIPTION OF A PREFERRED EMBODIMENT

In formula (I) and all the formulae below, alkyl radicals having more than two carbon atoms can be straight-chain or branched. Alkyl radicals are, for example, methyl, ethyl, n- or isopropyl, n-, iso-, t- or 2-butyl, pentyls, hexyls, such as n-hexyl, isohexyl and 1,3-dimethylbutyl. Halogen is fluorine, chlorine, bromine or iodine.

Heterocyclyl is a saturated, partially saturated or fully unsaturated cyclic radical which contains from 3 to 6 ring atoms, of which 1 to 4 are from the group consisting of oxygen, nitrogen and sulfur, and which radical can additionally be fused by a benzo ring. For example, heterocyclyl is piperidinyl, pyrrolidinyl, tetrahydrofuranyl, dihydrofuranyl, 4,5-dihydro-1,2-oxazol-3-yl and oxetanyl.

Heteroaryl is an aromatic cyclic radical which contains 3 to 6 ring atoms, of which 1 to 4 are from the group consisting of oxygen, nitrogen and sulfur, and which radical can additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

Where a group is substituted by a plurality of radicals, this means that this group is substituted by one or more identical or different representatives of the radicals mentioned.

Depending on the nature and the attachment of the substituents, the compounds of the formula (I) may be present as stereoisomers. If, for example, one or more asymmetric carbon atoms are present, there may be enantiomers and diastereomers. There may also be stereoisomers if n is 1 (sulfoxides). Stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. The invention also relates to all stereoisomers and mixtures thereof embraced by the general formula (I) but not specifically defined.

Preference is given to the inventive use of N-(tetrazol-4-yl)- or N-(triazol-3-yl)arylcarboxamide of general formula (I), in which A is N or CY, B is N or CH, X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_1-C_6)$-alkyl-O—$(C_1-C_6)$-alkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$ or $(C_1-C_6)$-alkyl-$NR^1SO_2R^2$, $(C_1-C_6)$-alkyl-heteroaryl, $(C_1-C_6)$-alkyl-heterocyclyl, the two last-mentioned radicals being substituted in each case by s halogen, $(C_1-C_6)$-alkyl, halo-$(C_1-C_6)$-alkyl, $S(O)_n$—$(C_1-C_6)$-alkyl, $(C_1-C_6)$-alkoxy and/or halo-$(C_1-C_6)$-alkoxy radicals, and where heterocyclyl carries 0 to 2 oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $COOR^1$, $OSO_2R^2$, $S(O)_nR^2$, $SO_2OR^1$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, the last 6 radicals being substituted in each case by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries 0 to 2 oxo groups, Z is halogen, cyano, thiocyanato, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $C(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, ($C_1$-$C_6$)-alkyl-CON($R^1$)$_2$, ($C_1$-$C_6$)-alkyl-SO$_2$N($R^1$)$_2$, ($C_1$-$C_6$)-alkyl-NR$^1$COR$^1$, ($C_1$-$C_6$)-alkyl-NR$^1$SO$_2$R$^2$ or 1,2,4-triazol-1-yl, or Z may else be hydrogen, ($C_1$-$C_6$)-alkyl or ($C_1$-$C_6$)-alkoxy if Y is the radical S(O)$_n$R$^2$, R is ($C_1$-$C_6$)-alkyl, ($C_3$-$C_7$)-cycloalkyl, halo-($C_1$-$C_6$)-alkyl, ($C_3$-$C_7$)-cycloalkylmethyl, methoxycarbonylmethyl, ethoxycarbonylmethyl, acetylmethyl, methoxymethyl, or phenyl or benzyl each substituted by s radicals from the group consisting of methyl, methoxy, trifluoromethyl and halogen, R$^1$ is hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl or ($C_1$-$C_6$)-alkyl-NR$^3$-heterocyclyl, the 16 last-mentioned radicals being substituted by radicals from the group consisting of cyano, halogen, nitro, OR$^3$, S(O)$_n$R$^4$, N(R$^3$)$_2$, NR$^3$OR$^3$, COR$^3$, OCOR$^3$, NR$^3$COR$^3$, NR$^3$SO$_2$R$^4$, CO$_2$R$^3$, CON(R$^3$)$_2$ and ($C_1$-$C_4$)-alkoxy-($C_2$-$C_6$)-alkoxycarbonyl, and where heterocyclyl carries 0 to 2 oxo groups, R$^2$ is ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl or ($C_1$-$C_6$)-alkyl-NR$^3$-heterocyclyl, these radicals being substituted by s radicals from the group consisting of cyano, halogen, nitro, OR$^3$, S(O)$_n$R$^4$, N(R$^3$)$_2$, NR$^3$OR$^3$, NR$^3$SO$_2$R$^4$, COR$^3$, OCOR$^3$, NR$^3$COR$^3$, CO$_2$R$^3$, CON(R$^3$)$_2$ and ($C_1$-$C_4$)-alkoxy-($C_2$-$C_6$)-alkoxycarbonyl, and where heterocyclyl carries 0 to 2 oxo groups, R$^3$ is hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, R$^4$ is ($C_1$-$C_6$)-alkyl, ($C_2$-$C_6$)-alkenyl or ($C_2$-$C_6$)-alkynyl, n is 0, 1 or 2, s is 0, 1, 2 or 3, for controlling unwanted plants in areas of transgenic crop plants being tolerant to HPPD inhibitor herbicides by containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

Particular preference is given to the inventive use of N-(tetrazol-4-yl)- or N-(triazol-3-yl)arylcarboxamide of general formula (I), in which A is N or CY, B is N or CH, X is nitro, halogen, cyano, ($C_1$-$C_6$)-alkyl, halo-($C_1$-$C_6$)-alkyl, ($C_3$-$C_6$)-cycloalkyl, OR$^1$, S(O)$_n$R$^2$, ($C_1$-$C_6$)-alkyl-S(O)$_n$R$^2$, ($C_1$-$C_6$)-alkyl-OR$^1$, ($C_1$-$C_6$)-alkyl-CON(R$^1$)$_2$, ($C_1$-$C_6$)-alkyl-SO$_2$N(R$^1$)$_2$, ($C_1$-$C_6$)-alkyl-NR$^1$COR$^1$, ($C_1$-$C_6$)-alkyl-NR$^1$SO$_2$R$^2$, ($C_1$-$C_6$)-alkyl-heteroaryl or ($C_1$-$C_6$)-alkyl-heterocyclyl, the two last-mentioned radicals being substituted in each case by s halogen, ($C_1$-$C_6$)-alkyl, halo-($C_1$-$C_6$)-alkyl, S(O)$_n$—($C_1$-$C_6$)-alkyl, ($C_1$-$C_6$)-alkoxy and/or halo-($C_1$-$C_6$)-alkoxy radicals, and where heterocyclyl carries 0 to 2 oxo groups, Y is hydrogen, nitro, halogen, cyano, ($C_1$-$C_6$)-alkyl, ($C_1$-$C_6$)-haloalkyl, OR$^1$, S(O)$_n$R$^2$, SO$_2$N(R$^1$)$_2$, N(R$^1$)$_2$, NR$^1$SO$_2$R$^2$, NR$^1$COR$^1$, ($C_1$-$C_6$)-alkyl-S(O)$_n$R$^2$, ($C_1$-$C_6$)-alkyl-OR$^1$, ($C_1$-$C_6$)-alkyl-CON(R$^1$)$_2$, ($C_1$-$C_6$)-alkyl-SO$_2$N(R$^1$)$_2$, ($C_1$-$C_6$)-alkyl-NR$^1$COR$^1$, ($C_1$-$C_6$)-alkyl-NR$^1$SO$_2$R$^2$, ($C_1$-$C_6$)-alkyl-phenyl, ($C_1$-$C_6$)-alkyl-heteroaryl, ($C_1$-$C_6$)-alkyl-heterocyclyl, phenyl, heteroaryl or heterocyclyl, the last 6 radicals being substituted in each case by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl, and cyanomethyl, and where heterocyclyl carries 0 to 2 oxo groups, Z is halogen, cyano, halo-($C_1$-$C_6$)-alkyl, ($C_3$-$C_6$)-cycloalkyl, S(O)$_n$R$^2$ or 1,2,4-triazol-1-yl, or Z may else be hydrogen, methyl, methoxy or ethoxy if Y is the radical S(O)$_n$R$^2$, R is ($C_1$-$C_6$)-alkyl, ($C_3$-$C_7$)-cycloalkyl, halo-($C_1$-$C_6$)-alkyl, ($C_3$-$C_7$)-cycloalkylmethyl, methoxycarbonylmethyl, ethoxycarbonylmethyl, acetylmethyl or methoxymethyl, or is phenyl substituted by s radicals from the group consisting of methyl, methoxy, trifluoromethyl, and halogen;

R$^1$ is hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl or ($C_1$-$C_6$)-alkyl-NR$^3$-heterocyclyl, the 16 last-mentioned radicals being substituted by radicals from the group consisting of cyano, halogen, nitro, OR$^3$, S(O)$_n$R$^4$, N(R$^3$)$_2$, NR$^3$OR$^3$, COR$^S$, OCOR$^3$, NR$^3$COR$^3$, NR$^3$SO$_2$R$^4$, CO$_2$R$^3$, CON(R$^3$)$_2$, and ($C_1$-$C_4$)-alkoxy-($C_2$-$C_6$)-alkoxycarbonyl, and where heterocyclyl carries 0 to 2 oxo groups, R$^2$ is ($C_1$-$C_6$)-alkyl, ($C_3$-$C_6$)-cycloalkyl or ($C_3$-$C_6$)-cycloalkyl-($C_1$-$C_6$)-alkyl, these three aforementioned radicals being substituted in each case by s radicals from the group consisting of halogen and OR$^3$, R$^3$ is hydrogen or ($C_1$-$C_6$)-alkyl, R$^4$ is ($C_1$-$C_6$)-alkyl, n is 0, 1 or 2, s is 0, 1, 2 or 3, for controlling unwanted plants in areas of transgenic crop plants being tolerant to HPPD inhibitor herbicides by containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

In all of the formulae below, the substituents and symbols have the same definition as described under formula (I), unless otherwise defined.

Compounds to be used according to the invention can be prepared as described in detail in European patent application "EP 10174893" (being filed in the name of Bayer CropScience AG at the EPO on Sep. 1, 2010) and its corresponding international application PCT/EP2011/064820 which are hereby incorporated by reference.

The compounds listed in the tables hereinbelow are very specially preferred to be used for controlling unwanted plants in areas of transgenic plants containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7 (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

The abbreviations used are:
Et=ethyl Me=methyl n-Pr=n-propyl i-Pr=isopropyl c-Pr=cyclopropyl Ph=phenyl Ac=acetyl Bz=benzoyl

TABLE 1

Compounds of the general formula (I) according to the invention in which A is CY, B is CH and R is methyl

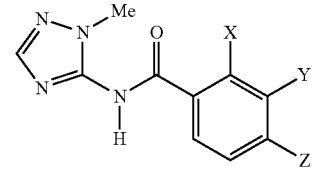

| No. | X | Y | Z |
|---|---|---|---|
| 1-1 | F | H | Cl |
| 1-2 | F | H | Br |
| 1-3 | F | H | SO$_2$Me |
| 1-4 | F | H | SO$_2$Et |
| 1-5 | F | H | CF$_3$ |
| 1-6 | F | H | NO$_2$ |
| 1-7 | Cl | H | F |
| 1-8 | Cl | H | Cl |
| 1-9 | Cl | H | Br |
| 1-10 | Cl | H | SMe |
| 1-11 | Cl | H | SOMe |
| 1-12 | Cl | H | SO$_2$Me |
| 1-13 | Cl | H | SO$_2$CH$_2$Cl |
| 1-14 | Cl | H | SEt |
| 1-15 | Cl | H | SO$_2$Et |
| 1-16 | Cl | H | CF$_3$ |
| 1-17 | Cl | H | NO$_2$ |
| 1-18 | Cl | H | pyrazol-1-yl |
| 1-19 | Cl | H | 1H-1,2,4-triazol-1-yl |
| 1-20 | Br | H | Cl |
| 1-21 | Br | H | Br |
| 1-22 | Br | H | SO$_2$Me |
| 1-23 | Br | H | SO$_2$Et |
| 1-24 | Br | H | CF$_3$ |
| 1-25 | SO$_2$Me | H | Cl |
| 1-26 | SO$_2$Me | H | Br |
| 1-27 | SO$_2$Me | H | SMe |
| 1-28 | SO$_2$Me | H | SOMe |
| 1-29 | SO$_2$Me | H | SO$_2$Me |
| 1-30 | SO$_2$Me | H | SO$_2$Et |
| 1-31 | SO$_2$Me | H | CF$_3$ |
| 1-32 | SO$_2$Et | H | Cl |
| 1-33 | SO$_2$Et | H | Br |
| 1-34 | SO$_2$Et | H | SMe |
| 1-35 | SO$_2$Et | H | SOMe |
| 1-36 | SO$_2$Et | H | SO$_2$Me |
| 1-37 | SO$_2$Et | H | CF$_3$ |
| 1-38 | NO$_2$ | H | F |
| 1-39 | NO$_2$ | H | Cl |
| 1-40 | NO$_2$ | H | Br |
| 1-41 | NO$_2$ | H | I |
| 1-42 | NO$_2$ | H | CN |
| 1-43 | NO$_2$ | H | SO$_2$Me |
| 1-44 | NO$_2$ | H | SO$_2$Et |
| 1-45 | NO$_2$ | H | CF$_3$ |
| 1-46 | Me | H | Cl |

TABLE 1-continued

Compounds of the general formula (I) according to the invention in which A is CY, B is CH and R is methyl

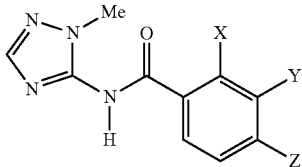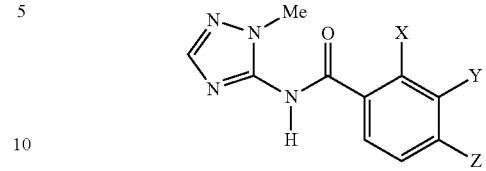

| No. | X | Y | Z |
|---|---|---|---|
| 1-47 | Me | H | Br |
| 1-48 | Me | H | SMe |
| 1-49 | Me | H | SO$_2$Me |
| 1-50 | Me | H | SO$_2$CH$_2$Cl |
| 1-51 | Me | H | SEt |
| 1-52 | Me | H | SO$_2$Et |
| 1-53 | Me | H | CF$_3$ |
| 1-54 | CH$_2$SO$_2$Me | H | CF$_3$ |
| 1-55 | Et | H | Cl |
| 1-56 | Et | H | Br |
| 1-57 | Et | H | SMe |
| 1-58 | Et | H | SO$_2$Me |
| 1-59 | Et | H | SO$_2$CH$_2$Cl |
| 1-60 | Et | H | SEt |
| 1-61 | Et | H | SO$_2$Et |
| 1-62 | Et | H | CF$_3$ |
| 1-63 | CF$_3$ | H | Cl |
| 1-64 | CF$_3$ | H | Br |
| 1-65 | CF$_3$ | H | SO$_2$Me |
| 1-66 | CF$_3$ | H | SO$_2$Et |
| 1-67 | CF$_3$ | H | CF$_3$ |
| 1-68 | NO$_2$ | NH$_2$ | F |
| 1-69 | NO$_2$ | NHMe | F |
| 1-70 | NO$_2$ | NMe$_2$ | F |
| 1-71 | NO$_2$ | Me | Cl |
| 1-72 | NO$_2$ | NH$_2$ | Cl |
| 1-73 | NO$_2$ | NHMe | Cl |
| 1-74 | NO$_2$ | NMe$_2$ | Cl |
| 1-75 | NO$_2$ | NH$_2$ | Br |
| 1-76 | NO$_2$ | NHMe | Br |
| 1-77 | NO$_2$ | NMe$_2$ | Br |
| 1-78 | NO$_2$ | NH$_2$ | CF$_3$ |
| 1-79 | NO$_2$ | NMe$_2$ | CF$_3$ |
| 1-80 | NO$_2$ | NH$_2$ | SO$_2$Me |
| 1-81 | NO$_2$ | NH$_2$ | SO$_2$Et |
| 1-82 | NO$_2$ | NHMe | SO$_2$Me |
| 1-83 | NO$_2$ | NMe$_2$ | SO$_2$Me |
| 1-84 | NO$_2$ | NMe$_2$ | SO$_2$Et |
| 1-85 | NO$_2$ | NH$_2$ | 1H-1,2,4-triazol-1-yl |
| 1-86 | NO$_2$ | NHMe | 1H-1,2,4-triazol-1-yl |
| 1-87 | NO$_2$ | NMe$_2$ | 1H-1,2,4-triazol-1-yl |
| 1-88 | Me | SMe | H |
| 1-89 | Me | SOMe | H |
| 1-90 | Me | SO$_2$Me | H |
| 1-91 | Me | SEt | H |
| 1-92 | Me | SOEt | H |
| 1-93 | Me | SO$_2$Et | H |
| 1-94 | Me | S(CH$_2$)$_2$OMe | H |
| 1-95 | Me | SO(CH$_2$)$_2$OMe | H |
| 1-96 | Me | SO$_2$(CH$_2$)$_2$OMe | H |
| 1-97 | Me | F | F |
| 1-98 | Me | F | Cl |
| 1-99 | Me | SEt | F |
| 1-100 | Me | SOEt | F |
| 1-101 | Me | SO$_2$Et | F |
| 1-102 | Me | Me | Cl |
| 1-103 | Me | F | Cl |
| 1-104 | Me | Cl | Cl |
| 1-105 | Me | NH$_2$ | Cl |
| 1-106 | Me | NHMe | Cl |
| 1-107 | Me | NMe$_2$ | Cl |
| 1-108 | Me | O(CH$_2$)$_2$OMe | Cl |
| 1-109 | Me | O(CH$_2$)$_3$OMe | Cl |
| 1-110 | Me | O(CH$_2$)$_4$OMe | Cl |
| 1-111 | Me | OCH$_2$CONMe$_2$ | Cl |
| 1-112 | Me | O(CH$_2$)$_2$—CO—NMe$_2$ | Cl |
| 1-113 | Me | O(CH$_2$)$_2$—NH(CO)NMe$_2$ | Cl |
| 1-114 | Me | O(CH$_2$)$_2$—NH(CO)NHCO$_2$Et | Cl |
| 1-115 | Me | O(CH$_2$)$_2$—NHCO$_2$Me | Cl |
| 1-116 | Me | OCH$_2$—NHSO$_2$cPr | Cl |
| 1-117 | Me | O(CH$_2$)-5-2,4-dimethyl-2,4-dihydro-3H-1,2,4-triazol-3-on | Cl |
| 1-118 | Me | O(CH$_2$)-3,5-dime-thyl-1,2-oxazol-4-yl | Cl |
| 1-119 | Me | SMe | Cl |
| 1-120 | Me | SOMe | Cl |
| 1-121 | Me | SO$_2$Me | Cl |
| 1-122 | Me | SEt | Cl |
| 1-123 | Me | SOEt | Cl |
| 1-124 | Me | SO$_2$Et | Cl |
| 1-125 | Me | S(CH$_2$)$_2$OMe | Cl |
| 1-126 | Me | SO(CH$_2$)$_2$OMe | Cl |
| 1-127 | Me | SO$_2$(CH$_2$)$_2$OMe | Cl |
| 1-128 | Me | NH$_2$ | Br |
| 1-129 | Me | NHMe | Br |
| 1-130 | Me | NMe$_2$ | Br |
| 1-131 | Me | OCH$_2$(CO)NMe$_2$ | Br |
| 1-132 | Me | O(CH$_2$)-5-pyrrolidin-2-on | Br |
| 1-133 | Me | SMe | Br |
| 1-134 | Me | SOMe | Br |
| 1-135 | Me | SO$_2$Me | Br |
| 1-136 | Me | SEt | Br |
| 1-137 | Me | SOEt | Br |
| 1-138 | Me | SO$_2$Et | Br |
| 1-139 | Me | SMe | I |
| 1-140 | Me | SOMe | I |
| 1-141 | Me | SO$_2$Me | I |
| 1-142 | Me | SEt | I |
| 1-143 | Me | SOEt | I |
| 1-144 | Me | SO$_2$Et | I |
| 1-145 | Me | Cl | CF$_3$ |
| 1-146 | Me | SMe | CF$_3$ |
| 1-147 | Me | SOMe | CF$_3$ |
| 1-148 | Me | SO$_2$Me | CF$_3$ |
| 1-149 | Me | SEt | CF$_3$ |
| 1-150 | Me | SOEt | CF$_3$ |
| 1-151 | Me | SO$_2$Et | CF$_3$ |
| 1-152 | Me | S(CH$_2$)$_2$OMe | CF$_3$ |
| 1-153 | Me | SO(CH$_2$)$_2$OMe | CF$_3$ |
| 1-154 | Me | SO$_2$(CH$_2$)$_2$OMe | CF$_3$ |
| 1-155 | Me | Me | SO$_2$Me |
| 1-156 | Me | 4,5-dihydro-1,2-oxazol-3 yl | SO$_2$Me |
| 1-157 | Me | 4,5-dihydro-1,2-oxazol-3 yl | SO$_2$Et |
| 1-158 | Me | 5-cyanomethyl-4,5-dihydro-1,2-oxazol-3-yl | SO$_2$Me |
| 1-159 | Me | 5-cyanomethyl-4,5-dihydro-1,2-oxazol-3-yl | SO$_2$Et |
| 1-160 | Me | NH$_2$ | SO$_2$Me |
| 1-161 | Me | NHMe | SO$_2$Me |
| 1-162 | Me | NMe$_2$ | SO$_2$Me |
| 1-163 | Me | NH(CH$_2$)$_2$OMe | SO$_2$Me |
| 1-164 | Me | pyrazol-1-yl | SO$_2$Me |
| 1-165 | Me | OH | SO$_2$Me |
| 1-166 | Me | OMe | SO$_2$Me |
| 1-167 | Me | OMe | SO$_2$Et |
| 1-168 | Me | OEt | SO$_2$Me |
| 1-169 | Me | OEt | SO$_2$Et |
| 1-170 | Me | OiPr | SO$_2$Me |
| 1-171 | Me | OiPr | SO$_2$Et |

TABLE 1-continued

Compounds of the general formula (I) according to the invention in which A is CY, B is CH and R is methyl

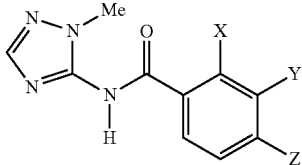
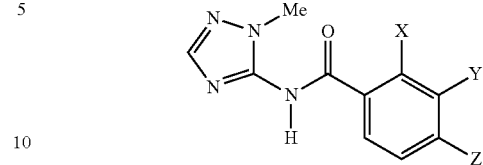

| No. | X | Y | Z |
|---|---|---|---|
| 1-172 | Me | O(CH$_2$)$_2$OMe | SO$_2$Me |
| 1-173 | Me | O(CH$_2$)$_2$OMe | SO$_2$Et |
| 1-174 | Me | O(CH$_2$)$_3$OMe | SO$_2$Me |
| 1-175 | Me | O(CH$_2$)$_3$OMe | SO$_2$Et |
| 1-176 | Me | O(CH$_2$)$_4$OMe | SO$_2$Me |
| 1-177 | Me | O(CH$_2$)$_4$OMe | SO$_2$Et |
| 1-178 | Me | O(CH$_2$)$_2$NHSO2Me | SO$_2$Me |
| 1-179 | Me | O(CH$_2$)$_2$NHSO2Me | SO$_2$Et |
| 1-180 | Me | OCH$_2$(CO)NMe$_2$ | SO$_2$Me |
| 1-181 | Me | OCH$_2$(CO)NMe$_2$ | SO$_2$Et |
| 1-182 | Me | [1,4]dioxan-2-yl-methoxy | SO$_2$Me |
| 1-183 | Me | [1,4]dioxan-2-yl-methoxy | SO$_2$Et |
| 1-184 | Me | O(CH$_2$)$_2$-O(3,5-di-methoxypyrimidin-2-yl | SO$_2$Me |
| 1-185 | Me | Cl | SO$_2$Me |
| 1-186 | Me | SMe | SO$_2$Me |
| 1-187 | Me | SOMe | SO$_2$Me |
| 1-188 | Me | SO$_2$Me | SO$_2$Me |
| 1-189 | Me | SO$_2$Me | SO$_2$Et |
| 1-190 | Me | SEt | SO$_2$Me |
| 1-191 | Me | SOEt | SO$_2$Me |
| 1-192 | Me | SO$_2$Et | SO$_2$Me |
| 1-193 | Me | S(CH$_2$)$_2$OMe | SO$_2$Me |
| 1-194 | Me | SO(CH$_2$)$_2$OMe | SO$_2$Me |
| 1-195 | Me | SO$_2$(CH$_2$)$_2$OMe | SO2Me |
| 1-196 | CH$_2$SMe | OMe | SO$_2$Me |
| 1-197 | CH$_2$OMe | OMe | SO$_2$Me |
| 1-198 | CH$_2$O(CH$_2$)$_2$OMe | NH(CH$_2$)$_2$OEt | SO$_2$Me |
| 1-199 | CH$_2$O(CH$_2$)$_2$OMe | NH(CH$_2$)$_3$OEt | SO$_2$Me |
| 1-200 | CH$_2$O(CH$_2$)$_3$OMe | OMe | SO$_2$Me |
| 1-201 | CH$_2$O(CH$_2$)$_2$OMe | NH(CH$_2$)$_2$OMe | SO$_2$Me |
| 1-202 | CH$_2$O(CH$_2$)$_2$OMe | NH(CH$_2$)$_3$OMe | SO$_2$Me |
| 1-203 | Et | SMe | Cl |
| 1-204 | Et | SO$_2$Me | Cl |
| 1-205 | Et | SMe | CF$_3$ |
| 1-206 | Et | SO$_2$Me | CF$_3$ |
| 1-207 | Et | F | SO$_2$Me |
| 1-208 | Et | NH(CH$_2$)$_2$OMe | SO$_2$Me |
| 1-209 | iPr | SO$_2$Me | CF$_3$ |
| 1-210 | cPr | SO$_2$Me | CF$_3$ |
| 1-211 | CF$_3$ | O(CH$_2$)$_2$OMe | F |
| 1-212 | CF$_3$ | O(CH$_2$)$_3$OMe | F |
| 1-213 | CF$_3$ | OCH$_2$CONMe$_2$ | F |
| 1-214 | CF$_3$ | [1,4]dioxan-2-yl-methoxy | F |
| 1-215 | CF$_3$ | O(CH$_2$)$_2$OMe | Cl |
| 1-216 | CF$_3$ | O(CH$_2$)$_3$OMe | Cl |
| 1-217 | CF$_3$ | OCH$_2$CONMe$_2$ | Cl |
| 1-218 | CF$_3$ | [1,4]dioxan-2-yl-methoxy | Cl |
| 1-219 | CF$_3$ | O(CH$_2$)$_2$OMe | Br |
| 1-220 | CF$_3$ | O(CH$_2$)$_3$OMe | Br |
| 1-221 | CF$_3$ | OCH$_2$CONMe$_2$ | Br |
| 1-222 | CF$_3$ | [1,4]dioxan-2-yl-methoxy | Br |
| 1-223 | CF$_3$ | O(CH$_2$)$_2$OMe | I |
| 1-224 | CF$_3$ | O(CH$_2$)$_3$OMe | I |
| 1-225 | CF$_3$ | OCH$_2$CONMe$_2$ | I |
| 1-226 | CF$_3$ | [1,4]dioxan-2-yl-methoxy | I |
| 1-227 | CF$_3$ | F | SO$_2$Me |
| 1-228 | CF$_3$ | F | SO$_2$Et |
| 1-229 | CF$_3$ | O(CH$_2$)$_2$OMe | SO$_2$Me |
| 1-230 | CF$_3$ | O(CH$_2$)$_2$OMe | SO$_2$Et |
| 1-231 | CF$_3$ | O(CH$_2$)$_3$OMe | SO$_2$Me |
| 1-232 | CF$_3$ | O(CH$_2$)$_3$OMe | SO$_2$Et |
| 1-233 | CF$_3$ | OCH$_2$CONMe$_2$ | SO$_2$Me |
| 1-234 | CF$_3$ | OCH$_2$CONMe$_2$ | SO$_2$Et |
| 1-235 | CF$_3$ | [1,4]dioxan-2-yl-methoxy | SO$_2$Me |
| 1-236 | CF$_3$ | [1,4]dioxan-2-yl-methoxy | SO$_2$Et |
| 1-237 | F | SMe | CF$_3$ |
| 1-238 | F | SOMe | CF$_3$ |
| 1-239 | Cl | Me | Cl |
| 1-240 | Cl | OCH$_2$CHCH$_2$ | Cl |
| 1-241 | Cl | OCH$_2$CHF$_2$ | Cl |
| 1-242 | Cl | O(CH$_2$)$_2$OMe | Cl |
| 1-243 | Cl | OCH$_2$CONMe$_2$ | Cl |
| 1-244 | Cl | O(CH$_2$)-5-pyrrolidin-2-on | Cl |
| 1-245 | Cl | SMe | Cl |
| 1-246 | Cl | SOMe | Cl |
| 1-247 | Cl | SO$_2$Me | Cl |
| 1-248 | Cl | F | SMe |
| 1-249 | Cl | Cl | SO$_2$Me |
| 1-250 | Cl | COOMe | SO$_2$Me |
| 1-251 | Cl | CONMe$_2$ | SO$_2$Me |
| 1-252 | Cl | CONMe(OMe) | SO$_2$Me |
| 1-253 | Cl | CH$_2$OMe | SO$_2$Me |
| 1-254 | Cl | CH$_2$OMe | SO$_2$Et |
| 1-255 | Cl | CH$_2$OEt | SO$_2$Me |
| 1-256 | Cl | CH$_2$OEt | SO$_2$Et |
| 1-257 | Cl | CH$_2$OCH$_2$CHF$_2$ | SO$_2$Me |
| 1-258 | Cl | CH$_2$OCH$_2$CF$_3$ | SO$_2$Me |
| 1-259 | Cl | CH$_2$OCH$_2$CF$_3$ | SO$_2$Et |
| 1-260 | Cl | CH$_2$OCH$_2$CF$_2$CHF$_2$ | SO$_2$Me |
| 1-261 | Cl | CH$_2$OcPentyl | SO$_2$Me |
| 1-262 | Cl | CH$_2$PO(OMe)$_2$ | SO$_2$Me |
| 1-263 | Cl | 4,5-dihydro-1,2-oxazol-3 yl | SMe |
| 1-264 | Cl | 4,5-dihydro-1,2-oxazol-3 yl | SO$_2$Me |
| 1-265 | Cl | 4,5-dihydro-1,2-oxazol-3 yl | SO$_2$Et |
| 1-266 | Cl | 5-cyanomethyl-4,5-dihydro-1,2-oxazol-3 yl | SO$_2$Me |
| 1-267 | Cl | 5-cyanomethyl-4,5-dihydro-1,2-oxazol-3 yl | SO$_2$Et |
| 1-268 | Cl | 5-(Methoxyme-thyl)-4,5-dihydro-1,2-oxazol-3 yl | SO$_2$Et |
| 1-269 | Cl | 5-(Methoxyme-thyl)-5-Methyl-4,5-dihydro-1,2-oxazol-3 yl | SO$_2$Et |
| 1-270 | Cl | CH$_2$O-tetrahydrofuran-3-yl | SO$_2$Me |
| 1-271 | Cl | CH$_2$O-tetra-hydrofuran-3-yl | SO$_2$Et |
| 1-272 | Cl | CH$_2$OCH$_2$-tetrahydrofuran-2-yl | SO$_2$Me |
| 1-273 | Cl | CH$_2$OCH$_2$-tetra-hydrofuran-2-yl | SO$_2$Et |
| 1-274 | Cl | CH$_2$OCH$_2$-tetra-hydrofuran-3-yl | SO$_2$Me |
| 1-275 | Cl | CH$_2$OCH$_2$-tetra-hydrofuran-3-yl | SO$_2$Et |
| 1-276 | Cl | OMe | SO$_2$Me |
| 1-277 | Cl | OMe | SO$_2$Et |
| 1-278 | Cl | OEt | SO$_2$Me |
| 1-279 | Cl | OEt | SO$_2$Et |
| 1-280 | Cl | OiPr | SO$_2$Me |
| 1-281 | Cl | OiPr | SO$_2$Et |
| 1-282 | Cl | O(CH$_2$)$_2$OMe | SO$_2$Me |
| 1-283 | Cl | O(CH$_2$)$_4$OMe | SO$_2$Me |
| 1-284 | Cl | O(CH$_2$)$_4$OMe | SO$_2$Et |
| 1-285 | Cl | O(CH$_2$)$_3$OMe | SO$_2$Me |
| 1-286 | Cl | O(CH$_2$)$_3$OMe | SO$_2$Et |
| 1-287 | Cl | O(CH$_2$)$_2$OMe | SO$_2$Me |
| 1-288 | Cl | O(CH$_2$)$_2$OMe | SO$_2$Et |
| 1-289 | Cl | [1,4]dioxan-2-yl-methoxy | SO$_2$Me |
| 1-290 | Cl | [1,4]dioxan-2-yl-methoxy | SO$_2$Et |
| 1-291 | Cl | OCH$_2$(CO)NMe$_2$ | SO$_2$Me |
| 1-292 | Cl | OCH$_2$(CO)NMe$_2$ | SO$_2$Et |
| 1-293 | Cl | SMe | SO$_2$Me |

TABLE 1-continued

Compounds of the general formula (I) according to the invention in which A is CY, B is CH and R is methyl

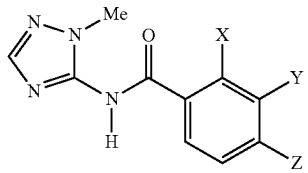

| No. | X | Y | Z |
|---|---|---|---|
| 1-294 | Cl | SOMe | SO₂Me |
| 1-295 | Br | OMe | Br |
| 1-296 | Br | O(CH₂)₂OMe | Br |
| 1-297 | Br | O(CH₂)₂OMe | SO₂Me |
| 1-298 | Br | O(CH₂)₂OMe | SO₂Et |
| 1-299 | Br | O(CH₂)₃OMe | SO₂Me |
| 1-300 | Br | O(CH₂)₃OMe | SO₂Et |
| 1-301 | Br | O(CH₂)₄OMe | SO₂Me |
| 1-302 | Br | O(CH₂)₄OMe | SO₂Et |
| 1-303 | Br | [1,4]dioxan-2-yl-methoxy | SO₂Me |
| 1-304 | Br | [1,4]dioxan-2-yl-methoxy | SO₂Et |
| 1-305 | I | O(CH₂)₂OMe | SO₂Me |
| 1-306 | I | O(CH₂)₂OMe | SO₂Et |
| 1-307 | I | O(CH₂)₃OMe | SO₂Me |
| 1-308 | I | O(CH₂)₃OMe | SO₂Et |
| 1-309 | I | O(CH₂)₄OMe | SO₂Me |
| 1-310 | I | O(CH₂)₄OMe | SO₂Et |
| 1-311 | I | [1,4]dioxan-2-yl-methoxy | SO₂Me |
| 1-312 | I | [1,4]dioxan-2-yl-methoxy | SO₂Et |
| 1-313 | OMe | SMe | CF₃ |
| 1-314 | OMe | SOMe | CF₃ |
| 1-315 | OMe | SO₂Me | CF₃ |
| 1-316 | OMe | SOEt | CF₃ |
| 1-317 | OMe | SO₂Et | CF₃ |
| 1-318 | OMe | S(CH₂)₂OMe | CF₃ |
| 1-319 | OMe | SO(CH₂)₂OMe | CF₃ |
| 1-320 | OMe | SO₂(CH₂)₂OMe | CF₃ |
| 1-321 | OMe | SMe | Cl |
| 1-322 | OMe | SOMe | Cl |
| 1-323 | OMe | SO₂Me | Cl |
| 1-324 | OMe | SEt | Cl |
| 1-325 | OMe | SOEt | Cl |
| 1-326 | OMe | SO2Et | Cl |
| 1-327 | OMe | S(CH₂)₂OMe | Cl |
| 1-328 | OMe | SO(CH₂)₂OMe | Cl |
| 1-329 | OMe | SO₂(CH₂)₂OMe | Cl |
| 1-330 | OCH₂c-Pr | SMe | CF₃ |
| 1-331 | OCH₂c-Pr | SOMe | CF₃ |
| 1-332 | OCH₂c-Pr | SO₂Me | CF₃ |
| 1-333 | OCH₂c-Pr | SEt | CF₃ |
| 1-334 | OCH₂c-Pr | SOEt | CF₃ |
| 1-335 | OCH₂c-Pr | SO₂Et | CF₃ |
| 1-336 | OCH₂c-Pr | S(CH₂)₂OMe | CF₃ |
| 1-337 | OCH₂c-Pr | SO(CH₂)₂OMe | CF₃ |
| 1-338 | OCH₂c-Pr | SO₂(CH₂)₂OMe | CF₃ |
| 1-339 | OCH₂c-Pr | SMe | Cl |
| 1-340 | OCH₂c-Pr | SOMe | Cl |
| 1-341 | OCH₂c-Pr | SO₂Me | Cl |
| 1-342 | OCH₂c-Pr | SEt | Cl |
| 1-343 | OCH₂c-Pr | SOEt | Cl |
| 1-344 | OCH₂c-Pr | SO₂Et | Cl |
| 1-345 | OCH₂c-Pr | S(CH₂)₂OMe | Cl |
| 1-346 | OCH₂c-Pr | SO(CH₂)₂OMe | Cl |
| 1-347 | OCH₂c-Pr | SO₂(CH₂)₂OMe | Cl |
| 1-348 | OCH₂c-Pr | SMe | SO₂Me |
| 1-349 | OCH₂c-Pr | SOMe | SO₂Me |
| 1-350 | OCH₂c-Pr | SO₂Me | SO₂Me |
| 1-351 | OCH₂c-Pr | SEt | SO₂Me |
| 1-352 | OCH₂c-Pr | SOEt | SO₂Me |
| 1-353 | OCH₂c-Pr | SO₂Et | SO₂Me |
| 1-354 | OCH₂c-Pr | S(CH₂)₂OMe | SO₂Me |
| 1-355 | OCH₂c-Pr | SO(CH₂)₂OMe | SO₂Me |
| 1-356 | OCH₂c-Pr | SO₂(CH₂)₂OMe | SO₂Me |
| 1-357 | SO₂Me | F | CF₃ |
| 1-358 | SO₂Me | NH₂ | CF₃ |
| 1-359 | SO₂Me | NHEt | Cl |

TABLE 1-continued

Compounds of the general formula (I) according to the invention in which A is CY, B is CH and R is methyl

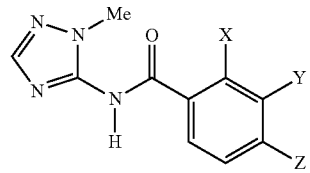

| No. | X | Y | Z |
|---|---|---|---|
| 1-360 | SMe | SEt | F |
| 1-361 | SMe | SMe | F |

TABLE 2

Compounds of the general formula (I) according to the invention in which A is CY, B is CH and R is ethyl

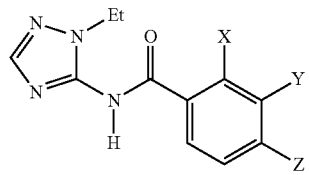

| No | X | Y | Z |
|---|---|---|---|
| 2-1 | F | H | Cl |
| 2-2 | F | H | Br |
| 2-3 | F | H | SO₂Me |
| 2-4 | F | H | SO₂Et |
| 2-5 | F | H | CF₃ |
| 2-6 | F | H | NO₂ |
| 2-7 | Cl | H | F |
| 2-8 | Cl | H | Cl |
| 2-9 | Cl | H | Br |
| 2-10 | Cl | H | SMe |
| 2-11 | Cl | H | SOMe |
| 2-12 | Cl | H | SO₂Me |
| 2-13 | Cl | H | SO₂CH₂Cl |
| 2-14 | Cl | H | SEt |
| 2-15 | Cl | H | SO₂Et |
| 2-16 | Cl | H | CF₃ |
| 2-17 | Cl | H | NO₂ |
| 2-18 | Cl | H | pyrazol-1-yl |
| 2-19 | Cl | H | 1H-1,2,4-triazol-1-yl |
| 2-20 | Br | H | Cl |
| 2-21 | Br | H | Br |
| 2-22 | Br | H | SO₂Me |
| 2-23 | Br | H | SO₂Et |
| 2-24 | Br | H | CF₃ |
| 2-25 | SO₂Me | H | Cl |
| 2-26 | SO₂Me | H | Br |
| 2-27 | SO₂Me | H | SMe |
| 2-28 | SO₂Me | H | SOMe |
| 2-29 | SO₂Me | H | SO₂Me |
| 2-30 | SO₂Me | H | SO₂Et |
| 2-31 | SO₂Me | H | CF₃ |
| 2-32 | SO₂Et | H | Cl |
| 2-33 | SO₂Et | H | Br |
| 2-34 | SO₂Et | H | SMe |
| 2-35 | SO₂Et | H | SOMe |
| 2-36 | SO₂Et | H | SO₂Me |
| 2-37 | SO₂Et | H | CF₃ |
| 2-38 | NO₂ | H | F |
| 2-39 | NO₂ | H | Cl |
| 2-40 | NO₂ | H | Br |
| 2-41 | NO₂ | H | I |
| 2-42 | NO₂ | H | CN |
| 2-43 | NO₂ | H | SO₂Me |
| 2-44 | NO₂ | H | SO₂Et |

TABLE 2-continued

Compounds of the general formula (I) according to the invention in which A is CY, B is CH and R is ethyl

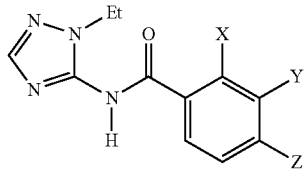

| No | X | Y | Z |
|---|---|---|---|
| 2-45 | NO₂ | H | CF₃ |
| 2-46 | Me | H | Cl |
| 2-47 | Me | H | Br |
| 2-48 | Me | H | SMe |
| 2-49 | Me | H | SO₂Me |
| 2-50 | Me | H | SO₂CH₂Cl |
| 2-51 | Me | H | SEt |
| 2-52 | Me | H | SO₂Et |
| 2-53 | Me | H | CF₃ |
| 2-54 | CH₂SO₂Me | H | CF₃ |
| 2-55 | Et | H | Cl |
| 2-56 | Et | H | Br |
| 2-57 | Et | H | SMe |
| 2-58 | Et | H | SO₂Me |
| 2-59 | Et | H | SO₂CH₂Cl |
| 2-60 | Et | H | SEt |
| 2-61 | Et | H | SO₂Et |
| 2-62 | Et | H | CF₃ |
| 2-63 | CF₃ | H | Cl |
| 2-64 | CF₃ | H | Br |
| 2-65 | CF₃ | H | SO₂Me |
| 2-66 | CF₃ | H | SO₂Et |
| 2-67 | CF₃ | H | CF₃ |
| 2-68 | NO₂ | NH₂ | F |
| 2-69 | NO₂ | NHMe | F |
| 2-70 | NO₂ | NMe₂ | F |
| 2-71 | NO₂ | Me | Cl |
| 2-72 | NO₂ | NH₂ | Cl |
| 2-73 | NO₂ | NHMe | Cl |
| 2-74 | NO₂ | NMe₂ | Cl |
| 2-75 | NO₂ | NH₂ | Br |
| 2-76 | NO₂ | NHMe | Br |
| 2-77 | NO₂ | NMe₂ | Br |
| 2-78 | NO₂ | NH₂ | CF₃ |
| 2-79 | NO₂ | NMe₂ | CF₃ |
| 2-80 | NO₂ | NH₂ | SO₂Me |
| 2-81 | NO₂ | NH₂ | SO₂Et |
| 2-82 | NO₂ | NHMe | SO₂Me |
| 2-83 | NO₂ | NMe₂ | SO₂Me |
| 2-84 | NO₂ | NMe₂ | SO₂Et |
| 2-85 | NO₂ | NH₂ | 1H-1,2,4-triazol-1-yl |
| 2-86 | NO₂ | NHMe | 1H-1,2,4-triazol-1-yl |
| 2-87 | NO₂ | NMe₂ | 1H-1,2,4-triazol-1-yl |
| 2-88 | Me | SMe | H |
| 2-89 | Me | SOMe | H |
| 2-90 | Me | SO₂Me | H |
| 2-91 | Me | SEt | H |
| 2-92 | Me | SOEt | H |
| 2-93 | Me | SO₂Et | H |
| 2-94 | Me | S(CH₂)₂OMe | H |
| 2-95 | Me | SO(CH₂)₂OMe | H |
| 2-96 | Me | SO₂(CH₂)₂OMe | H |
| 2-97 | Me | F | F |
| 2-98 | Me | F | Cl |
| 2-99 | Me | SEt | F |
| 2-100 | Me | SOEt | F |
| 2-101 | Me | SO₂Et | F |
| 2-102 | Me | Me | Cl |
| 2-103 | Me | F | Cl |
| 2-104 | Me | Cl | Cl |
| 2-105 | Me | NH₂ | Cl |
| 2-106 | Me | NHMe | Cl |
| 2-107 | Me | NMe₂ | Cl |

TABLE 2-continued

Compounds of the general formula (I) according to the invention in which A is CY, B is CH and R is ethyl

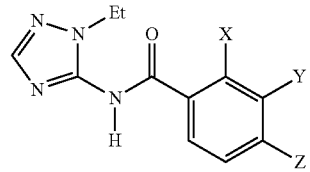

| No | X | Y | Z |
|---|---|---|---|
| 2-108 | Me | O(CH₂)₂OMe | Cl |
| 2-109 | Me | O(CH₂)₃OMe | Cl |
| 2-110 | Me | O(CH₂)₄OMe | Cl |
| 2-111 | Me | OCH₂CONMe₂ | Cl |
| 2-112 | Me | O(CH₂)₂—CO—NMe₂ | Cl |
| 2-113 | Me | O(CH₂)₂—NH(CO)NMe₂ | Cl |
| 2-114 | Me | O(CH₂)₂—NH(CO)NHCO₂Et | Cl |
| 2-115 | Me | O(CH₂)₂—NHCO₂Me | Cl |
| 2-116 | Me | O—CH₂—NHSO₂cPr | Cl |
| 2-117 | Me | O(CH₂)-5-2,4-dime-thyl-2,4-dihydro-3H-1,2,4-triazol-3-on | Cl |
| 2-118 | Me | O(CH₂)-3,5-dime-thyl-1,2-oxazol-4-yl | Cl |
| 2-119 | Me | SMe | Cl |
| 2-120 | Me | SOMe | Cl |
| 2-121 | Me | SO₂Me | Cl |
| 2-122 | Me | SEt | Cl |
| 2-123 | Me | SOEt | Cl |
| 2-124 | Me | SO₂Et | Cl |
| 2-125 | Me | S(CH₂)₂OMe | Cl |
| 2-126 | Me | SO(CH₂)₂OMe | Cl |
| 2-127 | Me | SO₂(CH₂)₂OMe | Cl |
| 2-128 | Me | NH₂ | Br |
| 2-129 | Me | NHMe | Br |
| 2-130 | Me | NMe₂ | Br |
| 2-131 | Me | O(CH₂)CONEt₂ | Br |
| 2-132 | Me | O(CH₂)-5-pyrrolidin-2-on | Br |
| 2-133 | Me | SMe | Br |
| 2-134 | Me | SOMe | Br |
| 2-135 | Me | SO₂Me | Br |
| 2-136 | Me | SEt | Br |
| 2-137 | Me | SOEt | Br |
| 2-138 | Me | SO₂Et | Br |
| 2-139 | Me | SMe | I |
| 2-140 | Me | SOMe | I |
| 2-141 | Me | SO₂Me | I |
| 2-142 | Me | SEt | I |
| 2-143 | Me | SOEt | I |
| 2-144 | Me | SO₂Et | I |
| 2-145 | Me | Cl | CF₃ |
| 2-146 | Me | SMe | CF₃ |
| 2-147 | Me | SOMe | CF₃ |
| 2-148 | Me | SO₂Me | CF₃ |
| 2-149 | Me | SEt | CF₃ |
| 2-150 | Me | SOEt | CF₃ |
| 2-151 | Me | SO₂Et | CF₃ |
| 2-152 | Me | S(CH₂)₂OMe | CF₃ |
| 2-153 | Me | SO(CH₂)₂OMe | CF₃ |
| 2-154 | Me | SO₂(CH₂)₂OMe | CF₃ |
| 2-155 | Me | Me | SO₂Me |
| 2-156 | Me | 4,5-dihydro-1,2-oxazol-3 yl | SO₂Me |
| 2-157 | Me | 4,5-dihydro-1,2-oxazol-3 yl | SO₂Et |
| 2-158 | Me | 5-cyanomethyl-4,5-dihydro-1,2-oxazol-3-yl | SO₂Me |
| 2-159 | Me | 5-cyanomethyl-4,5-dihydro-1,2-oxazol-3-yl | SO₂Et |
| 2-160 | Me | NH₂ | SO₂Me |
| 2-161 | Me | NHMe | SO₂Me |
| 2-162 | Me | NMe₂ | SO₂Me |
| 2-163 | Me | NH(CH₂)₂OMe | SO₂Me |
| 2-164 | Me | Pyrazol-1-yl | SO₂Me |
| 2-165 | Me | OH | SO₂Me |
| 2-166 | Me | OMe | SO₂Me |
| 2-167 | Me | OMe | SO₂Et |
| 2-168 | Me | OEt | SO₂Me |
| 2-169 | Me | OEt | SO₂Et |

TABLE 2-continued

Compounds of the general formula (I) according to the invention in which A is CY, B is CH and R is ethyl

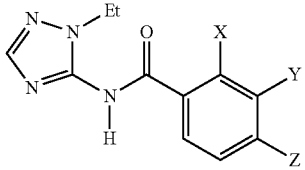

| No | X | Y | Z |
|---|---|---|---|
| 2-170 | Me | OiPr | SO₂Me |
| 2-171 | Me | OiPr | SO₂Et |
| 2-172 | Me | O(CH₂)₂OMe | SO₂Me |
| 2-173 | Me | O(CH₂)₂OMe | SO₂Et |
| 2-174 | Me | O(CH₂)₃OMe | SO₂Me |
| 2-175 | Me | O(CH₂)₃OMe | SO₂Et |
| 2-176 | Me | O(CH₂)₄OMe | SO₂Me |
| 2-177 | Me | O(CH₂)₄OMe | SO₂Et |
| 2-178 | Me | O(CH₂)₂NHSO2Me | SO₂Me |
| 2-179 | Me | O(CH₂)₂NHSO2Me | SO₂Et |
| 2-180 | Me | OCH₂(CO)NMe₂ | SO₂Me |
| 2-181 | Me | OCH₂(CO)NMe₂ | SO₂Et |
| 2-182 | Me | [1,4]dioxan-2-yl-methoxy | SO₂Me |
| 2-183 | Me | [1,4]dioxan-2-yl-methoxy | SO₂Et |
| 2-184 | Me | O(CH₂)₂—O(3,5-di-methoxypyrimidin-2-yl | SO₂Me |
| 2-185 | Me | Cl | SO₂Me |
| 2-186 | Me | SMe | SO₂Me |
| 2-187 | Me | SOMe | SO₂Me |
| 2-188 | Me | SO₂Me | SO₂Me |
| 2-189 | Me | SO₂Me | SO₂Et |
| 2-190 | Me | SEt | SO₂Me |
| 2-191 | Me | SOEt | SO₂Me |
| 2-192 | Me | SO₂Et | SO₂Me |
| 2-193 | Me | S(CH₂)₂OMe | SO₂Me |
| 2-194 | Me | SO(CH₂)₂OMe | SO₂Me |
| 2-195 | Me | SO₂(CH₂)₂OMe | SO2Me |
| 2-196 | CH₂SMe | OMe | SO₂Me |
| 2-197 | CH₂OMe | OMe | SO₂Me |
| 2-198 | CH₂O(CH₂)₂OMe | NH(CH₂)₂OEt | SO₂Me |
| 2-199 | CH₂O(CH₂)₂OMe | NH(CH₂)₃OEt | SO₂Me |
| 2-200 | CH₂O(CH₂)₃OMe | OMe | SO₂Me |
| 2-201 | CH₂O(CH₂)₂OMe | NH(CH₂)₂OMe | SO₂Me |
| 2-202 | CH₂O(CH₂)₂OMe | NH(CH₂)₃OMe | SO₂Me |
| 2-203 | Et | SMe | Cl |
| 2-204 | Et | SO₂Me | Cl |
| 2-205 | Et | SMe | CF₃ |
| 2-206 | Et | SO₂Me | CF₃ |
| 2-207 | Et | F | SO₂Me |
| 2-208 | Et | NH(CH₂)₂OMe | SO₂Me |
| 2-209 | iPr | SO₂Me | CF₃ |
| 2-210 | cPr | SO₂Me | CF₃ |
| 2-211 | CF₃ | O(CH₂)₂OMe | F |
| 2-212 | CF₃ | O(CH₂)₃OMe | F |
| 2-213 | CF₃ | OCH₂CONMe₂ | F |
| 2-214 | CF₃ | [1,4]dioxan-2-yl-methoxy | F |
| 2-215 | CF₃ | O(CH₂)₂OMe | Cl |
| 2-216 | CF₃ | O(CH₂)₃OMe | Cl |
| 2-217 | CF₃ | OCH₂CONMe₂ | Cl |
| 2-218 | CF₃ | [1,4]dioxan-2-yl-methoxy | Cl |
| 2-219 | CF₃ | O(CH₂)₂OMe | Br |
| 2-220 | CF₃ | O(CH₂)₃OMe | Br |
| 2-221 | CF₃ | OCH₂CONMe₂ | Br |
| 2-222 | CF₃ | [1,4]dioxan-2-yl-methoxy | Br |
| 2-223 | CF₃ | O(CH₂)₂OMe | I |
| 2-224 | CF₃ | O(CH₂)₃OMe | I |
| 2-225 | CF₃ | OCH₂CONMe₂ | I |
| 2-226 | CF₃ | [1,4]dioxan-2-yl-methoxy | I |
| 2-227 | CF₃ | F | SO₂Me |
| 2-228 | CF₃ | F | SO₂Et |
| 2-229 | CF₃ | O(CH₂)₂OMe | SO₂Me |
| 2-230 | CF₃ | O(CH₂)₂OMe | SO₂Et |
| 2-231 | CF₃ | O(CH₂)₃OMe | SO₂Me |
| 2-232 | CF₃ | O(CH₂)₃OMe | SO₂Et |
| 2-233 | CF₃ | OCH₂CONMe₂ | SO₂Me |
| 2-234 | CF₃ | OCH₂CONMe₂ | SO₂Et |

TABLE 2-continued

Compounds of the general formula (I) according to the invention in which A is CY, B is CH and R is ethyl

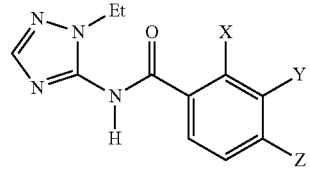

| No | X | Y | Z |
|---|---|---|---|
| 2-235 | CF₃ | [1,4]dioxan-2-yl-methoxy | SO₂Me |
| 2-236 | CF₃ | [1,4]dioxan-2-yl-methoxy | SO₂Et |
| 2-237 | F | SMe | CF₃ |
| 2-238 | F | SOMe | CF₃ |
| 2-239 | Cl | Me | Cl |
| 2-240 | Cl | OCH₂CHCH₂ | Cl |
| 2-241 | Cl | OCH₂CHF₂ | Cl |
| 2-242 | Cl | O(CH₂)₂OMe | Cl |
| 2-243 | Cl | OCH₂(CO)NMe₂ | Cl |
| 2-244 | Cl | O(CH₂)-5-pyrrolidin-2-on | Cl |
| 2-245 | Cl | SMe | Cl |
| 2-246 | Cl | SOMe | Cl |
| 2-247 | Cl | SO₂Me | Cl |
| 2-248 | Cl | F | SMe |
| 2-249 | Cl | Cl | SO₂Me |
| 2-250 | Cl | COOMe | SO₂Me |
| 2-251 | Cl | CONMe₂ | SO₂Me |
| 2-252 | Cl | CONMe(OMe) | SO₂Me |
| 2-253 | Cl | CH₂OMe | SO₂Me |
| 2-254 | Cl | CH₂OMe | SO₂Et |
| 2-255 | Cl | CH₂OEt | SO₂Me |
| 2-256 | Cl | CH₂OEt | SO₂Et |
| 2-257 | Cl | CH₂OCH₂CHF₂ | SO₂Me |
| 2-258 | Cl | CH₂OCH₂CF₃ | SO₂Me |
| 2-259 | Cl | CH₂OCH₂CF₃ | SO₂Et |
| 2-260 | Cl | CH₂OCH₂CF₂CHF₂ | SO₂Me |
| 2-261 | Cl | CH₂OcPentyl | SO₂Me |
| 2-262 | Cl | CH₂PO(OMe)₂ | SO₂Me |
| 2-263 | Cl | 4,5-dihydro-1,2-oxazol-3 yl | SMe |
| 2-264 | Cl | 4,5-dihydro-1,2-oxazol-3 yl | SO₂Me |
| 2-265 | Cl | 4,5-dihydro-1,2-oxazol-3 yl | SO₂Et |
| 2-266 | Cl | 5-cyanomethyl-4,5-dihydro-1,2-oxazol-3 yl | SO₂Me |
| 2-267 | Cl | 5-cyanomethyl-4,5-dihydro-1,2-oxazol-3 yl | SO₂Et |
| 2-268 | Cl | 5-(Methoxymethyl)-4,5-dihydro-1,2-oxazol-3 yl | SO₂Et |
| 2-269 | Cl | 5-(Methoxymethyl)-5-Methyl-4,5-dihy-dro-1,2-oxazol-3 yl | SO₂Et |
| 2-270 | Cl | CH₂O-tetrahydrofuran-3-yl | SO₂Me |
| 2-271 | Cl | CH₂O-tetrahydrofuran-3-yl | SO₂Et |
| 2-272 | Cl | CH₂OCH₂-tetrahydrofuran-2-yl | SO₂Me |
| 2-273 | Cl | CH₂OCH₂-tetrahydrofuran-2-yl | SO₂Et |
| 2-274 | Cl | CH₂OCH₂-tetrahydrofuran-3-yl | SO₂Me |
| 2-275 | Cl | CH₂OCH₂-tetrahydrofuran-3-yl | SO₂Et |
| 2-276 | Cl | OMe | SO₂Me |
| 2-277 | Cl | OMe | SO₂Et |
| 2-278 | Cl | OEt | SO₂Me |
| 2-279 | Cl | OEt | SO₂Et |
| 2-280 | Cl | OiPr | SO₂Me |
| 2-281 | Cl | OiPr | SO₂Et |
| 2-282 | Cl | O(CH₂)₄OMe | SO₂Me |
| 2-283 | Cl | O(CH₂)₄OMe | SO₂Me |
| 2-284 | Cl | O(CH₂)₄OMe | SO₂Et |
| 2-285 | Cl | O(CH₂)₃OMe | SO₂Me |
| 2-286 | Cl | O(CH₂)₃OMe | SO₂Et |
| 2-287 | Cl | O(CH₂)₂OMe | SO₂Me |
| 2-288 | Cl | O(CH₂)₂OMe | SO₂Et |
| 2-289 | Cl | [1,4]dioxan-2-yl-methoxy | SO₂Me |
| 2-290 | Cl | [1,4]dioxan-2-yl-methoxy | SO₂Et |
| 2-291 | Cl | OCH₂(CO)NMe₂ | SO₂Me |
| 2-292 | Cl | OCH₂(CO)NMe₂ | SO₂Et |

TABLE 2-continued

Compounds of the general formula (I) according to the invention in which A is CY, B is CH and R is ethyl

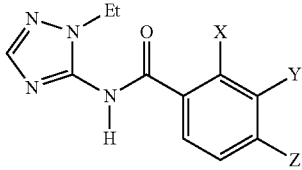

| No | X | Y | Z |
|---|---|---|---|
| 2-293 | Cl | SMe | SO$_2$Me |
| 2-294 | Cl | SOMe | SO$_2$Me |
| 2-295 | Br | OMe | Br |
| 2-296 | Br | O(CH$_2$)$_2$OMe | Br |
| 2-297 | Br | O(CH$_2$)$_2$OMe | SO$_2$Me |
| 2-298 | Br | O(CH$_2$)$_2$OMe | SO$_2$Et |
| 2-299 | Br | O(CH$_2$)$_3$OMe | SO$_2$Me |
| 2-300 | Br | O(CH$_2$)$_3$OMe | SO$_2$Et |
| 2-301 | Br | O(CH$_2$)$_4$OMe | SO$_2$Me |
| 2-302 | Br | O(CH$_2$)$_4$OMe | SO$_2$Et |
| 2-303 | Br | [1,4]dioxan-2-yl-methoxy | SO$_2$Me |
| 2-304 | Br | [1,4]dioxan-2-yl-methoxy | SO$_2$Et |
| 2-305 | I | O(CH$_2$)$_2$OMe | SO$_2$Me |
| 2-306 | I | O(CH$_2$)$_2$OMe | SO$_2$Et |
| 2-307 | I | O(CH$_2$)$_3$OMe | SO$_2$Me |
| 2-308 | I | O(CH$_2$)$_3$OMe | SO$_2$Et |
| 2-309 | I | O(CH$_2$)$_4$OMe | SO$_2$Me |
| 2-310 | I | O(CH$_2$)$_4$OMe | SO$_2$Et |
| 2-311 | I | [1,4]dioxan-2-yl-methoxy | SO$_2$Me |
| 2-312 | I | [1,4]dioxan-2-yl-methoxy | SO$_2$Et |
| 2-313 | OMe | SMe | CF$_3$ |
| 2-314 | OMe | SOMe | CF$_3$ |
| 2-315 | OMe | SO$_2$Me | CF$_3$ |
| 2-316 | OMe | SOEt | CF$_3$ |
| 2-317 | OMe | SO$_2$Et | CF$_3$ |
| 2-318 | OMe | S(CH$_2$)$_2$OMe | CF$_3$ |
| 2-319 | OMe | SO(CH$_2$)$_2$OMe | CF$_3$ |
| 2-320 | OMe | SO$_2$(CH$_2$)$_2$OMe | CF$_3$ |
| 2-321 | OMe | SMe | Cl |
| 2-322 | OMe | SOMe | Cl |
| 2-323 | OMe | SO$_2$Me | Cl |
| 2-324 | OMe | SEt | Cl |
| 2-325 | OMe | SOEt | Cl |
| 2-326 | OMe | SO2Et | Cl |
| 2-327 | OMe | S(CH$_2$)$_2$OMe | Cl |
| 2-328 | OMe | SO(CH$_2$)$_2$OMe | Cl |
| 2-329 | OMe | SO$_2$(CH$_2$)$_2$OMe | Cl |
| 2-330 | OCH$_2$c-Pr | SMe | CF$_3$ |
| 2-331 | OCH$_2$c-Pr | SOMe | CF$_3$ |
| 2-332 | OCH$_2$c-Pr | SO$_2$Me | CF$_3$ |
| 2-333 | OCH$_2$c-Pr | SEt | CF$_3$ |
| 2-334 | OCH$_2$c-Pr | SOEt | CF$_3$ |
| 2-335 | OCH$_2$c-Pr | SO$_2$Et | CF$_3$ |
| 2-336 | OCH$_2$c-Pr | S(CH$_2$)$_2$OMe | CF$_3$ |
| 2-337 | OCH$_2$c-Pr | SO(CH$_2$)$_2$OMe | CF$_3$ |
| 2-338 | OCH$_2$c-Pr | SO$_2$(CH$_2$)$_2$OMe | CF$_3$ |
| 2-339 | OCH$_2$c-Pr | SMe | Cl |
| 2-340 | OCH$_2$c-Pr | SOMe | Cl |
| 2-341 | OCH$_2$c-Pr | SO$_2$Me | Cl |
| 2-342 | OCH$_2$c-Pr | SEt | Cl |
| 2-343 | OCH$_2$c-Pr | SOEt | Cl |
| 2-344 | OCH$_2$c-Pr | SO$_2$Et | Cl |
| 2-345 | OCH$_2$c-Pr | S(CH$_2$)$_2$OMe | Cl |
| 2-346 | OCH$_2$c-Pr | SO(CH$_2$)$_2$OMe | Cl |
| 2-347 | OCH$_2$c-Pr | SO$_2$(CH$_2$)$_2$OMe | Cl |
| 2-348 | OCH$_2$c-Pr | SMe | SO$_2$Me |
| 2-349 | OCH$_2$c-Pr | SOMe | SO$_2$Me |
| 2-350 | OCH$_2$c-Pr | SO$_2$Me | SO$_2$Me |
| 2-351 | OCH$_2$c-Pr | SEt | SO$_2$Me |
| 2-352 | OCH$_2$c-Pr | SOEt | SO$_2$Me |
| 2-353 | OCH$_2$c-Pr | SO$_2$Et | SO$_2$Me |
| 2-354 | OCH$_2$c-Pr | S(CH$_2$)$_2$OMe | SO$_2$Me |
| 2-355 | OCH$_2$c-Pr | SO(CH$_2$)$_2$OMe | SO$_2$Me |
| 2-356 | OCH$_2$c-Pr | SO$_2$(CH$_2$)$_2$OMe | SO$_2$Me |
| 2-357 | SO$_2$Me | F | CF$_3$ |
| 2-358 | SO$_2$Me | NH$_2$ | CF$_3$ |
| 2-359 | SO$_2$Me | NHEt | Cl |
| 2-360 | SMe | SEt | F |
| 2-361 | SMe | SMe | F |

TABLE 3

Compounds of the general formula (I) according to the invention in which A is CY, B is CH and R is phenyl

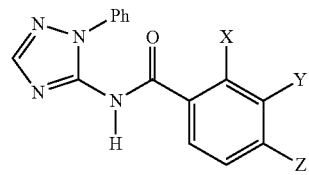

| No. | X | Y | Z |
|---|---|---|---|
| 3-1 | F | H | Cl |
| 3-2 | F | H | Br |
| 3-3 | F | H | SO$_2$Me |
| 3-4 | F | H | SO$_2$Et |
| 3-5 | F | H | CF$_3$ |
| 3-6 | F | H | NO$_2$ |
| 3-7 | Cl | H | F |
| 3-8 | Cl | H | Cl |
| 3-9 | Cl | H | Br |
| 3-10 | Cl | H | SMe |
| 3-11 | Cl | H | SOMe |
| 3-12 | Cl | H | SO$_2$Me |
| 3-13 | Cl | H | SO$_2$CH$_2$Cl |
| 3-14 | Cl | H | SEt |
| 3-15 | Cl | H | SO$_2$Et |
| 3-16 | Cl | H | CF$_3$ |
| 3-17 | Cl | H | NO$_2$ |
| 3-18 | Cl | H | pyrazol-1-yl |
| 3-19 | Cl | H | 1H-1,2,4-triazol-1-yl |
| 3-20 | Br | H | Cl |
| 3-21 | Br | H | Br |
| 3-22 | Br | H | SO$_2$Me |
| 3-23 | Br | H | SO$_2$Et |
| 3-24 | Br | H | CF$_3$ |
| 3-25 | SO$_2$Me | H | Cl |
| 3-26 | SO$_2$Me | H | Br |
| 3-27 | SO$_2$Me | H | SMe |
| 3-28 | SO$_2$Me | H | SOMe |
| 3-29 | SO$_2$Me | H | SO$_2$Me |
| 3-30 | SO$_2$Me | H | SO$_2$Et |
| 3-31 | SO$_2$Me | H | CF$_3$ |
| 3-32 | SO$_2$Et | H | Cl |
| 3-33 | SO$_2$Et | H | Br |
| 3-34 | SO$_2$Et | H | SMe |
| 3-35 | SO$_2$Et | H | SOMe |
| 3-36 | SO$_2$Et | H | SO$_2$Me |
| 3-37 | SO$_2$Et | H | CF$_3$ |
| 3-38 | NO$_2$ | H | F |
| 3-39 | NO$_2$ | H | Cl |
| 3-40 | NO$_2$ | H | Br |
| 3-41 | NO$_2$ | H | I |
| 3-42 | NO$_2$ | H | CN |
| 3-43 | NO$_2$ | H | SO$_2$Me |

TABLE 3-continued

Compounds of the general formula (I) according to the invention in which A is CY, B is CH and R is phenyl

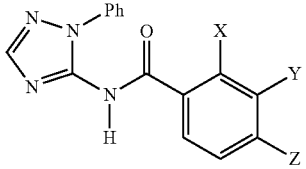
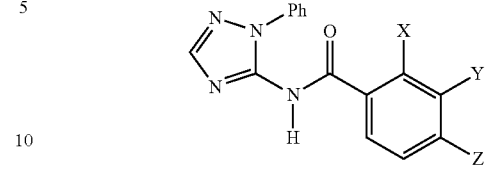

| No. | X | Y | Z |
|---|---|---|---|
| 3-44 | NO$_2$ | H | SO$_2$Et |
| 3-45 | NO$_2$ | H | CF$_3$ |
| 3-46 | Me | H | Cl |
| 3-47 | Me | H | Br |
| 3-48 | Me | H | SMe |
| 3-49 | Me | H | SO$_2$Me |
| 3-50 | Me | H | SO$_2$CH$_2$Cl |
| 3-51 | Me | H | SEt |
| 3-52 | Me | H | SO$_2$Et |
| 3-53 | Me | H | CF$_3$ |
| 3-54 | CH$_2$SO$_2$Me | H | CF$_3$ |
| 3-55 | Et | H | Cl |
| 3-56 | Et | H | Br |
| 3-57 | Et | H | SMe |
| 3-58 | Et | H | SO$_2$Me |
| 3-59 | Et | H | SO$_2$CH$_2$Cl |
| 3-60 | Et | H | SEt |
| 3-61 | Et | H | SO$_2$Et |
| 3-62 | Et | H | CF$_3$ |
| 3-63 | CF$_3$ | H | Cl |
| 3-64 | CF$_3$ | H | Br |
| 3-65 | CF$_3$ | H | SO$_2$Me |
| 3-66 | CF$_3$ | H | SO$_2$Et |
| 3-67 | CF$_3$ | H | CF$_3$ |
| 3-68 | NO$_2$ | NH$_2$ | F |
| 3-69 | NO$_2$ | NHMe | F |
| 3-70 | NO$_2$ | NMe$_2$ | F |
| 3-71 | NO$_2$ | Me | Cl |
| 3-72 | NO$_2$ | NH$_2$ | Cl |
| 3-73 | NO$_2$ | NHMe | Cl |
| 3-74 | NO$_2$ | NMe$_2$ | Cl |
| 3-75 | NO$_2$ | NH$_2$ | Br |
| 3-76 | NO$_2$ | NHMe | Br |
| 3-77 | NO$_2$ | NMe$_2$ | Br |
| 3-78 | NO$_2$ | NH$_2$ | CF$_3$ |
| 3-79 | NO$_2$ | NMe$_2$ | CF$_3$ |
| 3-80 | NO$_2$ | NH$_2$ | SO$_2$Me |
| 3-81 | NO$_2$ | NH$_2$ | SO$_2$Et |
| 3-82 | NO$_2$ | NHMe | SO$_2$Me |
| 3-83 | NO$_2$ | NMe$_2$ | SO$_2$Me |
| 3-84 | NO$_2$ | NMe$_2$ | SO$_2$Et |
| 3-85 | NO$_2$ | NH$_2$ | 1H-1,2,4-triazol-1-yl |
| 3-86 | NO$_2$ | NHMe | 1H-1,2,4-triazol-1-yl |
| 3-87 | NO$_2$ | NMe$_2$ | 1H-1,2,4-triazol-1-yl |
| 3-88 | Me | SMe | H |
| 3-89 | Me | SOMe | H |
| 3-90 | Me | SO$_2$Me | H |
| 3-91 | Me | SEt | H |
| 3-92 | Me | SOEt | H |
| 3-93 | Me | SO$_2$Et | H |
| 3-94 | Me | S(CH$_2$)$_2$OMe | H |
| 3-95 | Me | SO(CH$_2$)$_2$OMe | H |
| 3-96 | Me | SO$_2$(CH$_2$)$_2$OMe | H |
| 3-97 | Me | F | F |
| 3-98 | Me | F | Cl |
| 3-99 | Me | SEt | F |
| 3-100 | Me | SOEt | F |
| 3-101 | Me | SO$_2$Et | F |
| 3-102 | Me | Me | Cl |
| 3-103 | Me | F | Cl |
| 3-104 | Me | Cl | Cl |
| 3-105 | Me | NH$_2$ | Cl |
| 3-106 | Me | NHMe | Cl |
| 3-107 | Me | NMe$_2$ | Cl |
| 3-108 | Me | O(CH$_2$)$_2$OMe | Cl |
| 3-109 | Me | O(CH$_2$)$_3$OMe | Cl |
| 3-110 | Me | O(CH$_2$)$_4$OMe | Cl |
| 3-111 | Me | OCH$_2$CONMe$_2$ | Cl |
| 3-112 | Me | O(CH$_2$)$_2$—CONMe$_2$ | Cl |
| 3-113 | Me | O(CH$_2$)$_2$—NH(CO)NMe$_2$ | Cl |
| 3-114 | Me | O(CH$_2$)$_2$—NH(CO)NHCO$_2$Et | Cl |
| 3-115 | Me | O(CH$_2$)$_2$NHCO$_2$Me | Cl |
| 3-116 | Me | OCH$_2$NHSO$_2$cPr | Cl |
| 3-117 | Me | O(CH$_2$)-5-2,4-di-methyl-2,4-dihydro-3H-1,2,4-triazol-3-on | Cl |
| 3-118 | Me | O(CH$_2$)-3,5-dime-thyl-1,2-oxazol-4-yl | Cl |
| 3-119 | Me | SMe | Cl |
| 3-120 | Me | SOMe | Cl |
| 3-121 | Me | SO$_2$Me | Cl |
| 3-122 | Me | SEt | Cl |
| 3-123 | Me | SOEt | Cl |
| 3-124 | Me | SO$_2$Et | Cl |
| 3-125 | Me | S(CH$_2$)$_2$OMe | Cl |
| 3-126 | Me | SO(CH$_2$)$_2$OMe | Cl |
| 3-127 | Me | SO$_2$(CH$_2$)$_2$OMe | Cl |
| 3-128 | Me | NH$_2$ | Br |
| 3-129 | Me | NHMe | Br |
| 3-130 | Me | NMe$_2$ | Br |
| 3-131 | Me | OCH$_2$CONMe$_2$ | Br |
| 3-132 | Me | O(CH$_2$)-5-pyrrolidin-2-on | Br |
| 3-133 | Me | SMe | Br |
| 3-134 | Me | SOMe | Br |
| 3-135 | Me | SO$_2$Me | Br |
| 3-136 | Me | SEt | Br |
| 3-137 | Me | SOEt | Br |
| 3-138 | Me | SO$_2$Et | Br |
| 3-139 | Me | SMe | I |
| 3-140 | Me | SOMe | I |
| 3-141 | Me | SO$_2$Me | I |
| 3-142 | Me | SEt | I |
| 3-143 | Me | SOEt | I |
| 3-144 | Me | SO$_2$Et | I |
| 3-145 | Me | Cl | CF$_3$ |
| 3-146 | Me | SMe | CF$_3$ |
| 3-147 | Me | SOMe | CF$_3$ |
| 3-148 | Me | SO$_2$Me | CF$_3$ |
| 3-149 | Me | SEt | CF$_3$ |
| 3-150 | Me | SOEt | CF$_3$ |
| 3-151 | Me | SO$_2$Et | CF$_3$ |
| 3-152 | Me | S(CH$_2$)$_2$OMe | CF$_3$ |
| 3-153 | Me | SO(CH$_2$)$_2$OMe | CF$_3$ |
| 3-154 | Me | SO$_2$(CH$_2$)$_2$OMe | CF$_3$ |
| 3-155 | Me | Me | SO$_2$Me |
| 3-156 | Me | 4,5-dihydro-1,2-oxazol-3 yl | SO$_2$Me |
| 3-157 | Me | 4,5-dihydro-1,2-oxazol-3 yl | SO$_2$Et |
| 3-158 | Me | 5-cyanomethyl-4,5-dihydro-1,2-oxazol-3-yl | SO$_2$Me |
| 3-159 | Me | 5-cyanomethyl-4,5-dihydro-1,2-oxazol-3-yl | SO$_2$Et |
| 3-160 | Me | NH$_2$ | SO$_2$Me |
| 3-161 | Me | NHMe | SO$_2$Me |
| 3-162 | Me | NMe$_2$ | SO$_2$Me |
| 3-163 | Me | NH(CH$_2$)$_2$OMe | SO$_2$Me |
| 3-164 | Me | Pyrazol-1-yl | SO$_2$Me |
| 3-165 | Me | OH | SO$_2$Me |
| 3-166 | Me | OMe | SO$_2$Me |
| 3-167 | Me | OMe | SO$_2$Et |
| 3-168 | Me | OEt | SO$_2$Me |

TABLE 3-continued

Compounds of the general formula (I) according to the invention in which A is CY, B is CH and R is phenyl

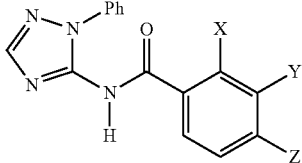
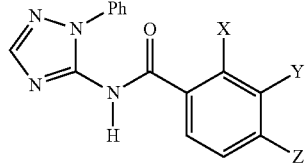

| No. | X | Y | Z |
|---|---|---|---|
| 3-169 | Me | OEt | SO₂Et |
| 3-170 | Me | OiPr | SO₂Me |
| 3-171 | Me | OiPr | SO₂Et |
| 3-172 | Me | O(CH₂)₂OMe | SO₂Me |
| 3-173 | Me | O(CH₂)₂OMe | SO₂Et |
| 3-174 | Me | O(CH₂)₃OMe | SO₂Me |
| 3-175 | Me | O(CH₂)₃OMe | SO₂Et |
| 3-176 | Me | O(CH₂)₄OMe | SO₂Me |
| 3-177 | Me | O(CH₂)₄OMe | SO₂Et |
| 3-178 | Me | O(CH₂)₂NHSO2Me | SO₂Me |
| 3-179 | Me | O(CH₂)₂NHSO2Me | SO₂Et |
| 3-180 | Me | OCH₂(CO)NMe₂ | SO₂Me |
| 3-181 | Me | OCH₂(CO)NMe₂ | SO₂Et |
| 3-182 | Me | [1,4]dioxan-2-yl-methoxy | SO₂Me |
| 3-183 | Me | [1,4]dioxan-2-yl-methoxy | SO₂Et |
| 3-184 | Me | O(CH₂)₂—O(3,5-dimethoxypyrimidin-2-yl | SO₂Me |
| 3-185 | Me | Cl | SO₂Me |
| 3-186 | Me | SMe | SO₂Me |
| 3-187 | Me | SOMe | SO₂Me |
| 3-188 | Me | SO₂Me | SO₂Me |
| 3-189 | Me | SO₂Me | SO₂Et |
| 3-190 | Me | SEt | SO₂Me |
| 3-191 | Me | SOEt | SO₂Me |
| 3-192 | Me | SO₂Et | SO₂Me |
| 3-193 | Me | S(CH₂)₂OMe | SO₂Me |
| 3-194 | Me | SO(CH₂)₂OMe | SO₂Me |
| 3-195 | Me | SO₂(CH₂)₂OMe | SO2Me |
| 3-196 | CH₂SMe | OMe | SO₂Me |
| 3-197 | CH₂OMe | OMe | SO₂Me |
| 3-198 | CH₂O(CH₂)₂OMe | NH(CH₂)₂OEt | SO₂Me |
| 3-199 | CH₂O(CH₂)₂OMe | NH(CH₂)₃OEt | SO₂Me |
| 3-200 | CH₂O(CH₂)₃OMe | OMe | SO₂Me |
| 3-201 | CH₂O(CH₂)₂OMe | NH(CH₂)₂OMe | SO₂Me |
| 3-202 | CH₂O(CH₂)₂OMe | NH(CH₂)₃OMe | SO₂Me |
| 3-203 | Et | SMe | Cl |
| 3-204 | Et | SO₂Me | Cl |
| 3-205 | Et | SMe | CF₃ |
| 3-206 | Et | SO₂Me | CF₃ |
| 3-207 | Et | F | SO₂Me |
| 3-208 | Et | NH(CH₂)₂OMe | SO₂Me |
| 3-209 | iPr | SO₂Me | CF₃ |
| 3-210 | cPr | SO₂Me | CF₃ |
| 3-211 | CF₃ | O(CH₂)₂OMe | F |
| 3-212 | CF₃ | O(CH₂)₃OMe | F |
| 3-213 | CF₃ | OCH₂CONMe₂ | F |
| 3-214 | CF₃ | [1,4]dioxan-2-yl-methoxy | F |
| 3-215 | CF₃ | O(CH₂)₂OMe | Cl |
| 3-216 | CF₃ | O(CH₂)₃OMe | Cl |
| 3-217 | CF₃ | OCH₂CONMe₂ | Cl |
| 3-218 | CF₃ | [1,4]dioxan-2-yl-methoxy | Cl |
| 3-219 | CF₃ | O(CH₂)₂OMe | Br |
| 3-220 | CF₃ | O(CH₂)₃OMe | Br |
| 3-221 | CF₃ | OCH₂CONMe₂ | Br |
| 3-222 | CF₃ | [1,4]dioxan-2-yl-methoxy | Br |
| 3-223 | CF₃ | O(CH₂)₂OMe | I |
| 3-224 | CF₃ | O(CH₂)₃OMe | I |
| 3-225 | CF₃ | OCH₂CONMe₂ | I |
| 3-226 | CF₃ | [1,4]dioxan-2-yl-methoxy | I |
| 3-227 | CF₃ | F | SO₂Me |
| 3-228 | CF₃ | F | SO₂Et |
| 3-229 | CF₃ | O(CH₂)₂OMe | SO₂Me |
| 3-230 | CF₃ | O(CH₂)₂OMe | SO₂Et |
| 3-231 | CF₃ | O(CH₂)₃OMe | SO₂Me |
| 3-232 | CF₃ | O(CH₂)₃OMe | SO₂Et |
| 3-233 | CF₃ | OCH₂CONMe₂ | SO₂Me |
| 3-234 | CF₃ | OCH₂CONMe₂ | SO₂Et |
| 3-235 | CF₃ | [1,4]dioxan-2-yl-methoxy | SO₂Me |
| 3-236 | CF₃ | [1,4]dioxan-2-yl-methoxy | SO₂Et |
| 3-237 | F | SMe | CF₃ |
| 3-238 | F | SOMe | CF₃ |
| 3-239 | Cl | Me | Cl |
| 3-240 | Cl | OCH₂CHCH₂ | Cl |
| 3-241 | Cl | OCH₂CHF₂ | Cl |
| 3-242 | Cl | O(CH₂)₂OMe | Cl |
| 3-243 | Cl | OCH₂(CO)NMe₂ | Cl |
| 3-244 | Cl | O(CH₂)-5-pyrrolidin-2-on | Cl |
| 3-245 | Cl | SMe | Cl |
| 3-246 | Cl | SOMe | Cl |
| 3-247 | Cl | SO₂Me | Cl |
| 3-248 | Cl | F | SMe |
| 3-249 | Cl | Cl | SO₂Me |
| 3-250 | Cl | COOMe | SO₂Me |
| 3-251 | Cl | CONMe₂ | SO₂Me |
| 3-252 | Cl | CONMe(OMe) | SO₂Me |
| 3-253 | Cl | CH₂OMe | SO₂Me |
| 3-254 | Cl | CH₂OMe | SO₂Et |
| 3-255 | Cl | CH₂OEt | SO₂Me |
| 3-256 | Cl | CH₂OEt | SO₂Et |
| 3-257 | Cl | CH₂OCH₂CHF₂ | SO₂Me |
| 3-258 | Cl | CH₂OCH₂CF₃ | SO₂Me |
| 3-259 | Cl | CH₂OCH₂CF₃ | SO₂Et |
| 3-260 | Cl | CH₂OCH₂CF₂CHF₂ | SO₂Me |
| 3-261 | Cl | CH₂OcPentyl | SO₂Me |
| 3-262 | Cl | CH₂PO(OMe)₂ | SO₂Me |
| 3-263 | Cl | 4,5-dihydro-1,2-oxazol-3 yl | SMe |
| 3-264 | Cl | 4,5-dihydro-1,2-oxazol-3 yl | SO₂Me |
| 3-265 | Cl | 4,5-dihydro-1,2-oxazol-3 yl | SO₂Et |
| 3-266 | Cl | 5-cyanomethyl-4,5-dihydro-1,2-oxazol-3 yl | SO₂Me |
| 3-267 | Cl | 5-cyanomethyl-4,5-dihydro-1,2-oxazol-3 yl | SO₂Et |
| 3-268 | Cl | 5-(Methoxymethyl)-4,5-dihydro-1,2-oxazol-3 yl | SO₂Et |
| 3-269 | Cl | 5-(Methoxymethyl)-5-Methyl-4,5-dihy-dro-1,2-oxazol-3-yl | SO₂Et |
| 3-270 | Cl | CH₂O-tetrahydrofuran-3-yl | SO₂Me |
| 3-271 | Cl | CH₂O-tetrahydrofuran-3-yl | SO₂Et |
| 3-272 | Cl | CH₂OCH₂-tetrahydrofuran-2-yl | SO₂Me |
| 3-273 | Cl | CH₂OCH₂-tetrahydrofuran-2-yl | SO₂Et |
| 3-274 | Cl | CH₂OCH₂-tetrahydrofuran-3-yl | SO₂Me |
| 3-275 | Cl | CH₂OCH₂-tetrahydrofuran-3-yl | SO₂Et |
| 3-276 | Cl | OMe | SO₂Me |
| 3-277 | Cl | OMe | SO₂Et |
| 3-278 | Cl | OEt | SO₂Me |
| 3-279 | Cl | OEt | SO₂Et |
| 3-280 | Cl | OiPr | SO₂Me |
| 3-281 | Cl | OiPr | SO₂Et |
| 3-282 | Cl | O(CH₂)₂OMe | SO₂Me |
| 3-283 | Cl | O(CH₂)₄OMe | SO₂Me |
| 3-284 | Cl | O(CH₂)₄OMe | SO₂Et |
| 3-285 | Cl | O(CH₂)₃OMe | SO₂Me |
| 3-286 | Cl | O(CH₂)₃OMe | SO₂Et |
| 3-287 | Cl | O(CH₂)₂OMe | SO₂Me |
| 3-288 | Cl | O(CH₂)₂OMe | SO₂Et |
| 3-289 | Cl | [1,4]dioxan-2-yl-methoxy | SO₂Me |
| 3-290 | Cl | [1,4]dioxan-2-yl-methoxy | SO₂Et |
| 3-291 | Cl | OCH₂(CO)NMe₂ | SO₂Me |

TABLE 3-continued

Compounds of the general formula (I) according to the invention in which A is CY, B is CH and R is phenyl

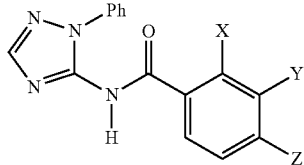

| No. | X | Y | Z |
|---|---|---|---|
| 3-292 | Cl | OCH₂(CO)NMe₂ | SO₂Et |
| 3-293 | Cl | SMe | SO₂Me |
| 3-294 | Cl | SOMe | SO₂Me |
| 3-295 | Br | OMe | Br |
| 3-296 | Br | O(CH₂)₂OMe | Br |
| 3-297 | Br | O(CH₂)₂OMe | SO₂Me |
| 3-298 | Br | O(CH₂)₂OMe | SO₂Et |
| 3-299 | Br | O(CH₂)₃OMe | SO₂Me |
| 3-300 | Br | O(CH₂)₃OMe | SO₂Et |
| 3-301 | Br | O(CH₂)₄OMe | SO₂Me |
| 3-302 | Br | O(CH₂)₄OMe | SO₂Et |
| 3-303 | Br | [1,4]dioxan-2-yl-methoxy | SO₂Me |
| 3-304 | Br | [1,4]dioxan-2-yl-methoxy | SO₂Et |
| 3-305 | I | O(CH₂)₂OMe | SO₂Me |
| 3-306 | I | O(CH₂)₂OMe | SO₂Et |
| 3-307 | I | O(CH₂)₃OMe | SO₂Me |
| 3-308 | I | O(CH₂)₃OMe | SO₂Et |
| 3-309 | I | O(CH₂)₄OMe | SO₂Me |
| 3-310 | I | O(CH₂)₄OMe | SO₂Et |
| 3-311 | I | [1,4]dioxan-2-yl-methoxy | SO₂Me |
| 3-312 | I | [1,4]dioxan-2-yl-methoxy | SO₂Et |
| 3-313 | OMe | SMe | CF₃ |
| 3-314 | OMe | SOMe | CF₃ |
| 3-315 | OMe | SO₂Me | CF₃ |
| 3-316 | OMe | SOEt | CF₃ |
| 3-317 | OMe | SO₂Et | CF₃ |
| 3-318 | OMe | S(CH₂)₂OMe | CF₃ |
| 3-319 | OMe | SO(CH₂)₂OMe | CF₃ |
| 3-320 | OMe | SO₂(CH₂)₂OMe | CF₃ |
| 3-321 | OMe | SMe | Cl |
| 3-322 | OMe | SOMe | Cl |
| 3-323 | OMe | SO₂Me | Cl |
| 3-324 | OMe | SEt | Cl |
| 3-325 | OMe | SOEt | Cl |
| 3-326 | OMe | SO2Et | Cl |
| 3-327 | OMe | S(CH₂)₂OMe | Cl |
| 3-328 | OMe | SO(CH₂)₂OMe | Cl |
| 3-329 | OMe | SO₂(CH₂)₂OMe | Cl |
| 3-330 | OCH₂c-Pr | SMe | CF₃ |
| 3-331 | OCH₂c-Pr | SOMe | CF₃ |
| 3-332 | OCH₂c-Pr | SO₂Me | CF₃ |
| 3-333 | OCH₂c-Pr | SEt | CF₃ |
| 3-334 | OCH₂c-Pr | SOEt | CF₃ |
| 3-335 | OCH₂c-Pr | SO₂Et | CF₃ |
| 3-336 | OCH₂c-Pr | S(CH₂)₂OMe | CF₃ |
| 3-337 | OCH₂c-Pr | SO(CH₂)₂OMe | CF₃ |
| 3-338 | OCH₂c-Pr | SO₂(CH₂)₂OMe | CF₃ |
| 3-339 | OCH₂c-Pr | SMe | Cl |
| 3-340 | OCH₂c-Pr | SOMe | Cl |
| 3-341 | OCH₂c-Pr | SO₂Me | Cl |
| 3-342 | OCH₂c-Pr | SEt | Cl |
| 3-343 | OCH₂c-Pr | SOEt | Cl |
| 3-344 | OCH₂c-Pr | SO₂Et | Cl |
| 3-345 | OCH₂c-Pr | S(CH₂)₂OMe | Cl |
| 3-346 | OCH₂c-Pr | SO(CH₂)₂OMe | Cl |
| 3-347 | OCH₂c-Pr | SO₂(CH₂)₂OMe | Cl |
| 3-348 | OCH₂c-Pr | SMe | SO₂Me |
| 3-349 | OCH₂c-Pr | SOMe | SO₂Me |
| 3-350 | OCH₂c-Pr | SO₂Me | SO₂Me |
| 3-351 | OCH₂c-Pr | SEt | SO₂Me |
| 3-352 | OCH₂c-Pr | SOEt | SO₂Me |
| 3-353 | OCH₂c-Pr | SO₂Et | SO₂Me |
| 3-354 | OCH₂c-Pr | S(CH₂)₂OMe | SO₂Me |
| 3-355 | OCH₂c-Pr | SO(CH₂)₂OMe | SO₂Me |
| 3-356 | OCH₂c-Pr | SO₂(CH₂)₂OMe | SO₂Me |
| 3-357 | SO₂Me | F | CF₃ |

TABLE 3-continued

Compounds of the general formula (I) according to the invention in which A is CY, B is CH and R is phenyl

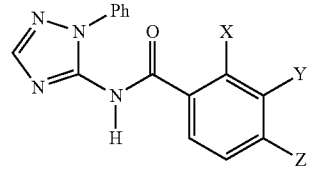

| No. | X | Y | Z |
|---|---|---|---|
| 3-358 | SO₂Me | NH₂ | CF₃ |
| 3-359 | SO₂Me | NHEt | Cl |
| 3-360 | SMe | SEt | F |
| 3-361 | SMe | SMe | F |

TABLE 4

Compounds of the general formula (I) according to the invention in which A is CY, B is N and R is methyl

| No. | X | Y | Z |
|---|---|---|---|
| 4-1 | F | H | Cl |
| 4-2 | F | H | Br |
| 4-3 | F | H | SO₂Me |
| 4-4 | F | H | SO₂Et |
| 4-5 | F | H | CF₃ |
| 4-6 | Cl | H | F |
| 4-7 | Cl | H | Cl |
| 4-8 | Cl | H | Br |
| 4-9 | Cl | H | SMe |
| 4-10 | Cl | H | SO₂Me |
| 4-11 | Cl | H | SO₂CH₂Cl |
| 4-12 | Cl | H | SEt |
| 4-13 | Cl | H | SO₂Et |
| 4-14 | Cl | H | CF₃ |
| 4-15 | Br | H | Cl |
| 4-16 | Br | H | Br |
| 4-17 | Br | H | SO₂Me |
| 4-18 | Br | H | SO₂Et |
| 4-19 | Br | H | CF₃ |
| 4-20 | SO₂Me | H | Cl |
| 4-21 | SO₂Me | H | Br |
| 4-22 | SO₂Me | H | SMe |
| 4-23 | SO₂Me | H | SOMe |
| 4-24 | SO₂Me | H | SO₂Me |
| 4-25 | SO₂Me | H | CF₃ |
| 4-26 | SO₂Et | H | Cl |
| 4-27 | SO₂Et | H | Br |
| 4-28 | SO₂Et | H | SMe |
| 4-29 | SO₂Et | H | SOMe |
| 4-30 | SO₂Et | H | SO₂Me |
| 4-31 | SO₂Et | H | CF₃ |
| 4-32 | NO₂ | H | F |
| 4-33 | NO₂ | H | Cl |
| 4-34 | NO₂ | H | Br |
| 4-35 | NO₂ | H | I |
| 4-36 | NO₂ | H | CN |
| 4-37 | NO₂ | H | SO₂Me |
| 4-38 | NO₂ | H | SO₂Et |
| 4-39 | NO₂ | H | CF₃ |
| 4-40 | Me | H | Cl |
| 4-41 | Me | H | Br |
| 4-42 | Me | H | SO₂Me |

TABLE 4-continued

Compounds of the general formula (I) according to the invention in which A is CY, B is N and R is methyl

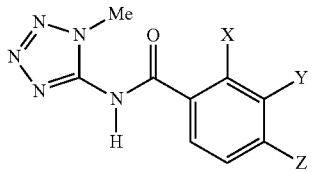 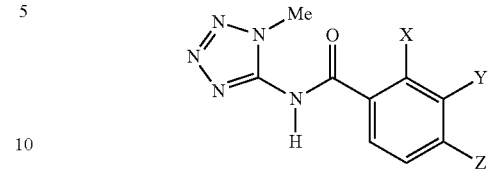

| No. | X | Y | Z |
|---|---|---|---|
| 4-43 | Me | H | SO₂CH₂Cl |
| 4-44 | Me | H | SO₂Et |
| 4-45 | Me | H | CF₃ |
| 4-46 | CH₂SO₂Me | H | CF₃ |
| 4-47 | Et | H | Cl |
| 4-48 | Et | H | Br |
| 4-49 | Et | H | SO₂Me |
| 4-50 | Et | H | SO₂CH₂Cl |
| 4-51 | Et | H | SEt |
| 4-52 | Et | H | SO₂Et |
| 4-53 | Et | H | CF₃ |
| 4-54 | CF₃ | H | Cl |
| 4-55 | CF₃ | H | Br |
| 4-56 | CF₃ | H | SO₂Me |
| 4-57 | CF₃ | H | CF₃ |
| 4-58 | NO₂ | NH₂ | F |
| 4-59 | NO₂ | NHMe | F |
| 4-60 | NO₂ | NMe₂ | F |
| 4-61 | NO₂ | Me | Cl |
| 4-62 | NO₂ | NH₂ | Cl |
| 4-63 | NO₂ | NHMe | Cl |
| 4-64 | NO₂ | NMe₂ | Cl |
| 4-65 | NO₂ | NH₂ | Br |
| 4-66 | NO₂ | NHMe | Br |
| 4-67 | NO₂ | NMe₂ | Br |
| 4-68 | NO₂ | NH₂ | CF₃ |
| 4-69 | NO₂ | NMe₂ | CF₃ |
| 4-70 | NO₂ | NH₂ | SO₂Me |
| 4-71 | NO₂ | NH₂ | SO₂Et |
| 4-72 | NO₂ | NHMe | SO₂Me |
| 4-73 | NO₂ | NMe₂ | SO₂Me |
| 4-74 | NO₂ | NMe₂ | SO₂Et |
| 4-75 | NO₂ | NH₂ | 1H-1,2,4-triazol-1-yl |
| 4-76 | NO₂ | NHMe | 1H-1,2,4-triazol-1-yl |
| 4-77 | NO₂ | NMe₂ | 1H-1,2,4-triazol-1-yl |
| 4-78 | Me | SMe | H |
| 4-79 | Me | SOMe | H |
| 4-80 | Me | SO₂Me | H |
| 4-81 | Me | SEt | H |
| 4-82 | Me | SOEt | H |
| 4-83 | Me | SO₂Et | H |
| 4-84 | Me | S(CH₂)₂OMe | H |
| 4-85 | Me | SO(CH₂)₂OMe | H |
| 4-86 | Me | SO₂(CH₂)₂OMe | H |
| 4-87 | Me | F | F |
| 4-88 | Me | SEt | F |
| 4-89 | Me | SOEt | F |
| 4-90 | Me | SO₂Et | F |
| 4-91 | Me | Me | Cl |
| 4-92 | Me | F | Cl |
| 4-93 | Me | Cl | Cl |
| 4-94 | Me | NH₂ | Cl |
| 4-95 | Me | NHMe | Cl |
| 4-96 | Me | NMe₂ | Cl |
| 4-97 | Me | O(CH₂)₂OMe | Cl |
| 4-98 | Me | O(CH₂)₃OMe | Cl |
| 4-99 | Me | O(CH₂)₄OMe | Cl |
| 4-100 | Me | OCH₂CONMe₂ | Cl |
| 4-101 | Me | O(CH₂)2CONMe₂ | Cl |
| 4-102 | Me | O(CH₂)₂—NH(CO)NMe₂ | Cl |
| 4-103 | Me | O(CH₂)₂NH(CO)NHCO₂Et | Cl |
| 4-104 | Me | O(CH₂)₂NHCO₂Me | Cl |
| 4-105 | Me | OCH₂NHSO₂cPr | Cl |
| 4-106 | Me | O(CH₂)-5-(2,4-dimethyl-2,4-dihydro)-3H-1,2,4-triazol-3-on | Cl |
| 4-107 | Me | O(CH₂)-3,5-dimethyl-1,2-oxazol-4-yl | Cl |
| 4-108 | Me | SMe | Cl |
| 4-109 | Me | SOMe | Cl |
| 4-110 | Me | SO₂Me | Cl |
| 4-111 | Me | SEt | Cl |
| 4-112 | Me | SOEt | Cl |
| 4-113 | Me | SO₂Et | Cl |
| 4-114 | Me | S(CH₂)₂OMe | Cl |
| 4-115 | Me | SO(CH₂)₂OMe | Cl |
| 4-116 | Me | SO₂(CH₂)₂OMe | Cl |
| 4-117 | Me | NH₂ | Br |
| 4-118 | Me | NHMe | Br |
| 4-119 | Me | NMe₂ | Br |
| 4-120 | Me | OCH₂CONEt₂ | Br |
| 4-121 | Me | O(CH₂)-5-pyrrolidin-2-on | Br |
| 4-122 | Me | SMe | Br |
| 4-123 | Me | SOMe | Br |
| 4-124 | Me | SO₂Me | Br |
| 4-125 | Me | SEt | Br |
| 4-126 | Me | SOEt | Br |
| 4-127 | Me | SO₂Et | Br |
| 4-128 | Me | SMe | I |
| 4-129 | Me | SOMe | I |
| 4-130 | Me | SO₂Me | I |
| 4-131 | Me | SEt | I |
| 4-132 | Me | SOEt | I |
| 4-133 | Me | SO₂Et | I |
| 4-134 | Me | Cl | CF₃ |
| 4-135 | Me | SMe | CF₃ |
| 4-136 | Me | SOMe | CF₃ |
| 4-137 | Me | SO₂Me | CF₃ |
| 4-138 | Me | SEt | CF₃ |
| 4-139 | Me | SOEt | CF₃ |
| 4-140 | Me | SO₂Et | CF₃ |
| 4-141 | Me | S(CH₂)₂OMe | CF₃ |
| 4-142 | Me | S(O)(CH₂)₂OMe | CF₃ |
| 4-143 | Me | SO₂(CH₂)₂OMe | CF₃ |
| 4-144 | Me | 4,5-dihydro-1,2-oxazol-3 yl | SO₂Me |
| 4-145 | Me | 4,5-dihydro-1,2-oxazol-3 yl | SO₂Et |
| 4-146 | Me | 5-cyanomethyl-4,5-dihydro-1,2-oxazol-3-yl | SO₂Me |
| 4-147 | Me | 5-cyanomethyl-4,5-dihydro-1,2-oxazol-3-yl | SO₂Et |
| 4-148 | Me | NH₂ | SO₂Me |
| 4-149 | Me | NHMe | SO₂Me |
| 4-150 | Me | NMe₂ | SO₂Me |
| 4-151 | Me | NH(CH₂)₂OMe | SO₂Me |
| 4-152 | Me | Pyrazol-1-yl | SO₂Me |
| 4-153 | Me | OH | SO₂Me |
| 4-154 | Me | OMe | SO₂Me |
| 4-155 | Me | OMe | SO₂Et |
| 4-156 | Me | OEt | SO₂Me |
| 4-157 | Me | OEt | SO₂Et |
| 4-158 | Me | OiPr | SO₂Me |
| 4-159 | Me | OiPr | SO₂Et |
| 4-160 | Me | O(CH₂)₂OMe | SO₂Me |
| 4-161 | Me | O(CH₂)₂OMe | SO₂Et |
| 4-162 | Me | O(CH₂)₃OMe | SO₂Me |
| 4-163 | Me | O(CH₂)₃OMe | SO₂Et |
| 4-164 | Me | O(CH₂)₄OMe | SO₂Me |
| 4-165 | Me | O(CH₂)₄OMe | SO₂Et |
| 4-166 | Me | O(CH₂)₂NHSO2Me | SO₂Me |

TABLE 4-continued

Compounds of the general formula (I) according to the invention in which A is CY, B is N and R is methyl

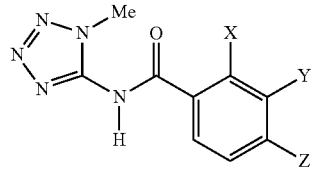

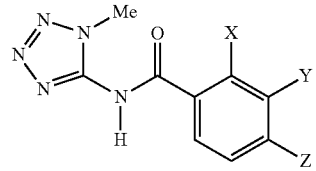

| No. | X | Y | Z |
|---|---|---|---|
| 4-167 | Me | O(CH$_2$)$_2$NHSO2Me | SO$_2$Et |
| 4-168 | Me | OCH$_2$(CO)NMe$_2$ | SO$_2$Me |
| 4-169 | Me | OCH$_2$(CO)NMe$_2$ | SO$_2$Et |
| 4-170 | Me | [1,4]dioxan-2-yl-methoxy | SO$_2$Me |
| 4-171 | Me | [1,4]dioxan-2-yl-methoxy | SO$_2$Et |
| 4-172 | Me | O(CH$_2$)$_2$—O(3,5-di-methoxypyrimidin-2-yl | SO$_2$Me |
| 4-173 | Me | Cl | SO$_2$Me |
| 4-174 | Me | SMe | SO$_2$Me |
| 4-175 | Me | SOMe | SO$_2$Me |
| 4-176 | Me | SO$_2$Me | SO$_2$Me |
| 4-177 | Me | SO$_2$Me | SO$_2$Et |
| 4-178 | Me | SEt | SO$_2$Me |
| 4-179 | Me | SOEt | SO$_2$Me |
| 4-180 | Me | SO$_2$Et | SO$_2$Me |
| 4-181 | Me | S(CH$_2$)$_2$OMe | SO$_2$Me |
| 4-182 | Me | SO(CH$_2$)$_2$OMe | SO$_2$Me |
| 4-183 | Me | SO$_2$(CH$_2$)$_2$OMe | SO$_2$Me |
| 4-184 | CH$_2$SMe | OMe | SO$_2$Me |
| 4-185 | CH$_2$OMe | OMe | SO$_2$Me |
| 4-186 | CH$_2$O(CH$_2$)$_2$OMe | NH(CH$_2$)$_2$OEt | SO$_2$Me |
| 4-187 | CH$_2$O(CH$_2$)$_2$OMe | NH(CH$_2$)$_3$OEt | SO$_2$Me |
| 4-188 | CH$_2$O(CH$_2$)$_3$OMe | OMe | SO$_2$Me |
| 4-189 | CH$_2$O(CH$_2$)$_2$OMe | NH(CH$_2$)$_2$OMe | SO$_2$Me |
| 4-190 | CH$_2$O(CH$_2$)$_2$OMe | NH(CH$_2$)$_3$OMe | SO$_2$Me |
| 4-191 | Et | SMe | Cl |
| 4-192 | Et | SO$_2$Me | Cl |
| 4-193 | Et | SMe | CF$_3$ |
| 4-194 | Et | SO$_2$Me | CF$_3$ |
| 4-195 | Et | F | SO$_2$Me |
| 4-196 | Et | NH(CH$_2$)$_2$OMe | SO$_2$Me |
| 4-197 | iPr | SMe | CF$_3$ |
| 4-198 | iPr | SO$_2$Me | CF$_3$ |
| 4-199 | cPr | SO$_2$Me | CF$_3$ |
| 4-200 | CF$_3$ | O(CH$_2$)$_2$OMe | F |
| 4-201 | CF$_3$ | O(CH$_2$)$_3$OMe | F |
| 4-202 | CF$_3$ | OCH$_2$CONMe$_2$ | F |
| 4-203 | CF$_3$ | [1,4]dioxan-2-yl-methoxy | F |
| 4-204 | CF$_3$ | O(CH$_2$)$_2$OMe | Cl |
| 4-205 | CF$_3$ | O(CH$_2$)$_3$OMe | Cl |
| 4-206 | CF$_3$ | OCH$_2$CONMe$_2$ | Cl |
| 4-207 | CF$_3$ | [1,4]dioxan-2-yl-methoxy | Cl |
| 4-208 | CF$_3$ | O(CH$_2$)$_2$OMe | Br |
| 4-209 | CF$_3$ | O(CH$_2$)$_3$OMe | Br |
| 4-210 | CF$_3$ | O(CH$_2$)$_3$OMe | Br |
| 4-211 | CF$_3$ | OCH$_2$CONMe$_2$ | Br |
| 4-212 | CF$_3$ | [1,4]dioxan-2-yl-methoxy | Br |
| 4-213 | CF$_3$ | O(CH$_2$)$_2$OMe | I |
| 4-214 | CF$_3$ | O(CH$_2$)$_3$OMe | I |
| 4-215 | CF$_3$ | OCH$_2$CONMe$_2$ | I |
| 4-216 | CF$_3$ | [1,4]dioxan-2-yl-methoxy | I |
| 4-217 | CF$_3$ | F | SO$_2$Me |
| 4-218 | CF$_3$ | F | SO$_2$Et |
| 4-219 | CF$_3$ | O(CH$_2$)$_2$OMe | SO$_2$Me |
| 4-220 | CF$_3$ | O(CH$_2$)$_2$OMe | SO$_2$Et |
| 4-221 | CF$_3$ | O(CH$_2$)$_3$OMe | SO$_2$Me |
| 4-222 | CF$_3$ | O(CH$_2$)$_3$OMe | SO$_2$Et |
| 4-223 | CF$_3$ | OCH$_2$CONMe$_2$ | SO$_2$Me |
| 4-224 | CF$_3$ | OCH$_2$CONMe$_2$ | SO$_2$Et |
| 4-225 | CF$_3$ | [1,4]dioxan-2-yl-methoxy | SO$_2$Me |
| 4-226 | CF$_3$ | [1,4]dioxan-2-yl-methoxy | SO$_2$Et |
| 4-227 | F | SMe | CF$_3$ |
| 4-228 | F | SOMe | CF$_3$ |
| 4-229 | Cl | SMe | H |
| 4-230 | Cl | SOMe | H |
| 4-231 | Cl | SO$_2$Me | H |
| 4-232 | Cl | SEt | H |
| 4-233 | Cl | SOEt | H |
| 4-234 | Cl | SO$_2$Et | H |
| 4-235 | Cl | S(CH$_2$)$_2$OMe | H |
| 4-236 | Cl | SO(CH$_2$)$_2$OMe | H |
| 4-237 | Cl | SO$_2$(CH$_2$)$_2$OMe | H |
| 4-238 | Cl | Me | Cl |
| 4-239 | Cl | Cl | Cl |
| 4-240 | Cl | OCH$_2$CHCH$_2$ | Cl |
| 4-241 | Cl | OCH$_2$CHF$_2$ | Cl |
| 4-242 | Cl | O(CH$_2$)$_2$OMe | Cl |
| 4-243 | Cl | OCH$_2$(CO)NMe$_2$ | Cl |
| 4-244 | Cl | O(CH$_2$)-5-pyrrolidin-2-on | Cl |
| 4-245 | Cl | SMe | Cl |
| 4-246 | Cl | SOMe | Cl |
| 4-247 | Cl | SO$_2$Me | Cl |
| 4-248 | Cl | F | SMe |
| 4-249 | Cl | Cl | SO$_2$Me |
| 4-250 | Cl | COOMe | SO$_2$Me |
| 4-251 | Cl | CONMe$_2$ | SO$_2$Me |
| 4-252 | Cl | CONMe(OMe) | SO$_2$Me |
| 4-253 | Cl | CH$_2$OMe | SO$_2$Me |
| 4-254 | Cl | CH$_2$OMe | SO$_2$Et |
| 4-255 | Cl | CH$_2$OEt | SO$_2$Me |
| 4-256 | Cl | CH$_2$OEt | SO$_2$Et |
| 4-257 | Cl | CH$_2$OiPr | SO$_2$Me |
| 4-258 | Cl | CH$_2$OcPentyl | SO$_2$Me |
| 4-259 | Cl | CH$_2$OCH$_2$CHF$_2$ | SO$_2$Me |
| 4-260 | Cl | CH$_2$OCH$_2$CF$_3$ | SO$_2$Me |
| 4-261 | Cl | CH$_2$OCH$_2$CF$_3$ | SO$_2$Et |
| 4-262 | Cl | CH$_2$OCH$_2$CF$_2$CHF$_2$ | SO$_2$Me |
| 4-263 | Cl | CH$_2$PO$_3$Me$_2$ | SO$_2$Me |
| 4-264 | Cl | 4,5-dihydro-1,2-oxazol-3 y | SMe |
| 4-265 | Cl | 4,5-dihydro-1,2-oxazol-3 yl | SO$_2$Me |
| 4-266 | Cl | 4,5-dihydro-1,2-oxazol-3 yl | SO$_2$Et |
| 4-267 | Cl | 5-cyanomethyl-4,5-dihydro-1,2-oxazol-3 yl | SO$_2$Me |
| 4-268 | Cl | 5-cyanomethyl-4,5-dihydro-1,2-oxazol-3 yl | SO$_2$Et |
| 4-269 | Cl | CH$_2$O-tetrahydro-furan-3-yl | SO$_2$Me |
| 4-270 | Cl | CH$_2$O-tetrahydro-furan-3-yl | SO$_2$Et |
| 4-271 | Cl | CH$_2$OCH$_2$-tetrahydrofuran-2-yl | SO$_2$Me |
| 4-272 | Cl | CH$_2$OCH$_2$-tetrahydrofuran-2-yl | SO$_2$Et |
| 4-273 | Cl | CH$_2$OCH$_2$-tetrahydrofuran-3-yl | SO$_2$Me |
| 4-274 | Cl | CH$_2$OCH$_2$-tetrahydrofuran-3-yl | SO$_2$Et |
| 4-275 | Cl | pyrazol-1-yl | SO$_2$Me |
| 4-276 | Cl | OMe | SO$_2$Me |
| 4-277 | Cl | OMe | SO$_2$Et |
| 4-278 | Cl | OEt | SO$_2$Me |
| 4-279 | Cl | OEt | SO$_2$Et |
| 4-280 | Cl | OiPr | SO$_2$Me |
| 4-281 | Cl | OiPr | SO$_2$Et |
| 4-282 | Cl | O(CH$_2$)$_2$OMe | SO$_2$Me |
| 4-283 | Cl | O(CH$_2$)$_2$OMe | SO$_2$Et |
| 4-284 | Cl | O(CH$_2$)$_3$OMe | SO$_2$Me |
| 4-285 | Cl | O(CH$_2$)$_3$OMe | SO$_2$Et |
| 4-286 | Cl | O(CH$_2$)$_4$OMe | SO$_2$Me |
| 4-287 | Cl | O(CH$_2$)$_4$OMe | SO$_2$Et |
| 4-288 | Cl | [1,4]dioxan-2-yl-methoxy | SO$_2$Me |
| 4-289 | Cl | [1,4]dioxan-2-yl-methoxy | SO$_2$Et |
| 4-290 | Cl | OCH$_2$(CO)NMe$_2$ | SO$_2$Me |
| 4-291 | Cl | OCH$_2$(CO)NMe$_2$ | SO$_2$Et |

TABLE 4-continued

Compounds of the general formula (I) according to the invention in which A is CY, B is N and R is methyl

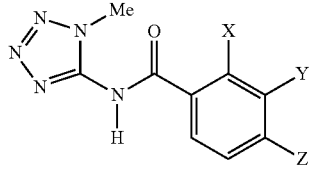

| No. | X | Y | Z |
|---|---|---|---|
| 4-292 | Cl | SMe | SO₂Me |
| 4-293 | Cl | SOMe | SO₂Me |
| 4-294 | Br | OMe | Br |
| 4-295 | Br | O(CH₂)₂OMe | Br |
| 4-296 | Br | O(CH₂)₂OMe | SO₂Me |
| 4-297 | Br | O(CH₂)₂OMe | SO₂Et |
| 4-298 | Br | O(CH₂)₃OMe | SO₂Me |
| 4-299 | Br | O(CH₂)₃OMe | SO₂Et |
| 4-300 | Br | O(CH₂)₄OMe | SO₂Me |
| 4-301 | Br | O(CH₂)₄OMe | SO₂Et |
| 4-302 | Br | [1,4]dioxan-2-yl-methoxy | SO₂Me |
| 4-303 | Br | [1,4]dioxan-2-yl-methoxy | SO₂Et |
| 4-304 | I | O(CH₂)₂OMe | SO₂Me |
| 4-305 | I | O(CH₂)₂OMe | SO₂Et |
| 4-306 | I | O(CH₂)₃OMe | SO₂Me |
| 4-307 | I | O(CH₂)₃OMe | SO₂Et |
| 4-308 | I | O(CH₂)₄OMe | SO₂Me |
| 4-309 | I | O(CH₂)₄OMe | SO₂Et |
| 4-310 | I | [1,4]dioxan-2-yl-methoxy | SO₂Me |
| 4-311 | I | [1,4]dioxan-2-yl-methoxy | SO₂Et |
| 4-312 | OMe | SMe | CF₃ |
| 4-313 | OMe | SOMe | CF₃ |
| 4-314 | OMe | SO₂Me | CF₃ |
| 4-315 | OMe | SEt | CF₃ |
| 4-316 | OMe | SOEt | CF₃ |
| 4-317 | OMe | SO₂Et | CF₃ |
| 4-318 | OMe | S(CH₂)₂OMe | CF₃ |
| 4-319 | OMe | SO(CH₂)₂OMe | CF₃ |
| 4-320 | OMe | SO₂(CH₂)₂OMe | CF₃ |
| 4-321 | OMe | SMe | Cl |
| 4-322 | OMe | SOMe | Cl |
| 4-323 | OMe | SO₂Me | Cl |
| 4-324 | OMe | SEt | Cl |
| 4-325 | OMe | SOEt | Cl |
| 4-326 | OMe | SO₂Et | Cl |
| 4-327 | OMe | S(CH₂)₂OMe | Cl |
| 4-328 | OMe | SO(CH₂)₂OMe | Cl |
| 4-329 | OMe | SO₂(CH₂)₂OMe | Cl |
| 4-330 | OCH₂c-Pr | SMe | CF₃ |
| 4-331 | OCH₂c-Pr | SOMe | CF₃ |
| 4-332 | OCH₂c-Pr | SO₂Me | CF₃ |
| 4-333 | OCH₂c-Pr | SEt | CF₃ |
| 4-334 | OCH₂c-Pr | SOEt | CF₃ |
| 4-335 | OCH₂c-Pr | SO₂Et | CF₃ |
| 4-336 | OCH₂c-Pr | S(CH₂)₂OMe | CF₃ |
| 4-337 | OCH₂c-Pr | SO(CH₂)₂OMe | CF₃ |
| 4-338 | OCH₂c-Pr | SO₂(CH₂)₂OMe | CF₃ |
| 4-339 | OCH₂c-Pr | SMe | Cl |
| 4-340 | OCH₂c-Pr | SOMe | Cl |
| 4-341 | OCH₂c-Pr | SO₂Me | Cl |
| 4-342 | OCH₂c-Pr | SEt | Cl |
| 4-343 | OCH₂c-Pr | SOEt | Cl |
| 4-344 | OCH₂c-Pr | SO₂Et | Cl |
| 4-345 | OCH₂c-Pr | S(CH₂)₂OMe | Cl |
| 4-346 | OCH₂c-Pr | SO(CH₂)₂OMe | Cl |
| 4-347 | OCH₂c-Pr | SO₂(CH₂)₂OMe | Cl |
| 4-348 | OCH₂c-Pr | SMe | SO₂Me |
| 4-349 | OCH₂c-Pr | SOMe | SO₂Me |
| 4-350 | OCH₂c-Pr | SO₂Me | SO₂Me |
| 4-351 | OCH₂c-Pr | SEt | SO₂Me |
| 4-352 | OCH₂c-Pr | SOEt | SO₂Me |
| 4-353 | OCH₂c-Pr | SO₂Et | SO₂Me |
| 4-354 | OCH₂c-Pr | S(CH₂)₂OMe | SO₂Me |
| 4-355 | OCH₂c-Pr | SO(CH₂)₂OMe | SO₂Me |
| 4-356 | OCH₂c-Pr | SO₂(CH₂)₂OMe | SO₂Me |
| 4-357 | SO₂Me | F | CF₃ |

TABLE 4-continued

Compounds of the general formula (I) according to the invention in which A is CY, B is N and R is methyl

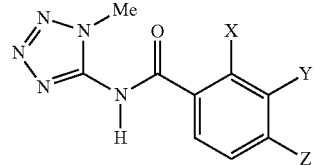

| No. | X | Y | Z |
|---|---|---|---|
| 4-358 | SO₂Me | NH₂ | CF₃ |
| 4-359 | SO₂Me | NHEt | Cl |
| 4-360 | SMe | SEt | F |
| 4-361 | SMe | SMe | F |

TABLE 5

Compounds of the general formula (I) according to the invention in which A is CY, B is N and R is ethyl

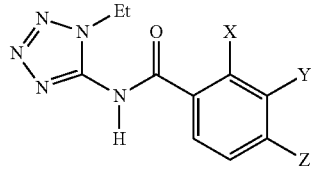

| No. | X | Y | Z |
|---|---|---|---|
| 5-1 | F | H | Cl |
| 5-2 | F | H | Br |
| 5-3 | F | H | SO₂Me |
| 5-4 | F | H | SO₂Et |
| 5-5 | F | H | CF₃ |
| 5-6 | F | H | NO₂ |
| 5-7 | Cl | H | F |
| 5-8 | Cl | H | Cl |
| 5-9 | Cl | H | Br |
| 5-10 | Cl | H | SMe |
| 5-11 | Cl | H | SOMe |
| 5-12 | Cl | H | SO₂Me |
| 5-13 | Cl | H | SO₂CH₂Cl |
| 5-14 | Cl | H | SEt |
| 5-15 | Cl | H | SO₂Et |
| 5-16 | Cl | H | CF₃ |
| 5-17 | Cl | H | NO₂ |
| 5-18 | Cl | H | pyrazol-1-yl |
| 5-19 | Cl | H | 1H-1,2,4-triazol-1-yl |
| 5-20 | Br | H | Cl |
| 5-21 | Br | H | Br |
| 5-22 | Br | H | SO₂Me |
| 5-23 | Br | H | SO₂Et |
| 5-24 | Br | H | CF₃ |
| 5-25 | SO₂Me | H | Cl |
| 5-26 | SO₂Me | H | Br |
| 5-27 | SO₂Me | H | SMe |
| 5-28 | SO₂Me | H | SOMe |
| 5-29 | SO₂Me | H | SO₂Me |
| 5-30 | SO₂Me | H | SO₂Et |
| 5-31 | SO₂Me | H | CF₃ |
| 5-32 | SO₂Et | H | Cl |
| 5-33 | SO₂Et | H | Br |
| 5-34 | SO₂Et | H | SMe |
| 5-35 | SO₂Et | H | SOMe |
| 5-36 | SO₂Et | H | SO₂Me |
| 5-37 | SO₂Et | H | CF₃ |
| 5-38 | NO₂ | H | F |
| 5-39 | NO₂ | H | Cl |
| 5-40 | NO₂ | H | Br |
| 5-41 | NO₂ | H | I |
| 5-42 | NO₂ | H | CN |

TABLE 5-continued

Compounds of the general formula (I) according to the invention in which A is CY, B is N and R is ethyl

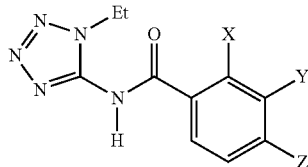 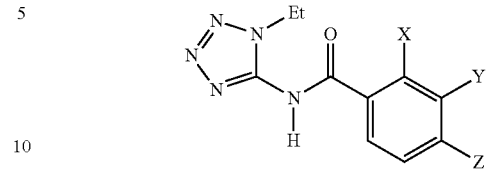

| No. | X | Y | Z |
|---|---|---|---|
| 5-43 | NO₂ | H | SO₂Me |
| 5-44 | NO₂ | H | SO₂Et |
| 5-45 | NO₂ | H | CF₃ |
| 5-46 | Me | H | Cl |
| 5-47 | Me | H | Br |
| 5-48 | Me | H | SMe |
| 5-49 | Me | H | SO₂Me |
| 5-50 | Me | H | SO₂CH₂Cl |
| 5-51 | Me | H | SEt |
| 5-52 | Me | H | SO₂Et |
| 5-53 | Me | H | CF₃ |
| 5-54 | CH₂SO₂Me | H | CF₃ |
| 5-55 | Et | H | Cl |
| 5-56 | Et | H | Br |
| 5-57 | Et | H | SMe |
| 5-58 | Et | H | SO₂Me |
| 5-59 | Et | H | SO₂CH₂Cl |
| 5-60 | Et | H | SEt |
| 5-61 | Et | H | SO₂Et |
| 5-62 | Et | H | CF₃ |
| 5-63 | CF₃ | H | Cl |
| 5-64 | CF₃ | H | Br |
| 5-65 | CF₃ | H | SO₂Me |
| 5-66 | CF₃ | H | SO₂Et |
| 5-67 | CF₃ | H | CF₃ |
| 5-68 | NO₂ | NH₂ | F |
| 5-69 | NO₂ | NHMe | F |
| 5-70 | NO₂ | NMe₂ | F |
| 5-71 | NO₂ | Me | Cl |
| 5-72 | NO₂ | NH₂ | Cl |
| 5-73 | NO₂ | NHMe | Cl |
| 5-74 | NO₂ | NMe₂ | Cl |
| 5-75 | NO₂ | NH₂ | Br |
| 5-76 | NO₂ | NHMe | Br |
| 5-77 | NO₂ | NMe₂ | Br |
| 5-78 | NO₂ | NH₂ | CF₃ |
| 5-79 | NO₂ | NMe₂ | CF₃ |
| 5-80 | NO₂ | NH₂ | SO₂Me |
| 5-81 | NO₂ | NH₂ | SO₂Et |
| 5-82 | NO₂ | NHMe | SO₂Me |
| 5-83 | NO₂ | NMe₂ | SO₂Me |
| 5-84 | NO₂ | NMe₂ | SO₂Et |
| 5-85 | NO₂ | NH₂ | 1H-1,2,4-triazol-1-yl |
| 5-86 | NO₂ | NHMe | 1H-1,2,4-triazol-1-yl |
| 5-87 | NO₂ | NMe₂ | 1H-1,2,4-triazol-1-yl |
| 5-88 | Me | SMe | H |
| 5-89 | Me | SOMe | H |
| 5-90 | Me | SO₂Me | H |
| 5-91 | Me | SEt | H |
| 5-92 | Me | SOEt | H |
| 5-93 | Me | SO₂Et | H |
| 5-94 | Me | S(CH₂)₂OMe | H |
| 5-95 | Me | SO(CH₂)₂OMe | H |
| 5-96 | Me | SO₂(CH₂)₂OMe | H |
| 5-97 | Me | F | F |
| 5-98 | Me | F | Cl |
| 5-99 | Me | SEt | F |
| 5-100 | Me | SOEt | F |
| 5-101 | Me | SO₂Et | F |
| 5-102 | Me | Me | Cl |
| 5-103 | Me | F | Cl |
| 5-104 | Me | Cl | Cl |
| 5-105 | Me | NH₂ | Cl |
| 5-106 | Me | NHMe | Cl |
| 5-107 | Me | NMe₂ | Cl |
| 5-108 | Me | O(CH₂)₂OMe | Cl |
| 5-109 | Me | O(CH₂)₃OMe | Cl |
| 5-110 | Me | O(CH₂)₄OMe | Cl |
| 5-111 | Me | OCH₂CONMe₂ | Cl |
| 5-112 | Me | O(CH₂)₂—CO—NMe₂ | Cl |
| 5-113 | Me | O(CH₂)₂—NH(CO)NMe₂ | Cl |
| 5-114 | Me | O(CH₂)₂—NH(CO)NHCO₂Et | Cl |
| 5-115 | Me | O(CH₂)₂—NHCO₂Me | Cl |
| 5-116 | Me | O—CH₂—NHSO₂cPr | Cl |
| 5-117 | Me | O(CH₂)-5-2,4-dimethyl-2,4-dihydro-3H-1,2,4-triazol-3-on | Cl |
| 5-118 | Me | O(CH₂)-3,5-dime-thyl-1,2-oxazol-4-yl | Cl |
| 5-119 | Me | SMe | Cl |
| 5-120 | Me | SOMe | Cl |
| 5-121 | Me | SO₂Me | Cl |
| 5-122 | Me | SEt | Cl |
| 5-123 | Me | SOEt | Cl |
| 5-124 | Me | SO₂Et | Cl |
| 5-125 | Me | S(CH₂)₂OMe | Cl |
| 5-126 | Me | SO(CH₂)₂OMe | Cl |
| 5-127 | Me | SO₂(CH₂)₂OMe | Cl |
| 5-128 | Me | NH₂ | Br |
| 5-129 | Me | NHMe | Br |
| 5-130 | Me | NMe₂ | Br |
| 5-131 | Me | OCH₂(CO)NMe₂ | Br |
| 5-132 | Me | O(CH₂)-5-pyrrolidin-2-on | Br |
| 5-133 | Me | SMe | Br |
| 5-134 | Me | SOMe | Br |
| 5-135 | Me | SO₂Me | Br |
| 5-136 | Me | SEt | Br |
| 5-137 | Me | SOEt | Br |
| 5-138 | Me | SO₂Et | Br |
| 5-139 | Me | SMe | I |
| 5-140 | Me | SOMe | I |
| 5-141 | Me | SO₂Me | I |
| 5-142 | Me | SEt | I |
| 5-143 | Me | SOEt | I |
| 5-144 | Me | SO₂Et | I |
| 5-145 | Me | Cl | CF₃ |
| 5-146 | Me | SMe | CF₃ |
| 5-147 | Me | SOMe | CF₃ |
| 5-148 | Me | SO₂Me | CF₃ |
| 5-149 | Me | SEt | CF₃ |
| 5-150 | Me | SOEt | CF₃ |
| 5-151 | Me | SO₂Et | CF₃ |
| 5-152 | Me | S(CH₂)₂OMe | CF₃ |
| 5-153 | Me | SO(CH₂)₂OMe | CF₃ |
| 5-154 | Me | SO₂(CH₂)₂OMe | CF₃ |
| 5-155 | Me | Me | SO₂Me |
| 5-156 | Me | 4,5-dihydro-1,2-oxazol-3 yl | SO₂Me |
| 5-157 | Me | 4,5-dihydro-1,2-oxazol-3 yl | SO₂Et |
| 5-158 | Me | 5-cyanomethyl-4,5-dihydro-1,2-oxazol-3-yl | SO₂Me |
| 5-159 | Me | 5-cyanomethyl-4,5-dihydro-1,2-oxazol-3-yl | SO₂Et |
| 5-160 | Me | NH₂ | SO₂Me |
| 5-161 | Me | NHMe | SO₂Me |
| 5-162 | Me | NMe₂ | SO₂Me |
| 5-163 | Me | NH(CH₂)₂OMe | SO₂Me |
| 5-164 | Me | pyrazol-1-yl | SO₂Me |
| 5-165 | Me | OH | SO₂Me |
| 5-166 | Me | OMe | SO₂Me |

TABLE 5-continued

Compounds of the general formula (I) according to the invention in which A is CY, B is N and R is ethyl

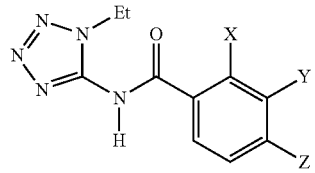

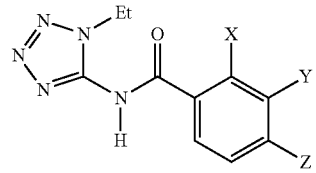

| No. | X | Y | Z |
|---|---|---|---|
| 5-167 | Me | OMe | SO$_2$Et |
| 5-168 | Me | OEt | SO$_2$Me |
| 5-169 | Me | OEt | SO$_2$Et |
| 5-170 | Me | OiPr | SO$_2$Me |
| 5-171 | Me | OiPr | SO$_2$Et |
| 5-172 | Me | O(CH$_2$)$_2$OMe | SO$_2$Me |
| 5-173 | Me | O(CH$_2$)$_2$OMe | SO$_2$Et |
| 5-174 | Me | O(CH$_2$)$_3$OMe | SO$_2$Me |
| 5-175 | Me | O(CH$_2$)$_3$OMe | SO$_2$Et |
| 5-176 | Me | O(CH$_2$)$_4$OMe | SO$_2$Me |
| 5-177 | Me | O(CH$_2$)$_4$OMe | SO$_2$Et |
| 5-178 | Me | O(CH$_2$)$_2$NHSO2Me | SO$_2$Me |
| 5-179 | Me | O(CH$_2$)$_2$NHSO2Me | SO$_2$Et |
| 5-180 | Me | OCH$_2$(CO)NMe$_2$ | SO$_2$Me |
| 5-181 | Me | OCH$_2$(CO)NMe$_2$ | SO$_2$Et |
| 5-182 | Me | [1,4]dioxan-2-yl-methoxy | SO$_2$Me |
| 5-183 | Me | [1,4]dioxan-2-yl-methoxy | SO$_2$Et |
| 5-184 | Me | O(CH$_2$)$_2$—O(3,5-dimethoxypyrimidin-2-yl | SO$_2$Me |
| 5-185 | Me | Cl | SO$_2$Me |
| 5-186 | Me | SMe | SO$_2$Me |
| 5-187 | Me | SOMe | SO$_2$Me |
| 5-188 | Me | SO$_2$Me | SO$_2$Me |
| 5-189 | Me | SO$_2$Me | SO$_2$Et |
| 5-190 | Me | SEt | SO$_2$Me |
| 5-191 | Me | SOEt | SO$_2$Me |
| 5-192 | Me | SO$_2$Et | SO$_2$Me |
| 5-193 | Me | S(CH$_2$)$_2$OMe | SO$_2$Me |
| 5-194 | Me | SO(CH$_2$)$_2$OMe | SO$_2$Me |
| 5-195 | Me | SO$_2$(CH$_2$)$_2$OMe | SO2Me |
| 5-196 | CH$_2$SMe | OMe | SO$_2$Me |
| 5-197 | CH$_2$OMe | OMe | SO$_2$Me |
| 5-198 | CH$_2$O(CH$_2$)$_2$OMe | NH(CH$_2$)$_2$OEt | SO$_2$Me |
| 5-199 | CH$_2$O(CH$_2$)$_2$OMe | NH(CH$_2$)$_3$OEt | SO$_2$Me |
| 5-200 | CH$_2$O(CH$_2$)$_3$OMe | OMe | SO$_2$Me |
| 5-201 | CH$_2$O(CH$_2$)$_2$OMe | NH(CH$_2$)$_2$OMe | SO$_2$Me |
| 5-202 | CH$_2$O(CH$_2$)$_2$OMe | NH(CH$_2$)$_3$OMe | SO$_2$Me |
| 5-203 | Et | SMe | Cl |
| 5-204 | Et | SO$_2$Me | Cl |
| 5-205 | Et | SMe | CF$_3$ |
| 5-206 | Et | SO$_2$Me | CF$_3$ |
| 5-207 | Et | F | SO$_2$Me |
| 5-208 | Et | NH(CH$_2$)$_2$OMe | SO$_2$Me |
| 5-209 | iPr | SO$_2$Me | CF$_3$ |
| 5-210 | cPr | SO$_2$Me | CF$_3$ |
| 5-211 | CF$_3$ | O(CH$_2$)$_2$OMe | F |
| 5-212 | CF$_3$ | O(CH$_2$)$_3$OMe | F |
| 5-213 | CF$_3$ | OCH$_2$CONMe$_2$ | F |
| 5-214 | CF$_3$ | [1,4]dioxan-2-yl-methoxy | F |
| 5-215 | CF$_3$ | O(CH$_2$)$_2$OMe | Cl |
| 5-216 | CF$_3$ | O(CH$_2$)$_3$OMe | Cl |
| 5-217 | CF$_3$ | OCH$_2$CONMe$_2$ | Cl |
| 5-218 | CF$_3$ | [1,4]dioxan-2-yl-methoxy | Cl |
| 5-219 | CF$_3$ | O(CH$_2$)$_2$OMe | Br |
| 5-220 | CF$_3$ | O(CH$_2$)$_3$OMe | Br |
| 5-221 | CF$_3$ | OCH$_2$CONMe$_2$ | Br |
| 5-222 | CF$_3$ | [1,4]dioxan-2-yl-methoxy | Br |
| 5-223 | CF$_3$ | O(CH$_2$)$_2$OMe | I |
| 5-224 | CF$_3$ | O(CH$_2$)$_3$OMe | I |
| 5-225 | CF$_3$ | OCH$_2$CONMe$_2$ | I |
| 5-226 | CF$_3$ | [1,4]dioxan-2-yl-methoxy | I |
| 5-227 | CF$_3$ | F | SO$_2$Me |
| 5-228 | CF$_3$ | F | SO$_2$Et |
| 5-229 | CF$_3$ | O(CH$_2$)$_2$OMe | SO$_2$Me |
| 5-230 | CF$_3$ | O(CH$_2$)$_2$OMe | SO$_2$Et |
| 5-231 | CF$_3$ | O(CH$_2$)$_3$OMe | SO$_2$Me |
| 5-232 | CF$_3$ | O(CH$_2$)$_3$OMe | SO$_2$Et |
| 5-233 | CF$_3$ | OCH$_2$CONMe$_2$ | SO$_2$Me |
| 5-234 | CF$_3$ | OCH$_2$CONMe$_2$ | SO$_2$Et |
| 5-235 | CF$_3$ | [1,4]dioxan-2-yl-methoxy | SO$_2$Me |
| 5-236 | CF$_3$ | [1,4]dioxan-2-yl-methoxy | SO$_2$Et |
| 5-237 | F | SMe | CF$_3$ |
| 5-238 | F | SOMe | CF$_3$ |
| 5-239 | Cl | Me | Cl |
| 5-240 | Cl | OCH$_2$CHCH$_2$ | Cl |
| 5-241 | Cl | OCH$_2$CHF$_2$ | Cl |
| 5-242 | Cl | O(CH$_2$)$_2$OMe | Cl |
| 5-243 | Cl | OCH$_2$(CO)NMe$_2$ | Cl |
| 5-244 | Cl | O(CH$_2$)-5-pyrrolidin-2-on | Cl |
| 5-245 | Cl | SMe | Cl |
| 5-246 | Cl | SOMe | Cl |
| 5-247 | Cl | SO$_2$Me | Cl |
| 5-248 | Cl | F | SMe |
| 5-249 | Cl | Cl | SO$_2$Me |
| 5-250 | Cl | COOMe | SO$_2$Me |
| 5-251 | Cl | CONMe$_2$ | SO$_2$Me |
| 5-252 | Cl | CONMe(OMe) | SO$_2$Me |
| 5-253 | Cl | CH$_2$OMe | SO$_2$Me |
| 5-254 | Cl | CH$_2$OMe | SO$_2$Et |
| 5-255 | Cl | CH$_2$OEt | SO$_2$Me |
| 5-256 | Cl | CH$_2$OEt | SO$_2$Et |
| 5-257 | Cl | CH$_2$OCH$_2$CHF$_2$ | SO$_2$Me |
| 5-258 | Cl | CH$_2$OCH$_2$CF$_3$ | SO$_2$Me |
| 5-259 | Cl | CH$_2$OCH$_2$CF$_3$ | SO$_2$Et |
| 5-260 | Cl | CH$_2$OCH$_2$CF$_2$CHF$_2$ | SO$_2$Me |
| 5-261 | Cl | CH$_2$OcPentyl | SO$_2$Me |
| 5-262 | Cl | CH$_2$PO(OMe)$_2$ | SO$_2$Me |
| 5-263 | Cl | 4,5-dihydro-1,2-oxazol-3 yl | SMe |
| 5-264 | Cl | 4,5-dihydro-1,2-oxazol-3 yl | SO$_2$Me |
| 5-265 | Cl | 4,5-dihydro-1,2-oxazol-3 yl | SO$_2$Et |
| 5-266 | Cl | 5-cyanomethyl- 4,5-dihydro-1,2-oxazol-3 yl | SO$_2$Me |
| 5-267 | Cl | 5-cyanomethyl- 4,5-dihydro-1,2-oxazol-3 yl | SO$_2$Et |
| 5-268 | Cl | 5-(Methoxyme-thyl)-4,5-dihydro-1,2-oxazol-3 yl | SO$_2$Et |
| 5-269 | Cl | 5-(Methoxyme-thyl)-5-Methyl-4,5-dihy-dro-1,2-oxazol-3 yl | SO$_2$Et |
| 5-270 | Cl | CH$_2$O-tetrahydrofuran-3-yl | SO$_2$Me |
| 5-271 | Cl | CH$_2$O-tetrahydrofuran-3-yl | SO$_2$Et |
| 5-272 | Cl | CH$_2$OCH$_2$-tetrahydrofuran-2-yl | SO$_2$Me |
| 5-273 | Cl | CH$_2$OCH$_2$-tetrahydrofuran-2-yl | SO$_2$Et |
| 5-274 | Cl | CH$_2$OCH$_2$-tetrahydrofuran-3-yl | SO$_2$Me |
| 5-275 | Cl | CH$_2$OCH$_2$-tetrahydrofuran-3-yl | SO$_2$Et |
| 5-276 | Cl | OMe | SO$_2$Me |
| 5-277 | Cl | OMe | SO$_2$Et |
| 5-278 | Cl | OEt | SO$_2$Me |
| 5-279 | Cl | OEt | SO$_2$Et |
| 5-280 | Cl | OiPr | SO$_2$Me |
| 5-281 | Cl | OiPr | SO$_2$Et |
| 5-282 | Cl | O(CH$_2$)$_2$OMe | SO$_2$Me |
| 5-283 | Cl | O(CH$_2$)$_4$OMe | SO$_2$Me |
| 5-284 | Cl | O(CH$_2$)$_4$OMe | SO$_2$Et |
| 5-285 | Cl | O(CH$_2$)$_3$OMe | SO$_2$Me |
| 5-286 | Cl | O(CH$_2$)$_3$OMe | SO$_2$Et |
| 5-287 | Cl | O(CH$_2$)$_2$OMe | SO$_2$Me |
| 5-288 | Cl | O(CH$_2$)$_2$OMe | SO$_2$Et |

TABLE 5-continued

Compounds of the general formula (I) according to the invention in which A is CY, B is N and R is ethyl

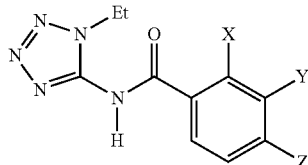

| No. | X | Y | Z |
|---|---|---|---|
| 5-289 | Cl | [1,4]dioxan-2-yl-methoxy | SO$_2$Me |
| 5-290 | Cl | [1,4]dioxan-2-yl-methoxy | SO$_2$Et |
| 5-291 | Cl | OCH$_2$(CO)NMe$_2$ | SO$_2$Me |
| 5-292 | Cl | OCH$_2$(CO)NMe$_2$ | SO$_2$Et |
| 5-293 | Cl | SMe | SO$_2$Me |
| 5-294 | Cl | SOMe | SO$_2$Me |
| 5-295 | Br | OMe | Br |
| 5-296 | Br | O(CH$_2$)$_2$OMe | Br |
| 5-297 | Br | O(CH$_2$)$_2$OMe | SO$_2$Me |
| 5-298 | Br | O(CH$_2$)$_2$OMe | SO$_2$Et |
| 5-299 | Br | O(CH$_2$)$_3$OMe | SO$_2$Me |
| 5-300 | Br | O(CH$_2$)$_3$OMe | SO$_2$Et |
| 5-301 | Br | O(CH$_2$)$_4$OMe | SO$_2$Me |
| 5-302 | Br | O(CH$_2$)$_4$OMe | SO$_2$Et |
| 5-303 | Br | [1,4]dioxan-2-yl-methoxy | SO$_2$Me |
| 5-304 | Br | [1,4]dioxan-2-yl-methoxy | SO$_2$Et |
| 5-305 | I | O(CH$_2$)$_2$OMe | SO$_2$Me |
| 5-306 | I | O(CH$_2$)$_2$OMe | SO$_2$Et |
| 5-307 | I | O(CH$_2$)$_3$OMe | SO$_2$Me |
| 5-308 | I | O(CH$_2$)$_3$OMe | SO$_2$Et |
| 5-309 | I | O(CH$_2$)$_4$OMe | SO$_2$Me |
| 5-310 | I | O(CH$_2$)$_4$OMe | SO$_2$Et |
| 5-311 | I | [1,4]dioxan-2-yl-methoxy | SO$_2$Me |
| 5-312 | I | [1,4]dioxan-2-yl-methoxy | SO$_2$Et |
| 5-313 | OMe | SMe | CF$_3$ |
| 5-314 | OMe | SOMe | CF$_3$ |
| 5-315 | OMe | SO$_2$Me | CF$_3$ |
| 5-316 | OMe | SOEt | CF$_3$ |
| 5-317 | OMe | SO$_2$Et | CF$_3$ |
| 5-318 | OMe | S(CH$_2$)$_2$OMe | CF$_3$ |
| 5-319 | OMe | SO(CH$_2$)$_2$OMe | CF$_3$ |
| 5-320 | OMe | SO$_2$(CH$_2$)$_2$OMe | CF$_3$ |
| 5-321 | OMe | SMe | Cl |
| 5-322 | OMe | SOMe | Cl |
| 5-323 | OMe | SO$_2$Me | Cl |
| 5-324 | OMe | SEt | Cl |
| 5-325 | OMe | SOEt | Cl |
| 5-326 | OMe | SO2Et | Cl |
| 5-327 | OMe | S(CH$_2$)$_2$OMe | Cl |
| 5-328 | OMe | SO(CH$_2$)$_2$OMe | Cl |
| 5-329 | OMe | SO$_2$(CH$_2$)$_2$OMe | Cl |
| 5-330 | OCH$_2$c-Pr | SMe | CF$_3$ |
| 5-331 | OCH$_2$c-Pr | SOMe | CF$_3$ |
| 5-332 | OCH$_2$c-Pr | SO$_2$Me | CF$_3$ |
| 5-333 | OCH$_2$c-Pr | SEt | CF$_3$ |
| 5-334 | OCH$_2$c-Pr | SOEt | CF$_3$ |
| 5-335 | OCH$_2$c-Pr | SO$_2$Et | CF$_3$ |
| 5-336 | OCH$_2$c-Pr | S(CH$_2$)$_2$OMe | CF$_3$ |
| 5-337 | OCH$_2$c-Pr | SO(CH$_2$)$_2$OMe | CF$_3$ |
| 5-338 | OCH$_2$c-Pr | SO$_2$(CH$_2$)$_2$OMe | CF$_3$ |
| 5-339 | OCH$_2$c-Pr | SMe | Cl |
| 5-340 | OCH$_2$c-Pr | SOMe | Cl |
| 5-341 | OCH$_2$c-Pr | SO$_2$Me | Cl |
| 5-342 | OCH$_2$c-Pr | SEt | Cl |
| 5-343 | OCH$_2$c-Pr | SOEt | Cl |
| 5-344 | OCH$_2$c-Pr | SO$_2$Et | Cl |
| 5-345 | OCH$_2$c-Pr | S(CH$_2$)$_2$OMe | Cl |
| 5-346 | OCH$_2$c-Pr | SO(CH$_2$)$_2$OMe | Cl |
| 5-347 | OCH$_2$c-Pr | SO$_2$(CH$_2$)$_2$OMe | Cl |
| 5-348 | OCH$_2$c-Pr | SMe | SO$_2$Me |
| 5-349 | OCH$_2$c-Pr | SOMe | SO$_2$Me |
| 5-350 | OCH$_2$c-Pr | SO$_2$Me | SO$_2$Me |
| 5-351 | OCH$_2$c-Pr | SEt | SO$_2$Me |
| 5-352 | OCH$_2$c-Pr | SOEt | SO$_2$Me |
| 5-353 | OCH$_2$c-Pr | SO$_2$Et | SO$_2$Me |
| 5-354 | OCH$_2$c-Pr | S(CH$_2$)$_2$OMe | SO$_2$Me |
| 5-355 | OCH$_2$c-Pr | SO(CH$_2$)$_2$OMe | SO$_2$Me |
| 5-356 | OCH$_2$c-Pr | SO$_2$(CH$_2$)$_2$OMe | SO$_2$Me |
| 5-357 | SO$_2$Me | F | CF$_3$ |
| 5-358 | SO$_2$Me | NH$_2$ | CF$_3$ |
| 5-359 | SO$_2$Me | NHEt | Cl |
| 5-360 | SMe | SEt | F |
| 5-361 | SMe | SMe | F |

TABLE 6

Compounds of the general formula (I) according to the invention in which A is CY, B is N and R is phenyl

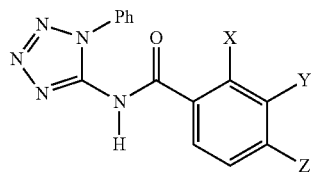

| No. | X | Y | Z |
|---|---|---|---|
| 6-1 | F | H | Cl |
| 6-2 | F | H | Br |
| 6-3 | F | H | SO$_2$Me |
| 6-4 | F | H | SO$_2$Et |
| 6-5 | F | H | CF$_3$ |
| 6-6 | F | H | NO$_2$ |
| 6-7 | Cl | H | F |
| 6-8 | Cl | H | Cl |
| 6-9 | Cl | H | Br |
| 6-10 | Cl | H | SMe |
| 6-11 | Cl | H | SOMe |
| 6-12 | Cl | H | SO$_2$Me |
| 6-13 | Cl | H | SO$_2$CH$_2$Cl |
| 6-14 | Cl | H | SEt |
| 6-15 | Cl | H | SO$_2$Et |
| 6-16 | Cl | H | CF$_3$ |
| 6-17 | Cl | H | NO$_2$ |
| 6-18 | Cl | H | pyrazol-1-yl |
| 6-19 | Cl | H | 1H-1,2,4-triazol-1-yl |
| 6-20 | Br | H | Cl |
| 6-21 | Br | H | Br |
| 6-22 | Br | H | SO$_2$Me |
| 6-23 | Br | H | SO$_2$Et |
| 6-24 | Br | H | CF$_3$ |
| 6-25 | SO$_2$Me | H | Cl |
| 6-26 | SO$_2$Me | H | Br |
| 6-27 | SO$_2$Me | H | SMe |
| 6-28 | SO$_2$Me | H | SOMe |
| 6-29 | SO$_2$Me | H | SO$_2$Me |
| 6-30 | SO$_2$Me | H | SO$_2$Et |
| 6-31 | SMe | H | CF$_3$ |
| 6-32 | SO$_2$Me | H | CF$_3$ |
| 6-33 | SO$_2$Et | H | Cl |
| 6-34 | SO$_2$Et | H | Br |
| 6-35 | SO$_2$Et | H | SMe |
| 6-36 | SO$_2$Et | H | SOMe |
| 6-37 | SO$_2$Et | H | SO$_2$Me |
| 6-38 | SO$_2$Et | H | CF$_3$ |
| 6-39 | NO$_2$ | H | F |

TABLE 6-continued

Compounds of the general formula (I) according to the invention in which A is CY, B is N and R is phenyl

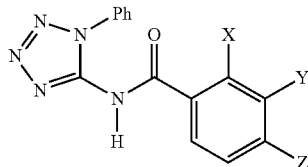
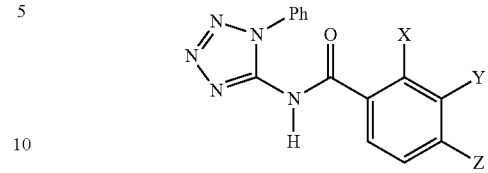

| No. | X | Y | Z |
|---|---|---|---|
| 6-40 | NO$_2$ | H | Cl |
| 6-41 | NO$_2$ | H | Br |
| 6-42 | NO$_2$ | H | I |
| 6-43 | NO$_2$ | H | CN |
| 6-44 | NO$_2$ | H | SO$_2$Me |
| 6-45 | NO$_2$ | H | SO$_2$Et |
| 6-46 | NO$_2$ | H | CF$_3$ |
| 6-47 | Me | H | Cl |
| 6-48 | Me | H | Br |
| 6-49 | Me | H | SMe |
| 6-50 | Me | H | SO$_2$Me |
| 6-51 | Me | H | SO$_2$CH$_2$Cl |
| 6-52 | Me | H | SEt |
| 6-53 | Me | H | SO$_2$Et |
| 6-54 | Me | H | CF$_3$ |
| 6-55 | CH$_2$SO$_2$Me | H | CF$_3$ |
| 6-56 | Et | H | Cl |
| 6-57 | Et | H | Br |
| 6-58 | Et | H | SMe |
| 6-59 | Et | H | SO$_2$Me |
| 6-60 | Et | H | SO$_2$CH$_2$Cl |
| 6-61 | Et | H | SEt |
| 6-62 | Et | H | SO$_2$Et |
| 6-63 | Et | H | CF$_3$ |
| 6-64 | CF$_3$ | H | Cl |
| 6-65 | CF$_3$ | H | Br |
| 6-66 | CF$_3$ | H | SO$_2$Me |
| 6-67 | CF$_3$ | H | SO$_2$Et |
| 6-68 | CF$_3$ | H | CF$_3$ |
| 6-69 | NO$_2$ | NH$_2$ | F |
| 6-70 | NO$_2$ | NHMe | F |
| 6-71 | NO$_2$ | NMe$_2$ | F |
| 6-72 | NO$_2$ | Me | Cl |
| 6-73 | NO$_2$ | NH$_2$ | Cl |
| 6-74 | NO$_2$ | NHMe | Cl |
| 6-75 | NO$_2$ | NMe$_2$ | Cl |
| 6-76 | NO$_2$ | NH$_2$ | Br |
| 6-77 | NO$_2$ | NHMe | Br |
| 6-78 | NO$_2$ | NMe$_2$ | Br |
| 6-79 | NO$_2$ | NH$_2$ | CF$_3$ |
| 6-80 | NO$_2$ | NMe$_2$ | CF$_3$ |
| 6-81 | NO$_2$ | NH$_2$ | SO$_2$Me |
| 6-82 | NO$_2$ | NH$_2$ | SO$_2$Et |
| 6-83 | NO$_2$ | NHMe | SO$_2$Me |
| 6-84 | NO$_2$ | NMe$_2$ | SO$_2$Me |
| 6-85 | NO$_2$ | NMe$_2$ | SO$_2$Et |
| 6-86 | NO$_2$ | NH$_2$ | 1H-1,2,4-triazol-1-yl |
| 6-87 | NO$_2$ | NHMe | 1H-1,2,4-triazol-1-yl |
| 6-88 | NO$_2$ | NMe$_2$ | 1H-1,2,4-triazol-1-yl |
| 6-89 | Me | SMe | H |
| 6-90 | Me | SOMe | H |
| 6-91 | Me | SO$_2$Me | H |
| 6-92 | Me | SEt | H |
| 6-93 | Me | SOEt | H |
| 6-94 | Me | SO$_2$Et | H |
| 6-95 | Me | S(CH$_2$)$_2$OMe | H |
| 6-96 | Me | SO(CH$_2$)$_2$OMe | H |
| 6-97 | Me | SO$_2$(CH$_2$)$_2$OMe | H |
| 6-98 | Me | F | F |
| 6-99 | Me | F | Cl |
| 6-100 | Me | SEt | F |
| 6-101 | Me | SOEt | F |
| 6-102 | Me | SO$_2$Et | F |
| 6-103 | Me | Me | Cl |
| 6-104 | Me | F | Cl |
| 6-105 | Me | Cl | Cl |
| 6-106 | Me | NH$_2$ | Cl |
| 6-107 | Me | NHMe | Cl |
| 6-108 | Me | NMe$_2$ | Cl |
| 6-109 | Me | O(CH$_2$)$_2$OMe | Cl |
| 6-110 | Me | O(CH$_2$)$_3$OMe | Cl |
| 6-111 | Me | O(CH$_2$)$_4$OMe | Cl |
| 6-112 | Me | OCH$_2$CONMe$_2$ | Cl |
| 6-113 | Me | O(CH$_2$)$_2$—CO—NMe$_2$ | Cl |
| 6-114 | Me | O(CH$_2$)$_2$—NH(CO)NMe$_2$ | Cl |
| 6-115 | Me | O(CH$_2$)$_2$—NH(CO)NHCO$_2$Et | Cl |
| 6-116 | Me | O(CH$_2$)$_2$—NHCO$_2$Me | Cl |
| 6-117 | Me | O—CH$_2$—NHSO$_2$cPr | Cl |
| 6-118 | Me | O(CH$_2$)-5-2,4-dime-thyl-2,4-dihydro-3H-1,2,4-triazol-3-on | Cl |
| 6-119 | Me | O(CH$_2$)-3,5-dime-thyl-1,2-oxazol-4-yl | Cl |
| 6-120 | Me | SMe | Cl |
| 6-121 | Me | SOMe | Cl |
| 6-122 | Me | SO$_2$Me | Cl |
| 6-123 | Me | SEt | Cl |
| 6-124 | Me | SOEt | Cl |
| 6-125 | Me | SO$_2$Et | Cl |
| 6-126 | Me | S(CH$_2$)$_2$OMe | Cl |
| 6-127 | Me | SO(CH$_2$)$_2$OMe | Cl |
| 6-128 | Me | SO$_2$(CH$_2$)$_2$OMe | Cl |
| 6-129 | Me | NH$_2$ | Br |
| 6-130 | Me | NHMe | Br |
| 6-131 | Me | NMe$_2$ | Br |
| 6-132 | Me | O(CH$_2$)—(CO)NEt$_2$ | Br |
| 6-133 | Me | O(CH$_2$)-5-pyrrolidin-2-on | Br |
| 6-134 | Me | SMe | Br |
| 6-135 | Me | SOMe | Br |
| 6-136 | Me | SO$_2$Me | Br |
| 6-137 | Me | SEt | Br |
| 6-138 | Me | SOEt | Br |
| 6-139 | Me | SO$_2$Et | Br |
| 6-140 | Me | SMe | I |
| 6-141 | Me | SOMe | I |
| 6-142 | Me | SO$_2$Me | I |
| 6-143 | Me | SEt | I |
| 6-144 | Me | SOEt | I |
| 6-145 | Me | SO$_2$Et | I |
| 6-146 | Me | Cl | CF$_3$ |
| 6-147 | Me | SMe | CF$_3$ |
| 6-148 | Me | SOMe | CF$_3$ |
| 6-149 | Me | SO$_2$Me | CF$_3$ |
| 6-150 | Me | SEt | CF$_3$ |
| 6-151 | Me | SOEt | CF$_3$ |
| 6-152 | Me | SO$_2$Et | CF$_3$ |
| 6-153 | Me | S(CH$_2$)$_2$OMe | CF$_3$ |
| 6-154 | Me | SO(CH$_2$)$_2$OMe | CF$_3$ |
| 6-155 | Me | SO$_2$(CH$_2$)$_2$OMe | CF$_3$ |
| 6-156 | Me | Me | SO$_2$Me |
| 6-157 | Me | 4,5-dihydro-1,2-oxazol-3 yl | SO$_2$Me |
| 6-158 | Me | 4,5-dihydro-1,2-oxazol-3 yl | SO$_2$Et |
| 6-159 | Me | 5-cyanomethyl-4,5-dihydro-1,2-oxazol-3-yl | SO$_2$Me |
| 6-160 | Me | 5-cyanomethyl-4,5-dihydro-1,2-oxazol-3-yl | SO$_2$Et |
| 6-161 | Me | NH$_2$ | SO$_2$Me |
| 6-162 | Me | NHMe | SO$_2$Me |
| 6-163 | Me | NMe$_2$ | SO$_2$Me |
| 6-164 | Me | NH(CH$_2$)$_2$OMe | SO$_2$Me |

TABLE 6-continued

Compounds of the general formula (I) according to the invention in which A is CY, B is N and R is phenyl

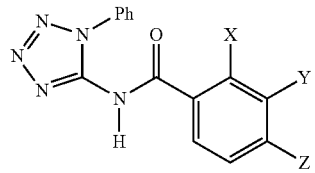

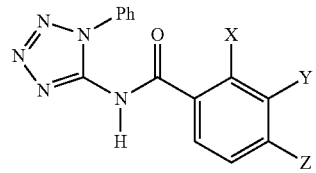

| No. | X | Y | Z |
|---|---|---|---|
| 6-165 | Me | pyrazol-1-yl | SO₂Me |
| 6-166 | Me | OH | SO₂Me |
| 6-167 | Me | OMe | SO₂Me |
| 6-168 | Me | OMe | SO₂Et |
| 6-169 | Me | OEt | SO₂Me |
| 6-170 | Me | OEt | SO₂Et |
| 6-171 | Me | OiPr | SO₂Me |
| 6-172 | Me | OiPr | SO₂Et |
| 6-173 | Me | O(CH₂)₂OMe | SO₂Me |
| 6-174 | Me | O(CH₂)₂OMe | SO₂Et |
| 6-175 | Me | O(CH₂)₃OMe | SO₂Me |
| 6-176 | Me | O(CH₂)₃OMe | SO₂Et |
| 6-177 | Me | O(CH₂)₄OMe | SO₂Me |
| 6-178 | Me | O(CH₂)₄OMe | SO₂Et |
| 6-179 | Me | O(CH₂)₂NHSO2Me | SO₂Me |
| 6-180 | Me | O(CH₂)₂NHSO2Me | SO₂Et |
| 6-181 | Me | OCH₂(CO)NMe₂ | SO₂Me |
| 6-182 | Me | OCH₂(CO)NMe₂ | SO₂Et |
| 6-183 | Me | [1,4]dioxan-2-yl-methoxy | SO₂Me |
| 6-184 | Me | [1,4]dioxan-2-yl-methoxy | SO₂Et |
| 6-185 | Me | O(CH₂)₂—O(3,5-dimethoxypyrimidin-2-yl) | SO₂Me |
| 6-186 | Me | Cl | SO₂Me |
| 6-187 | Me | SMe | SO₂Me |
| 6-188 | Me | SOMe | SO₂Me |
| 6-189 | Me | SO₂Me | SO₂Me |
| 6-190 | Me | SO₂Me | SO₂Et |
| 6-191 | Me | SEt | SO₂Me |
| 6-192 | Me | SOEt | SO₂Me |
| 6-193 | Me | SO₂Et | SO₂Me |
| 6-194 | Me | S(CH₂)₂OMe | SO₂Me |
| 6-195 | Me | SO(CH₂)₂OMe | SO₂Me |
| 6-196 | Me | SO₂(CH₂)₂OMe | SO2Me |
| 6-197 | CH₂SMe | OMe | SO₂Me |
| 6-198 | CH₂OMe | OMe | SO₂Me |
| 6-199 | CH₂O(CH₂)₂OMe | NH(CH₂)₂OEt | SO₂Me |
| 6-200 | CH₂O(CH₂)₂OMe | NH(CH₂)₃OEt | SO₂Me |
| 6-201 | CH₂O(CH₂)₃OMe | OMe | SO₂Me |
| 6-202 | CH₂O(CH₂)₂OMe | NH(CH₂)₂OMe | SO₂Me |
| 6-203 | CH₂O(CH₂)₂OMe | NH(CH₂)₃OMe | SO₂Me |
| 6-204 | Et | SMe | Cl |
| 6-205 | Et | SO₂Me | Cl |
| 6-206 | Et | SMe | CF₃ |
| 6-207 | Et | SO₂Me | CF₃ |
| 6-208 | Et | F | SO₂Me |
| 6-209 | Et | NH(CH₂)₂OMe | SO₂Me |
| 6-210 | iPr | SO₂Me | CF₃ |
| 6-211 | cPr | SO₂Me | CF₃ |
| 6-212 | CF₃ | O(CH₂)₂OMe | F |
| 6-213 | CF₃ | O(CH₂)₃OMe | F |
| 6-214 | CF₃ | OCH₂CONMe₂ | F |
| 6-215 | CF₃ | [1,4]dioxan-2-yl-methoxy | F |
| 6-216 | CF₃ | O(CH₂)₂OMe | Cl |
| 6-217 | CF₃ | O(CH₂)₃OMe | Cl |
| 6-218 | CF₃ | OCH₂CONMe₂ | Cl |
| 6-219 | CF₃ | [1,4]dioxan-2-yl-methoxy | Cl |
| 6-220 | CF₃ | O(CH₂)₂OMe | Br |
| 6-221 | CF₃ | O(CH₂)₃OMe | Br |
| 6-222 | CF₃ | OCH₂CONMe₂ | Br |
| 6-223 | CF₃ | [1,4]dioxan-2-yl-methoxy | Br |
| 6-224 | CF₃ | O(CH₂)₂OMe | I |
| 6-225 | CF₃ | O(CH₂)₃OMe | I |
| 6-226 | CF₃ | OCH₂CONMe₂ | I |
| 6-227 | CF₃ | [1,4]dioxan-2-yl-methoxy | I |
| 6-228 | CF₃ | F | SO₂Me |
| 6-229 | CF₃ | F | SO₂Et |
| 6-230 | CF₃ | O(CH₂)₂OMe | SO₂Me |
| 6-231 | CF₃ | O(CH₂)₂OMe | SO₂Et |
| 6-232 | CF₃ | O(CH₂)₃OMe | SO₂Me |
| 6-233 | CF₃ | O(CH₂)₃OMe | SO₂Et |
| 6-234 | CF₃ | OCH₂CONMe₂ | SO₂Me |
| 6-235 | CF₃ | OCH₂CONMe₂ | SO₂Et |
| 6-236 | CF₃ | [1,4]dioxan-2-yl-methoxy | SO₂Me |
| 6-237 | CF₃ | [1,4]dioxan-2-yl-methoxy | SO₂Et |
| 6-238 | F | SMe | CF₃ |
| 6-239 | F | SOMe | CF₃ |
| 6-240 | Cl | Me | Cl |
| 6-241 | Cl | OCH₂CHCH₂ | Cl |
| 6-242 | Cl | OCH₂CHF₂ | Cl |
| 6-243 | Cl | O(CH₂)₂OMe | Cl |
| 6-244 | Cl | OCH₂(CO)NMe₂ | Cl |
| 6-245 | Cl | O(CH₂)-5-pyrrolidin-2-on | Cl |
| 6-246 | Cl | SMe | Cl |
| 6-247 | Cl | SOMe | Cl |
| 6-248 | Cl | SO₂Me | Cl |
| 6-249 | Cl | F | SMe |
| 6-250 | Cl | Cl | SO₂Me |
| 6-251 | Cl | COOMe | SO₂Me |
| 6-252 | Cl | CONMe₂ | SO₂Me |
| 6-253 | Cl | CONMe(OMe) | SO₂Me |
| 6-254 | Cl | CH₂OMe | SO₂Me |
| 6-255 | Cl | CH₂OMe | SO₂Et |
| 6-256 | Cl | CH₂OEt | SO₂Me |
| 6-257 | Cl | CH₂OEt | SO₂Et |
| 6-258 | Cl | CH₂OCH₂CHF₂ | SO₂Me |
| 6-259 | Cl | CH₂OCH₂CF₃ | SO₂Me |
| 6-260 | Cl | CH₂OCH₂CF₃ | SO₂Et |
| 6-261 | Cl | CH₂OCH₂CF₂CHF₂ | SO₂Me |
| 6-262 | Cl | CH₂OcPentyl | SO₂Me |
| 6-263 | Cl | CH₂PO(OMe)₂ | SO₂Me |
| 6-264 | Cl | 4,5-dihydro-1,2-oxazol-3 yl | SMe |
| 6-265 | Cl | 4,5-dihydro-1,2-oxazol-3 yl | SO₂Me |
| 6-266 | Cl | 4,5-dihydro-1,2-oxazol-3 yl | SO₂Et |
| 6-267 | Cl | 5-cyanomethyl-4,5-dihydro-1,2-oxazol-3 yl | SO₂Me |
| 6-268 | Cl | 5-cyanomethyl-4,5-dihydro-1,2-oxazol-3 yl | SO₂Et |
| 6-269 | Cl | 5-(Methoxymethyl)-4,5-dihydro-1,2-oxazol-3 yl | SO₂Et |
| 6-270 | Cl | 5-(Methoxymethyl)-5-Methyl-4,5-dihy-dro-1,2-oxazol-3 yl | SO₂Et |
| 6-271 | Cl | CH₂O-tetrahydrofuran-3-yl | SO₂Me |
| 6-272 | Cl | CH₂O-tetrahydrofuran-3-yl | SO₂Et |
| 6-273 | Cl | CH₂OCH₂-tetrahydrofuran-2-yl | SO₂Me |
| 6-274 | Cl | CH₂OCH₂-tetrahydrofuran-2-yl | SO₂Et |
| 6-275 | Cl | CH₂OCH₂-tetrahydrofuran-3-yl | SO₂Me |
| 6-276 | Cl | CH₂OCH₂-tetrahydrofuran-3-yl | SO₂Et |
| 6-277 | Cl | OMe | SO₂Me |
| 6-278 | Cl | OMe | SO₂Et |
| 6-279 | Cl | OEt | SO₂Me |
| 6-280 | Cl | OEt | SO₂Et |
| 6-281 | Cl | OiPr | SO₂Me |
| 6-282 | Cl | OiPr | SO₂Et |
| 6-283 | Cl | O(CH₂)₂OMe | SO₂Me |
| 6-284 | Cl | O(CH₂)₄OMe | SO₂Me |
| 6-285 | Cl | O(CH₂)₄OMe | SO₂Et |
| 6-286 | Cl | O(CH₂)₃OMe | SO₂Me |

TABLE 6-continued

Compounds of the general formula (I) according to the invention in which A is CY, B is N and R is phenyl

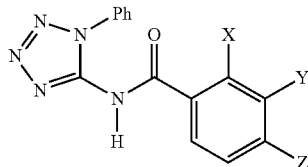

| No. | X | Y | Z |
|---|---|---|---|
| 6-287 | Cl | O(CH$_2$)$_3$OMe | SO$_2$Et |
| 6-288 | Cl | O(CH$_2$)$_2$OMe | SO$_2$Me |
| 6-289 | Cl | O(CH$_2$)$_2$OMe | SO$_2$Et |
| 6-290 | Cl | [1,4]dioxan-2-yl-methoxy | SO$_2$Me |
| 6-291 | Cl | [1,4]dioxan-2-yl-methoxy | SO$_2$Et |
| 6-292 | Cl | OCH$_2$(CO)NMe$_2$ | SO$_2$Me |
| 6-293 | Cl | OCH$_2$(CO)NMe$_2$ | SO$_2$Et |
| 6-294 | Cl | SMe | SO$_2$Me |
| 6-295 | Cl | SOMe | SO$_2$Me |
| 6-296 | Br | OMe | Br |
| 6-297 | Br | O(CH$_2$)$_2$OMe | Br |
| 6-298 | Br | O(CH$_2$)$_2$OMe | SO$_2$Me |
| 6-299 | Br | O(CH$_2$)$_2$OMe | SO$_2$Et |
| 6-300 | Br | O(CH$_2$)$_3$OMe | SO$_2$Me |
| 6-301 | Br | O(CH$_2$)$_3$OMe | SO$_2$Et |
| 6-302 | Br | O(CH$_2$)$_4$OMe | SO$_2$Me |
| 6-303 | Br | O(CH$_2$)$_4$OMe | SO$_2$Et |
| 6-304 | Br | [1,4]dioxan-2-yl-methoxy | SO$_2$Me |
| 6-305 | Br | [1,4]dioxan-2-yl-methoxy | SO$_2$Et |
| 6-306 | I | O(CH$_2$)$_2$OMe | SO$_2$Me |
| 6-307 | I | O(CH$_2$)$_2$OMe | SO$_2$Et |
| 6-308 | I | O(CH$_2$)$_3$OMe | SO$_2$Me |
| 6-309 | I | O(CH$_2$)$_3$OMe | SO$_2$Et |
| 6-310 | I | O(CH$_2$)$_4$OMe | SO$_2$Me |
| 6-311 | I | O(CH$_2$)$_4$OMe | SO$_2$Et |
| 6-312 | I | [1,4]dioxan-2-yl-methoxy | SO$_2$Me |
| 6-313 | I | [1,4]dioxan-2-yl-methoxy | SO$_2$Et |
| 6-314 | OMe | SMe | CF$_3$ |
| 6-315 | OMe | SOMe | CF$_3$ |
| 6-316 | OMe | SO$_2$Me | CF$_3$ |
| 6-317 | OMe | SOEt | CF$_3$ |
| 6-318 | OMe | SO$_2$Et | CF$_3$ |
| 6-319 | OMe | S(CH$_2$)$_2$OMe | CF$_3$ |
| 6-320 | OMe | SO(CH$_2$)$_2$OMe | CF$_3$ |
| 6-321 | OMe | SO$_2$(CH$_2$)$_2$OMe | CF$_3$ |
| 6-322 | OMe | SMe | Cl |
| 6-323 | OMe | SOMe | Cl |
| 6-324 | OMe | SO$_2$Me | Cl |
| 6-325 | OMe | SEt | Cl |
| 6-326 | OMe | SOEt | Cl |
| 6-327 | OMe | SO2Et | Cl |
| 6-328 | OMe | S(CH$_2$)$_2$OMe | Cl |
| 6-329 | OMe | SO(CH$_2$)$_2$OMe | Cl |
| 6-330 | OMe | SO$_2$(CH$_2$)$_2$OMe | Cl |
| 6-331 | OCH$_2$c-Pr | SMe | CF$_3$ |
| 6-332 | OCH$_2$c-Pr | SOMe | CF$_3$ |
| 6-333 | OCH$_2$c-Pr | SO$_2$Me | CF$_3$ |
| 6-334 | OCH$_2$c-Pr | SEt | CF$_3$ |
| 6-335 | OCH$_2$c-Pr | SOEt | CF$_3$ |
| 6-336 | OCH$_2$c-Pr | SO$_2$Et | CF$_3$ |
| 6-337 | OCH$_2$c-Pr | S(CH$_2$)$_2$OMe | CF$_3$ |
| 6-338 | OCH$_2$c-Pr | SO(CH$_2$)$_2$OMe | CF$_3$ |
| 6-339 | OCH$_2$c-Pr | SO$_2$(CH$_2$)$_2$OMe | CF$_3$ |
| 6-340 | OCH$_2$c-Pr | SMe | Cl |
| 6-341 | OCH$_2$c-Pr | SOMe | Cl |
| 6-342 | OCH$_2$c-Pr | SO$_2$Me | Cl |
| 6-343 | OCH$_2$c-Pr | SEt | Cl |
| 6-344 | OCH$_2$c-Pr | SOEt | Cl |
| 6-345 | OCH$_2$c-Pr | SO$_2$Et | Cl |
| 6-346 | OCH$_2$c-Pr | S(CH$_2$)$_2$OMe | Cl |
| 6-347 | OCH$_2$c-Pr | SO(CH$_2$)$_2$OMe | Cl |
| 6-348 | OCH$_2$c-Pr | SO$_2$(CH$_2$)$_2$OMe | Cl |
| 6-349 | OCH$_2$c-Pr | SMe | SO$_2$Me |
| 6-350 | OCH$_2$c-Pr | SOMe | SO$_2$Me |
| 6-351 | OCH$_2$c-Pr | SO$_2$Me | SO$_2$Me |
| 6-352 | OCH$_2$c-Pr | SEt | SO$_2$Me |

TABLE 6-continued

Compounds of the general formula (I) according to the invention in which A is CY, B is N and R is phenyl

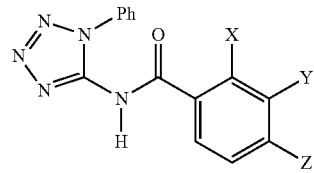

| No. | X | Y | Z |
|---|---|---|---|
| 6-353 | OCH$_2$c-Pr | SOEt | SO$_2$Me |
| 6-354 | OCH$_2$c-Pr | SO$_2$Et | SO$_2$Me |
| 6-355 | OCH$_2$c-Pr | S(CH$_2$)$_2$OMe | SO$_2$Me |
| 6-356 | OCH$_2$c-Pr | SO(CH$_2$)$_2$OMe | SO$_2$Me |
| 6-357 | OCH$_2$c-Pr | SO$_2$(CH$_2$)$_2$OMe | SO$_2$Me |
| 6-358 | SO$_2$Me | F | CF$_3$ |
| 6-359 | SO$_2$Me | NH$_2$ | CF$_3$ |
| 6-360 | SO$_2$Me | NHEt | Cl |
| 6-361 | SMe | SEt | F |
| 6-362 | SMe | SMe | F |

TABLE 7

Compounds of the general formula (I) according to the invention in which A is CY

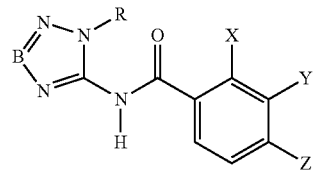

| No. | B | R | X | Y | Z |
|---|---|---|---|---|---|
| 7-1 | CH | nPr | Cl | H | SO$_2$Me |
| 7-2 | CH | iPr | Cl | H | SO$_2$Me |
| 7-3 | N | nPr | Cl | H | SO$_2$Me |
| 7-4 | N | iPr | Cl | H | SO$_2$Me |
| 7-5 | N | cPr | Cl | H | SO$_2$Me |
| 7-6 | N | Allyl | Cl | H | SO$_2$Me |
| 7-7 | N | CH$_2$OMe | Cl | H | SO$_2$Me |
| 7-8 | CH | nPr | NO$_2$ | H | SO$_2$Me |
| 7-9 | CH | iPr | NO$_2$ | H | SO$_2$Me |
| 7-10 | N | nPr | NO$_2$ | H | SO$_2$Me |
| 7-11 | N | iPr | NO$_2$ | H | SO$_2$Me |
| 7-12 | N | cPr | NO$_2$ | H | SO$_2$Me |
| 7-13 | N | Allyl | NO$_2$ | H | SO$_2$Me |
| 7-14 | N | CH$_2$OMe | NO$_2$ | H | SO$_2$Me |
| 7-15 | CH | nPr | SO$_2$Me | H | CF$_3$ |
| 7-16 | CH | iPr | SO$_2$Me | H | CF$_3$ |
| 7-17 | N | nPr | SO$_2$Me | H | CF$_3$ |
| 7-18 | N | iPr | SO$_2$Me | H | CF$_3$ |
| 7-19 | N | cPr | SO$_2$Me | H | CF$_3$ |
| 7-20 | N | Allyl | SO$_2$Me | H | CF$_3$ |
| 7-21 | N | CH$_2$OMe | SO$_2$Me | H | CF$_3$ |
| 7-22 | CH | nPr | Cl | CH$_2$OCH$_2$CF$_3$ | SO$_2$Me |
| 7-23 | CH | iPr | Cl | CH$_2$OCH$_2$CF$_3$ | SO$_2$Me |
| 7-24 | N | nPr | Cl | CH$_2$OCH$_2$CF$_3$ | SO$_2$Me |
| 7-25 | N | iPr | Cl | CH$_2$OCH$_2$CF$_3$ | SO$_2$Me |
| 7-26 | N | cPr | Cl | CH$_2$OCH$_2$CF$_3$ | SO$_2$Me |
| 7-27 | N | Allyl | Cl | CH$_2$OCH$_2$CF$_3$ | SO$_2$Me |
| 7-28 | N | CH$_2$OMe | Cl | CH$_2$OCH$_2$CF$_3$ | SO$_2$Me |
| 7-29 | CH | nPr | Me | SO$_2$Me | CF$_3$ |
| 7-30 | CH | iPr | Me | SO$_2$Me | CF$_3$ |
| 7-31 | CH | Pyrid-2-yl | Me | SO$_2$Me | CF$_3$ |
| 7-32 | N | nPr | Me | SO$_2$Me | CF$_3$ |
| 7-33 | N | iPr | Me | SO$_2$Me | CF$_3$ |
| 7-34 | N | cPr | Me | SO$_2$Me | CF$_3$ |
| 7-35 | N | Allyl | Me | SO$_2$Me | CF$_3$ |
| 7-36 | N | CH$_2$OMe | Me | SO$_2$Me | CF$_3$ |

TABLE 7-continued

Compounds of the general formula (I) according to the invention in which A is CY

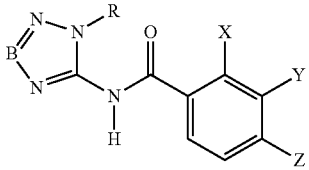

| No. | B | R | X | Y | Z |
|---|---|---|---|---|---|
| 7-37 | N | $CH_2(CO)Me$ | Me | $SO_2Me$ | $CF_3$ |
| 7-38 | N | $CH_2COOEt$ | Me | $SO_2Me$ | $CF_3$ |
| 7-39 | N | 4-Cl-benzyl | Me | $SO_2Me$ | $CF_3$ |
| 7-40 | CH | nPr | Me | $SO_2Me$ | $SO_2Me$ |
| 7-41 | CH | iPr | Me | $SO_2Me$ | $SO_2Me$ |
| 7-42 | N | nPr | Me | $SO_2Me$ | $SO_2Me$ |
| 7-43 | N | iPr | Me | $SO_2Me$ | $SO_2Me$ |
| 7-44 | N | cPr | Me | $SO_2Me$ | $SO_2Me$ |
| 7-45 | N | $CH_2OMe$ | Me | $SO_2Me$ | $SO_2Me$ |
| 7-46 | N | $CH_2(CO)Me$ | Me | $SO_2Me$ | $SO_2Me$ |
| 7-47 | N | $CH_2COOEt$ | Me | $SO_2Me$ | $SO_2Me$ |
| 7-48 | N | 4-Cl-benzyl | Me | $SO_2Me$ | $SO_2Me$ |

TABLE 8

Compounds of the general formula (I) according to the invention in which A is N

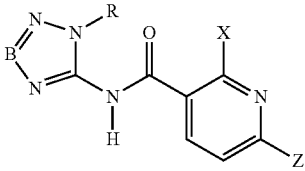

| No. | B | R | X | Z |
|---|---|---|---|---|
| 8-1 | CH | Me | Cl | Cl |
| 8-2 | N | Me | Cl | Cl |
| 8-3 | CH | Me | Me | Cl |
| 8-4 | N | Me | Me | Cl |
| 8-5 | CH | Me | Cl | SMe |
| 8-6 | N | Me | Cl | SMe |
| 8-7 | CH | Me | Me | $SO_2Me$ |
| 8-8 | N | Me | Me | $SO_2Me$ |
| 8-9 | CH | Me | Cl | $CF_3$ |
| 8-10 | N | Me | Cl | $CF_3$ |
| 8-11 | CH | Ph | Cl | $CF_3$ |
| 8-12 | N | Ph | Cl | $CF_3$ |
| 8-13 | N | $CH_2(CO)Me$ | Cl | $CF_3$ |
| 8-14 | N | Benzoyl | Cl | $CF_3$ |
| 8-15 | N | Allyl | Cl | $CF_3$ |
| 8-16 | N | 4-Cl-benzyl | Cl | $CF_3$ |
| 8-17 | N | $CH_2CO_2Et$ | Cl | $CF_3$ |
| 8-18 | CH | Me | Me | $CF_3$ |
| 8-19 | N | Me | Me | $CF_3$ |
| 8-20 | CH | Me | $CH_2OMe$ | $CF_3$ |
| 8-21 | N | Me | $CH_2OMe$ | $CF_3$ |
| 8-22 | CH | Me | $CH_2OC_2H_4OMe$ | $CF_3$ |
| 8-23 | N | Me | $CH_2OC_2H_4OMe$ | $CF_3$ |

As already disclosed in European patent application "EP 10174893" (being filed in the name of Bayer CropScience AG at the EPO on Sep. 1, 2010) and its corresponding international application PCT/EP 2011/064820, the compounds of the formula (I) and/or their salts to be used according to the invention, hereinbelow also referred to together as "compounds according to the invention", have excellent herbicidal efficacy against a broad spectrum of economically important monocotyledonous and dicotyledonous annual harmful plants. The active compounds act efficiently even on perennial weeds which produce shoots from rhizomes, rootstocks and other perennial organs and which are difficult to control.

The present invention therefore relates to a method for controlling unwanted plants, in areas of transgenic crop plants being tolerant to HPPD inhibitor herbicides by containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, comprising the application of one or more N-(tetrazol-4-yl)- or N-(triazol-3-yl)arylcarboxamides as defined above to the plants (for example harmful plants such as monocotyledonous or dicotyledonous weeds or undesired crop plants), to the seed (for example grains, seeds or vegetative propagules such as tubers or shoot parts with buds) or to the area on which the plants grow (for example the area under cultivation). Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio,*

Sesbania, Sida, Sinapis, Solanum, Sonchus, Sphenoclea, Stellaria, Taraxacum, Thlaspi, Trifolium, Urtica, Veronica, Viola, Xanthium.

Trangenic crop plants of economically important crops to which the N-(tetrazol-4-yl)- or N-(triazol-3-yl)arylcarboxamides as defined above might be applied are, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*. This is why the present invention preferably relates to the method for controlling unwanted plants, in areas of transgenic crop plants being tolerant to HPPD inhibitor herbicides by containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, comprising the application of one or more N-(tetrazol-4-yl)- or N-(triazol-3-yl)arylcarboxamides as defined above to the plants (for example harmful plants such as monocotyledonous or dicotyledonous weeds or undesired crop plants), to the seed (for example grains, seeds or vegetative propagules such as tubers or shoot parts with buds) or to the area on which the plants grow (for example the area under cultivation) in dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*.

It is preferred to use the N-(tetrazol-4-yl)- or N-(triazol-3-yl)arylcarboxamides as defined above or their salts in economically important transgenic crops of useful plants and ornamentals, for example of cereals such as wheat, barley, rye, oats, sorghum/millet, rice, cassava and maize or else crops of sugar beet, sugar cane, cotton, soybean, oilseed rape, potato, tomato, peas and other vegetables, which crops contain one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

The invention also relates to the use, in a method for transforming plants, of a nucleic acid which encodes an HPPD as a marker gene or as a coding sequence which makes it possible to confer to the plant tolerance to herbicides which are HPPD inhibitors, and the use of N-(tetrazol-4-yl)- or N-(triazol-3-yl)arylcarboxamides as defined above or their salts on plants containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

In the commercial production of crops, it is desirable to eliminate under reliable pesticidal management unwanted plants (i.e., "weeds") from a field of crop plants. An ideal treatment would be one which could be applied to an entire field but which would eliminate only the unwanted plants while leaving the crop plants unaffected. One such treatment system would involve the use of crop plants which are tolerant to an herbicide so that when the herbicide is sprayed on a field of herbicide-tolerant crop plants, the crop plants would continue to thrive while non-herbicide-tolerant weeds are killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

While a number of herbicide-tolerant crop plants are presently commercially available, one issue that has arisen for many commercial herbicides and herbicide/crop combinations is that individual herbicides typically have incomplete spectrum of activity against common weed species. For most individual herbicides which have been in use for some time, populations of herbicide resistant weed species and biotypes have become more prevalent (see, e.g., Tranel and Wright (2002) Weed Science 50: 700-712; Owen and Zelaya (2005) Pest Manag. Sci. 61: 301-311). Transgenic plants which are resistant to more than one herbicide have been described (see, e.g., WO2005/012515). However, improvements in every aspect of crop production, weed control options, extension of residual weed control, and improvement in crop yield are continuously in demand.

The above defined chimeric gene(s) encoding one or more HPPD protein(s) or mutants thereof being functional in transgenic plants in order to perform tolerance to HPPD inhibitor herbicides belonging to the class of N-(tetrazol-4-yl)- or N-(triazol-3-yl)arylcarboxamides as defined above or their salts is/are advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides that, according to their chemical structure, differ from HPPD inhibitor herbicides, and others which confer tolerance to certain insects, those which confer tolerance to certain diseases and or biotic and abiotic stresses, DNAs that encodes RNAs that provide nematode or insect control, etc.

Such genes are in particular described in published PCT Patent Applications WO 91/02071 and WO95/06128.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435), or a gene encoding glyphosate oxydoreductase (U.S. Pat. No. 5,463,175).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO 2004/074443), and which is described in U.S. Pat. No. 6,566,587, hereinafter named double mutant maize EPSPS or 2mEPSPS, or the gene which encodes an EPSPS isolated from *Agrobacterium* and which is described by SEQ ID No. 2 and SEQ ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23(ace3) R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. Nos. 5,510,471 or 5,633,448.

In WO 2007/024782, plants being tolerant to glyphosate and at least one ALS (acetolactate synthase) inhibitor are disclosed. More specifically plants containing genes encoding a GAT (Glyphosate-N-Acetyltransferase) polypeptide and a polypeptide conferring resistance to ALS inhibitors are disclosed.

In U.S. Pat. No. 6,855,533, transgenic tobacco plants containing mutated *Arabidopsis* ALS/AHAS genes were disclosed.

In U.S. Pat. No. 6,153,401, plants containing genes encoding 2,4-D-monooxygenases conferring tolerance to 2,4-D (2,4-dichlorophenoxyacetic acid) by metabolisation are disclosed.

In US 2008/0119361 and US 2008/0120739, plants containing genes encoding Dicamba monooxygenases conferring tolerance to dicamba (3,6-dichloro-2-methoxybenzoic acid) by metabolisation are disclosed.

In WO2011/028833 and WO2011/028832 plants containing genes encoding mutagenized or recombinant Acetyl-coenzyme-A carboylase (ACCase) conferring tolerance to at least one herbicide is selected from the group consisting of alloxydim, butroxydim, clethodim, cloproxydim, cycloxydim, sethoxydim, tepraloxydim, tralkoxydim, chlorazifop, clodinafop, clofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, and pinoxaden or agronomically acceptable salts or esters of any of these herbicides are disclosed.

All the above mentioned herbicide tolerance traits can be combined with those performing HPPD tolerance in plants concerning N-(tetrazol-4-yl)- or N-(triazol-3-yl)arylcarboxamides as defined above or their salts by containing one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO 97/17432 & WO 98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326,169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO02/057664 or toxic fragments thereof, the Cry1A. 105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO 2005/054479 and WO 2005/054480, respectively), the Cry proteins as described in WO01/47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., Waterfield et al., 2001, Appl Environ Microbiol. 67(11): 5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

The present invention also relates to the use of N-(tetrazol-4-yl)- or N-(triazol-3-yl)arylcarboxamides as defined above or their salts in transgenic plants comprising a chimeric gene (or expression cassette) which comprises a coding sequence as well as heterologous regulatory elements, at the 5' and/or 3' position, at least at the 5' position, which are able to function in a host organism, in particular plant cells or plants, with the coding sequence containing at least one nucleic acid sequence which encodes an HPPD (I) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) represents HPPD encoded by a mutated nucleic acid sequence of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

In another particular embodiment, the present invention relates to the use of N-(tetrazol-4-yl)- or N-(triazol-3-yl)arylcarboxamides as defined above or their salts in transgenic plant comprising a chimeric gene as previously described, wherein the chimeric gene contains in the 5' position of the nucleic acid sequence encoding hydroxyphenylpyruvate dioxygenase (HPPD) (I) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) encoded by a mutated nucleic acid sequence of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, a nucleic acid sequence which encodes a plant transit peptide, with this sequence being arranged between the promoter region and the nucleic acid sequence encoding hydroxyphenylpyruvate dioxygenase (HPPD) (I) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) encoded by a mutated nucleic acid sequence of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, so as to permit expression of a transit peptide/HPPD fusion protein.

In a further particular embodiment, the present invention relates to the use of N-(tetrazol-4-yl)- or N-(triazol-3-yl)arylcarboxamides as defined above or their salts on plants, plant parts, or plant seeds containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7 (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, or to the use of N-(tetrazol-4-yl)- or N-(triazol-3-yl)arylcarboxamides as defined above or their salts on soil where such plants, plant parts or seeds are to be grown or sown, either alone or in combination with one or more other known herbicides acting in a different matter to HPPD inhibitors.

In a further particular embodiment, the N-(tetrazol-4-yl)- or N-(triazol-3-yl)arylcarboxamides as defined above or their salts herbicide can applied in combination either in mixture, simultaneously or successively with HPPD inhibitor herbicides selected from the group consisting of triketones (named triketone HPPD inhibitor), such as tembotrione, sulcotrione mesotrione, bicyclopyrone, tefuryltrione, particularly tembotrione, of the class diketone such as diketonitrile of the class of isoxazoles such as isoxaflutole or of the class of pyrazolinates (named pyrazolinate HPPD inhibitor), such as pyrasulfotole, pyrazolate, topramezone, benzofenap, even more specifically present invention relates to the application of tembotrione, mesotrione, diketonitrile, bicyclopyrone, tefuryltrione, benzofenap, pyrasulfotole, pyrazolate and sulcotrione to such HPPD inhibitor tolerant plants, plant parts or plant seeds containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

As a regulatory sequence which functions as a promoter in plant cells and plants, use may be made of any promoter sequence of a gene which is naturally expressed in plants, in particular a promoter which is expressed especially in the leaves of plants, such as for example "constitutive" promoters of bacterial, viral or plant origin, or "light-dependent" promoters, such as that of a plant ribulose-biscarboxylase/oxygenase (RuBisCO) small subunit gene, or any suitable known promoter-expressible which may be used. Among the promoters of plant origin, mention will be made of the histone promoters as described in EP 0 507 698 A1, the rice actin promoter (U.S. Pat. No. 5,641,876), or a plant ubiquitin promoter (U.S. Pat. No. 5,510,474). Among the promoters of a plant virus gene, mention will be made of that of the cauliflower mosaic virus (CaMV 19S or 35S, Sanders et al. (1987), Nucleic Acids Res. 15(4):1543-58.), the circovirus (AU 689 311) or the Cassaya vein mosaic virus (CsVMV, U.S. Pat. No. 7,053,205).

In a further particular embodiment, present invention relates to the use of N-(tetrazol-4-yl)- or N-(triazol-3-yl)arylcarboxamides as defined above or their salts on plants, plant parts, or plant seeds comprising a promoter sequence specific for particular regions or tissues of plants can be used to express one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO 92/17580), the albumin promoter (WO 98/45460), the oleosin promoter (WO 98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO 98/45445).

The genes encoding hydroxyphenylpyruvate dioxygenase (HPPD) (I) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) represented by a mutated DNA sequence of HPPD encoding genes of the before defined organisms, preferably represented by mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 may also be used in combination with the promoter, of other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed 1990, J. Virol. 64: 1590-1597, for example, or introns such as the adh1 intron of maize or intron 1 of rice actin in order to perform a sufficient tolerance to N-(tetrazol-4-yl)- or N-(triazol-3-yl)arylcarboxamides as defined above or their salts.

In a further particular embodiment, the present invention relates to the use of N-(tetrazol-4-yl)- or N-(triazol-3-yl)arylcarboxamides as defined above or their salts on plants, plant parts, or plant seeds containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 and also containing a CYP450 Maize monooxygenase (nsf1 gene) gene being under the control of an identical or different plant expressible promoter in order to confer tolerance to N-(tetrazol-4-yl)- or N-(triazol-3-yl)arylcarboxamides as defined above or their salts.

As a regulatory terminator or polyadenylation sequence, use may be made of any corresponding sequence of bacterial origin, such as for example the nos terminator of *Agrobacterium tumefaciens*, of viral origin, such as for example the CaMV 35S terminator, or of plant origin, such as for example a histone terminator as described in published Patent Application EP 0 633 317 A1.

It is to be understood that in order to obtain an optimized expression by a host adapted codon usage of the respective chimeric gene(s), one could adopt non-planta genes to the codon usage of the respective plant organism in which such chimeric genes will be inserted. Accordingly, in all of the described chimeric genes expressing HPPD of non-planta origin, the respective HPPD encoding DNA sequence can be replaced by an amended DNA sequence encoding the identical amino acid sequence, i.e. SEQ ID No. 3 can be replaced by SEQ ID No. 5, SEQ ID No. 6 can be replaced by SEQ ID No. 18, SEQ ID No. 8 can be replaced by SEQ ID No. 19, SEQ ID No. 10 can be replaced by SEQ ID No. 20, SEQ ID No. 12 can be replaced by SEQ ID No. 21, SEQ ID No. 14 can be replaced by SEQ ID No. 22, SEQ ID No. 16 can be replaced by SEQ ID No. 23.

The term "gene", as used herein refers to a DNA coding region flanked by 5' and/or 3' regulatory sequences allowing a RNA to be transcribed which can be translated to a protein, typically comprising at least a promoter region. A "chimeric gene", when referring to an HPPD encoding DNA, refers to an HPPD encoding DNA sequence having 5' and/or 3' regulatory sequences different from the naturally occurring bacterial 5' and/or 3' regulatory sequences which drive the expression of the HPPD protein in its native host cell (also referred to as "heterologous promoter" or "heterologous regulatory sequences").

The terms "DNA/protein comprising the sequence X" and "DNA/protein with the sequence comprising sequence X", as used herein, refer to a DNA or protein including or containing at least the sequence X in their nucleotide or amino acid sequence, so that other nucleotide or amino acid sequences can be included at the 5' (or N-terminal) and/or 3' (or C-terminal) end, e.g., a N-terminal transit or signal peptide. The term "comprising", as used herein, is open-ended language in the meaning of "including", meaning that other elements then those specifically recited can also be present. The term "consisting of", as used herein, is closed-ended language, i.e., only those elements specifically recited are present. The term "DNA encoding a protein comprising sequence X", as used herein, refers to a DNA comprising a coding sequence which after transcription and translation results in a protein containing at least amino acid sequence X. A DNA encoding a protein need not be a naturally occurring DNA, and can be a semi-synthetic, fully synthetic or artificial DNA and can include introns and 5' and/or 3' flanking regions. The term "nucleotide sequence", as used herein, refers to the sequence of a DNA or RNA molecule, which can be in single- or double-stranded form.

HPPD proteins according to the invention may be equipped with a signal peptide according to procedures known in the art, see, e.g., published PCT patent application WO 96/10083, or they can be replaced by another peptide such as a chloroplast transit peptide (e.g., Van Den Broeck et al., 1985, Nature 313, 358, or a modified chloroplast transit peptide of U.S. Pat. No. 5,510,471) causing transport of the protein to the chloroplasts, by a secretory signal peptide or a peptide targeting the protein to other plastids, mitochondria, the ER, or another organelle, or it can be replaced by a methionine amino acid or by a methionine-alanine dipeptide. Signal sequences for targeting to intracellular organelles or for secretion outside the plant cell or to the cell wall are found in naturally targeted or secreted proteins, preferably those described by Klösgen et al. (1989, Mol. Gen. Genet. 217, 155-161), Klösgen and Weil (1991, Mol. Gen. Genet. 225, 297-304), Neuhaus & Rogers (1998, Plant Mol. Biol. 38, 127-144), Bih et al. (1999, J. Biol. Chem. 274, 22884-22894), Morris et al. (1999, Biochem. Biophys. Res. Commun. 255, 328-333), Hesse et al. (1989, EMBO J. 8 2453-2461), Tavladoraki et al. (1998, FEBS Lett. 426, 62-66), Terashima et al. (1999, Appl. Microbiol. Biotechnol. 52, 516-523), Park et al. (1997, J. Biol. Chem. 272, 6876-6881), Shcherban et al. (1995, Proc. Natl. Acad. Sci. USA 92, 9245-9249), all of which are incorporated herein by reference, particularly the signal peptide sequences from targeted or secreted proteins of corn, cotton, soybean, or rice. A DNA sequence encoding such a plant signal peptide can be inserted in the chimeric gene encoding the HPPD protein for expression in plants.

The invention also encompasses variant HPPD enzymes which are amino acid sequences similar to the HPPD amino acid sequence of SEQ ID No. 2, SEQ ID No. ID No. 4, SEQ ID No. 7, SEQ ID No. 9, SEQ ID No. 11, SEQ ID No. 13, SEQ ID No. 15, and SEQ ID No. 17 wherein in each of the before one or more amino acids have been inserted, deleted or substituted. In the present context, variants of an amino acid sequence refer to those polypeptides, enzymes or proteins which have a similar catalytic activity as the amino acid sequences described herein, notwithstanding any amino acid substitutions, additions or deletions thereto. Preferably the variant amino acid sequence has a sequence identity of at least about 80%, or 85 or 90%, 95%, 97%, 98% or 99% with the amino acid sequence of SEQ ID No. 2, SEQ ID No. 4, SEQ ID No. 7, SEQ ID No. 9, SEQ ID No. 11, SEQ ID No. 13, SEQ ID No. 15, and SEQ ID No. 17, respectively. Also preferably, a polypeptide comprising the variant amino acid sequence has HPPD enzymatic activity. Methods to determine HPPD enzymatic activity are well known in the art and include assays as extensively described in WO 2009/144079 or in WO 2002/046387, or in PCT/EP2010/070561.

Substitutions encompass amino acid alterations in which an amino acid is replaced with a different naturally-occurring or a non-conventional amino acid residue. Such substitutions may be classified as "conservative", in which an amino acid residue contained in an HPPD protein of this invention is replaced with another naturally-occurring amino acid of similar character, for example Gly⇌Ala, Val⇌Ile⇌Leu, Asp⇌Glu, Lys⇌Arg, Asn⇌Gln or Phe⇌Trp⇌Tyr. Substitutions encompassed by the present invention may also be "non-conservative", in which an amino acid residue which is present in an HPPD protein of the invention is substituted with an amino acid with different properties, such as a naturally-occurring amino acid from a different group (e.g. substituting a charged or hydrophobic amino acid with alanine. Amino acid substitutions are typically of single residues, but may be of multiple residues, either clustered or dispersed. Amino acid deletions will usually be of the order of about 1-10 amino acid residues, while insertions may be of any length. Deletions and insertions may be made to the N-terminus, the C-terminus or be internal deletions or insertions. Generally, insertions within the amino acid sequence will be smaller than amino- or carboxy-terminal fusions and of the order of 1 to 4 amino acid residues. "Similar amino acids", as used herein, refers to amino acids that have similar amino acid side chains, i.e. amino acids that have polar, non-polar or practically neutral side chains. "Non-similar amino acids", as used herein, refers to amino acids that have different amino acid side chains, for example an amino acid with a polar side chain is non-similar to an amino acid with a non-polar side chain. Polar side chains usually tend to be present on the surface of a protein where they can interact with the aqueous environment found in cells ("hydrophilic" amino acids). On the other hand, "non-polar" amino acids tend to reside within the center of the protein where they can interact with similar non-polar neighbours ("hydrophobic" amino acids"). Examples of amino acids that have polar side chains are arginine, asparagine, aspartate, cysteine, glutamine, glutamate, histidine, lysine, serine, and threonine (all hydrophilic, except for cysteine which is hydrophobic). Examples of amino acids that have non-polar side chains are alanine, glycine, isoleucine, leucine, methionine, phenylalanine, proline, and tryptophan (all hydrophobic, except for glycine which is neutral).

Unless otherwise stated in the examples, all procedures for making and manipulating recombinant DNA are carried out by the standard procedures described in Sambrook et al., Molecular Cloning—A Laboratory Manual, Second Ed., Cold Spring Harbor Laboratory Press, NY (1989), and in Volumes 1 and 2 of Ausubel et al. (1994) Current Protocols in Molecular Biology, Current Protocols, USA. Standard materials and methods for plant molecular biology work are described in Plant Molecular Biology Labfax (1993) by R.R.D. Croy, jointly published by BIOS Scientific Publications Ltd (UK) and Blackwell Scientific Publications (UK). Procedures for PCR technology can be found in "PCR protocols: a guide to methods and applications", Edited by M. A. Innis, D. H. Gelfand, J. J. Sninsky and T. J. White (Academic Press, Inc., 1990).

The terms "tolerance", "tolerant" or "less sensitive" are interchangeable used and mean the relative levels of inherent tolerance of the HPPD screened according to a visible indicator phenotype of the strain or plant transformed with a nucleic acid comprising the gene coding for the respective HPPD protein in the presence of different concentrations of the various HPPD inhibitor herbicides. Dose responses and relative shifts in dose responses associated with these indicator phenotypes (formation of brown colour, growth inhibition, bleaching, herbicidal effect, etc) are conveniently expressed in terms, for example, of GR50 (concentration for 50% reduction of growth) or MIC (minimum inhibitory concentration) values where increases in values correspond to increases in inherent tolerance of the expressed HPPD, in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD. Herbicides can suitably be applied pre-emergence or post emergence.

Likewise, tolerance level is screened via transgenesis, regeneration, breeding and spray testing of a test plant such as tobacco, or a crop plant such as soybean or cotton and according to these results, such plants are at least 2-4× more tolerant to HPPD inhibitor herbicides, like N-(tetrazol-4-yl)- or N-(triazol-3-yl)arylcarboxamides as defined above or their salts than plants that do not contain any exogenous gene encoding an HPPD protein, "Host organism" or "host" is understood as being any unicellular or multicellular heterologous organism into which the nucleic acid or chimeric gene according to the invention can be introduced for the purpose of producing HPPD. These organisms are, in particular, bacteria, for example *E. coli*, yeast, in particular of the genera *Saccharomyces* or *Kluyveromyces*, *Pichia*, fungi, in particular *Aspergillus*, a baculovirus or, preferably, plant cells and plants.

"Plant cell" is understood, according to the invention, as being any cell which is derived from or found in a plant and which is able to form or is part of undifferentiated tissues, such as calli, differentiated tissues such as embryos, parts of plants, plants or seeds. This includes protoplasts and pollen, cultivated plants cells or protoplasts grown in vitro, and plant cells that can regenerate into a complete plant.

"Plant" is understood, according to the invention, as being any differentiated multicellular organism which is capable of photosynthesis, in particular a monocotyledonous or dicotyledonous organism, more especially cultivated plants which are or are not intended for animal or human nutrition, such as maize or corn, wheat, *Brassica* spp. plants such as *Brassica napus* or *Brassica juncea*, soya spp, rice, sugarcane, beetroot, tobacco, cotton, vegetable plants such as cucumber, leek, carrot, tomato, lettuce, peppers, melon, watermelon, etc. Transgenic plants, as used herein, refer to plants comprising one or more foreign or heterologous gene(s) stably inserted in their genome.

In order perform tolerance to N-(tetrazol-4-yl)- or N-(triazol-3-yl)arylcarboxamides as defined above or their salts, any promoter sequence of a gene which is expressed naturally in plants, or any hybrid or combination of promoter elements of genes expressed naturally in plants, including *Agrobacterium* or plant virus promoters, or any promoter which is suitable for controlling the transcription of a herbicide tolerance gene in plants, can be used as the promoter sequence in the plants of the invention (named "plant-expressible promoter" herein). Examples of such suitable plant-expressible promoters are described above. In one embodiment of this invention, such plant-expressible promoters are operably-linked to a (I) DNA sequence encoding hydroxyphenylpyruvate dioxygenase (HPPD) that is derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) a mutated DNA sequence of HPPD of the before defined organisms, preferably a mutated DNA sequence as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 and also containing.

According to the invention, it is also possible to use, in combination with the promoter regulatory sequence, other regulatory sequences which are located between the promoter and the coding sequence, such as intron sequences, or transcription activators (enhancers) in order to perform tolerace to N-(tetrazol-4-yl)- or N-(triazol-3-yl)arylcarboxamides as defined above or their salts. Examples of such suitable regulatory sequences are described above.

Any corresponding sequence of bacterial or viral origin, such as the nos terminator from *Agrobacterium tumefaciens*, or of plant origin, such as a histone terminator as described in application EP 0 633 317 A1, may be used as transcription termination (and polyadenylation) regulatory sequence.

In a further particular embodiment, the present invention relates to the use of N-(tetrazol-4-yl)- or N-(triazol-3-yl)arylcarboxamides as defined above or their salts on plants, plant parts, or plant seeds containing a nucleic acid sequence which encodes a transit peptide is employed 5' (upstream) of the nucleic acid sequence encoding the exogenous chimeric gene (s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 and also containing with this transit peptide sequence being arranged between the promoter region and the sequence encoding the exogenous HPPD so as to permit expression of a transit peptide-HPPD fusion protein. The transit peptide makes it possible to direct the HPPD into the plastids, more especially the chloroplasts, with the fusion protein being cleaved between the transit peptide and the HPPD protein when the latter enters the plastid. The transit peptide may be a single peptide, such as an EPSPS transit peptide (described in U.S. Pat. No. 5,188,642) or a transit peptide of the plant ribulose bisphosphate carboxylase/oxygenase small subunit (RuBisCO ssu), where appropriate, including a few amino acids of the N-terminal part of the mature RuBisCO ssu (EP 189 707 A1), or else may be a fusion of several transit peptides such as a transit peptide which comprises a first plant transit peptide which is fused to a part of the N-terminal sequence of a mature protein having a plastid location, with this part in turn being fused to a second plant transit peptide as described in patent EP 508 909 A1, and, more especially, the optimized transit peptide which comprises a transit peptide of the sunflower RuBisCO ssu fused to 22 amino acids of the N-terminal end of the maize RuBisCO ssu, in turn fused to the transit peptide of the maize RuBisCO ssu, as described, with its coding sequence, in patent EP 508 909 A1.

The present invention also relates to the transit peptide HPPD fusion protein and a nucleic acid or plant-expressible chimeric gene encoding such fusion protein, wherein the two elements of this fusion protein are as defined above.

In a further particular embodiment, the present invention relates to the use of N-(tetrazol-4-yl)- or N-(triazol-3-yl)arylcarboxamides as defined above or their salts on plants, plant parts, or plant seeds obtained by cloning, transformation with a expression vector, which expression vector contains at least one chimeric gene encoding the hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575. In addition to the above chimeric gene, this vector can contain an origin of replication. This vector can be a plasmid or plasmid portion, a cosmid, or a bacteriophage or a virus which has been transformed by introducing the chimeric gene according to the invention. Transformation vectors are well known to the skilled person and widely described in the literature. The transformation vector which can be used, in particular, for transforming plant cells or plants may be a virus, which can be employed for transforming plant cells or plants and which additionally contains its own replication and expression elements. The vector for transforming plant cells or plants is preferably a plasmid, such as a disarmed *Agrobacterium* Ti plasmid.

In a further particular embodiment, the present invention relates to the use of N-(tetrazol-4-yl)- or N-(triazol-3-yl)arylcarboxamides as defined above or their salts on plants, plant parts, or plant seeds containing a chimeric gene which comprises a sequence encoding the hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, and the use of the plants or seeds in a field to grow a crop and harvest a plant product, e.g., soya spp, rice, wheat, barley or corn grains or cotton bolls, where in one embodiment said use involves the application of an N-(tetrazol-4-yl)- or N-(triazol-3-yl)arylcarboxamides as defined above or their salts to such plants to control weeds.

In another particular embodiment, the present invention relates to the use of N-(tetrazol-4-yl)- or N-(triazol-3-yl)arylcarboxamides as defined above or their salts on plants, plant parts, or plant seeds characterized in that it contains one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, and in addition further contains a chimeric gene comprising a plant-expressible promoter as described above, operably-linked to a nucleic acid sequence encoding a PDH (prephenate dehydrogenase) enzyme (US 2005/0257283) in order to confer tolerance to N-(tetrazol-4-yl)- or N-(triazol-3-yl)arylcarboxamides as defined above or their salts. A plant comprising such two transgenes can be obtained by transforming a plant with one transgene, and then re-transforming this transgenic plant with the second transgene, or by transforming a plant with the two transgenes simultaneously (in the same or in 2 different transforming DNAs or vectors), or by crossing a plant comprising the first transgene with a plant comprising the second transgene, as is well known in the art.

One transformation method in order to obtain plants, plant parts or seeds being tolerant to N-(tetrazol-4-yl)- or N-(triazol-3-yl)arylcarboxamides as defined above or their salts by containing one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/

070578, PCT/EP2010/070570, or PCT/EP2010/070575 comprises bombarding cells, protoplasts or tissues with solid or liquid particles to which DNA is attached, or containing DNA. Another transformation method comprises using, as mean for transfer into the plant, a chimeric gene which is inserted into an *Agrobacterium tumefaciens* Ti plasmid or an *Agrobacterium rhizogenes* Ri plasmid. Other methods may be used, such as microinjection or electroporation or otherwise direct gene transfer using PEG. The skilled person can select any appropriate method for transforming the host organism of choice, in particular the plant cell or the plant. As examples, the technology for soybean transformation has been extensively described in the examples 1 to 3 disclosed in EP 1186666 A1, incorporated herein by reference. For rice, *Agrobacterium*-mediated transformation (Hiei et al., 1994 Plant J 6:271-282, and Hiei et al., 1997 Plant Mol. Biol. 35:205-21, incorporated herein by reference), electroporation (U.S. Pat. Nos. 5,641,664 and 5,679,558, incorporated herein by reference), or bombardment (Christou et al., 1991, Biotechnology 9:957 incorporated herein by reference) could be performed. A suitable technology for transformation of monocotyledonous plants, and particularly rice, is described in WO 92/09696, incorporated herein by reference. For cotton, *Agrobacterium*-mediated transformation (Gould J. H. and Magallanes-Cedeno M., 1998 Plant Molecular Biology reporter, 16:1-10 and Zapata C., 1999, Theoretical Applied Genetics, 98(2):1432-2242 incorporated herein by reference), polybrene and/or treatment-mediated transformation (Sawahel W. A., 2001, Plant Molecular Biology reporter, 19:377a-377f, incorporated herein by reference) have been described.

Alternatively, N-(tetrazol-4-yl)- or N-(triazol-3-yl)arylcarboxamides as defined above or their salts may be used on plants, plant parts, or plant seeds containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 which HPPD is expressed directly in the plastids, such as the chloroplasts, using transformation of the plastid, such as the chloroplast genome. A suitable method comprises the bombardment of plant cells or tissue by solid particles coated with the DNA or liquid particles comprising the DNA, and integration of the introduced gene by homologous recombination. Suitable vectors and selection systems are known to the person skilled in the art. An example of means and methods which can be used for such integration into the chloroplast genome of tobacco plants is given in WO 06/108830, the content of which is hereby incorporated by reference The present invention also relates to a method for obtaining a plant tolerant to N-(tetrazol-4-yl)- or N-(triazol-3-yl)arylcarboxamides as defined above or their salts, characterized in that the plant is transformed with one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

Therefore, the present invention also relates to a method for obtaining a plant tolerant to N-(tetrazol-4-yl)- or N-(triazol-3-yl)arylcarboxamides as defined above or their salts by containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, characterized in that the plant contains one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, which comprises a coding sequence as well as a heterologous regulatory element in the 5' and optionally in the 3' positions, which are able to function in a host organism, characterized in that the coding sequence comprises at least a nucleic acid sequence defining a gene encoding an HPPD of the invention as previously described in order to perform a sufficiently high level of tolerance to N-(tetrazol-4-yl)- or N-(triazol-3-yl)arylcarboxamides as defined above or their salts.

In one embodiment of this invention, the HPPD inhibitor in the above method is a N-(tetrazol-4-yl)- or N-(triazol-3-yl) arylcarboxamides as defined above or their salts either alone or in combination with one or more HPPD inhibitor herbicides selected from the group consisting of triketone or pyrazolinate herbicide, preferably tembotrione, mesotrione, bicyclopyrone, tefuryltrione pyrasulfotole, pyrazolate, diketonitrile, benzofenap, or sulcotrione, particularly tembotrione.

The invention also relates to a method for selectively removing weeds or preventing the germination of weeds in a field to be planted with plants or to be sown with seeds, or in a plant crop, by application of a N-(tetrazol-4-yl)- or N-(triazol-3-yl)arylcarboxamides as defined above or their salts to such field or plant crop, which method is characterized in that this N-(tetrazol-4-yl)- or N-(triazol-3-yl)arylcarboxamides as defined above or their salts is applied to plants which have been transformed in accordance with one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, either before sowing the crop (hereinafter named pre-planting application), before emergence of the crop (hereinafter named pre-emergence application), or after emergence of the crop (hereinafter named post-emergence application).

The invention also relates to a method for controlling in an area or a field which contains transformed seeds as previously described in the present invention, which method comprises applying, to the said area of the field, a dose of an N-(tetrazol-4-yl)- or N-(triazol-3-yl)arylcarboxamides as defined above or their salts which is toxic for the said weeds, without significantly affecting the seeds or plants containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575.

The present invention also relates to a method for cultivating the plants which have been transformed with one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, which method comprises planting seeds comprising a chimeric gene of before, in an area of a field which is appropriate for cultivating the said plants, and in applying, if weeds are present, a dose, which is toxic for the weeds, of one or more N-(tetrazol-4-yl)- or N-(triazol-3-yl)arylcarboxamides as defined above or their salts to the said area of the said field, without significantly affecting the said transformed seeds or the said transformed plants, and in then harvesting the cultivated plants or plant parts when they reach the desired stage of maturity and, where appropriate, in separating the seeds from the harvested plants.

In the above methods, the N-(tetrazol-4-yl)- or N-(triazol-3-yl)arylcarboxamides as defined above or their salts can be applied in accordance with the invention, either before sowing the crop, before the crop emerges or after the crop emerges.

Within the meaning of the present invention, "herbicide" is understood as being a herbicidally active substance on its own or such a substance which is combined with an additive which alters its efficacy, such as, for example, an agent which increases its activity (a synergistic agent) or which limits its activity (a safener). It is of course to be understood that, for their application in practice, the above herbicides are combined, in a manner which is known per se, with the formulation adjuvants which are customarily employed in agricultural chemistry.

Thus, transgenic plants can be obtained which—in addition to the one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7 (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575— have modified properties as the result of overexpression, suppression or inhibition of homologous (=natural) genes or gene sequences or expression of heterologous (=foreign) genes or gene sequences.

On the plants, plant cells or seeds containing one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11, or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, it is preferred to employ one or more of the N-(tetrazol-4-yl)- or N-(triazol-3-yl)arylcarboxamides as defined above or their salts in combination with one or more further HPPD inhibitor herbicides belonging to the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione in transgenic crops which are also resistant to growth regulators such as, for example, 2,4-D or dicamba, or against herbicides which inhibit essential plant enzymes, for example acetolactate synthases (ALS), EPSP synthases, glutamine synthases (GS), Acetyl-coenzyme A carboxylase (ACCase), or against herbicides from the group of the sulfonylureas, imidazolinones, glyphosate, glufosinate, ACCase inhibitors and analogous active substances.

The invention therefore also relates to the use of herbicides applied to HPPD tolerant plants containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 for controlling harmful plants (i.e. weeds) which also extends to transgenic crop plants comprising a second or more herbicide resistance(s) beside the resistance against one or more N-(tetrazol-4-yl)- or N-(triazol-3-yl)arylcarboxamides as defined above or their salts.

N-(tetrazol-4-yl)- or N-(triazol-3-yl)arylcarboxamides as defined above or their salts can be formulated in various ways, depending on the prevailing biological and/or physicochemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Kuchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxiddadukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Wettable powders are preparations which are uniformly dispersible in water and which, besides the active substance, also comprise ionic and/or nonionic surfactants (wetters, dispersers), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, besides a diluent or inert substance. To prepare the wettable powders, the herbicidally active substances are ground finely, for example in customary apparatuses such as hammer mills, blower mills and air-jet mills, and mixed with the formulation auxiliaries, either simultaneously or subsequently.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials such as, for example, talcum, natural clays such as kaolin, bentonite and pyrophyllite, or diatomaceous earth.

Suspension concentrates can be water- or oil-based. They can be prepared for example by wet-grinding by means of commercially available bead mills, if appropriate with addition of surfactants as already listed above for example in the case of the other formulation types.

Emulsions, for example oil-in-water emulsions (EW), can be prepared for example by means of stirrers, colloid mills and/or static mixers using aqueous organic solvents and, if appropriate, surfactants, as have already been mentioned for example above for the other formulation types.

Granules can be prepared either by spraying the active substance onto adsorptive, granulated inert material, or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the manner which is customary for the production of fertilizer granules, if desired as a mixture with fertilizers.

Water-dispersible granules are generally prepared by customary methods such as spray drying, fluidized-bed granulation, disk granulation, mixing with high-speed stirrers, and extrusion without solid inert material.

To prepare disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineers Handbook", 5th Ed., McGraw-Hill, New York 1973, p. 8-57.

For further details of the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise from 0.1 to 99% by weight, in particular from 0.1 to 95% by weight, of compounds according to the invention. In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise from 1 to 30% by weight of active substance, preferably in most cases from 5 to 20% by weight of active substance, and sprayable solutions comprise approximately from 0.05 to 80, preferably from 2 to 50% by weight of active substance. In the case of water-dispersible granules, the active substance content depends partly on whether the active compound is in liquid or solid form, and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrations, preservatives, antifreeze agents, solvents, fillers, carriers, colorants, antifoams, evaporation inhibitors, and pH and viscosity regulators.

Based on these formulations, it is also possible to prepare combinations of an HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione with other pesticidally active substances such as, for example, insecticides, acaricides, herbicides, fungicides, and with safeners, fertilizers and/or growth regulators, for example in the form of a ready mix or a tank mix to be applied to HPPD tolerant plants according to the invention.

FORMULATION EXAMPLES a) A dust is obtained by mixing 10 parts by weight of a compound of the formula (I) and/or a salt thereof and 90 parts by weight of talc as inert substance and comminuting the mixture in a hammer mill.

b) A wettable powder which is readily dispersible in water is obtained by mixing 25 parts by weight of a compound of the formula (I) and/or a salt thereof, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A readily water-dispersible dispersion concentrate is obtained by mixing 20 parts by weight of a compound of the formula (I) and/or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or a salt thereof, 75 parts by weight of cyclohexanone as solvent and 10 parts by weight of oxethylated nonylphenol as emulsifier.

e) Water-dispersible granules are obtained by mixing
   75 parts by weight of a compound of the formula (I) and/or a salt thereof,
   10 parts by weight of calcium lignosulfonate,
   5 parts by weight of sodium lauryl sulfate,
   3 parts by weight of polyvinyl alcohol and
   7 parts by weight of kaolin,
   grinding the mixture in a pinned-disk mill, and granulating the powder in a fluidized bed by spraying on water as granulating liquid.

f) Water-dispersible granules are also obtained by homogenizing and precomminuting, in a colloid mill,
   25 parts by weight of a compound of the formula (I) and/or a salt thereof,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance nozzle.

A further aspect of present invention is the use of one or more N-(tetrazol-4-yl)- or N-(triazol-3-yl)arylcarboxamides as defined above or their salts to HPPD tolerant plants containing one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 in combination with further HPPD inhibitor herbicide belonging to the class of triketones, such as tembotrione, sulcotrione and mesotrione, or belonging to the class of pyrazolinates, such as pyrasulfotole and topramezone, particularly selected from tembotrione, sulcotrione, topramezone, bicyclopyrone, tefuryltrione and mesotrione, more particularly tembotrione in mixed formulations or in the tank mix, and/or with further known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active substances (the compounds are either designated by the common name according to the International Organization for Standardization (ISO) or by a chemical name, if appropriate together with the code number) and always comprise all use forms such as acids, salts, esters and isomers such as stereoisomers and optical isomers. In this context, one and in some cases also several use forms are mentioned by way of example:
acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlorotoluron, chlorsulfuron, cinidon, cinidon-ethyl, cinmethylin, cinosulfuron, clethodim, clodinafop clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), di-allate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoro-propyl)-4,5-dihydro-5-oxo-1H-tetrazol-1-yl]-phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P- potassium, mefenacet, mefluidide, mepiquat-chloride, mesosulfuron, mesosulfuron-methyl, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogen sulfate, monolinuron, monosulfuron, monuron, MT 128, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulf-allate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tepraloxydim, terbacil, terbucarb, terbuchlor, terbumeton, terbuthylazine, terbutryne, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, tralkoxydim, tri-allate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

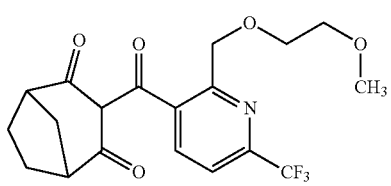

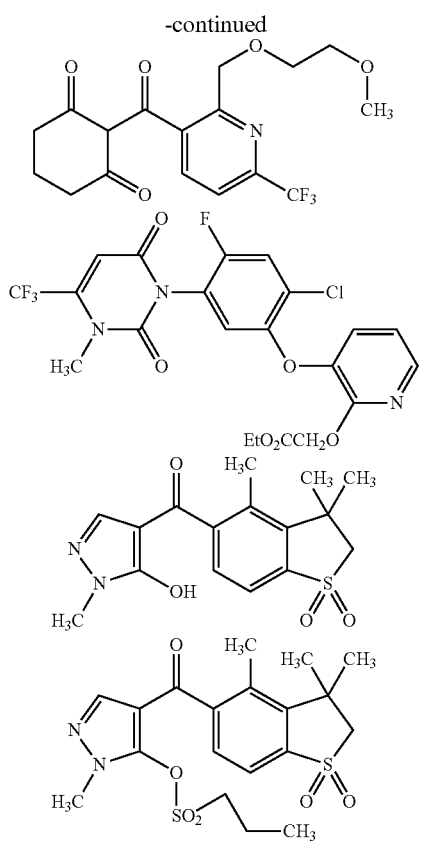

The application rate required of an N-(tetrazol-4-yl)- or N-(triazol-3-yl)arylcarboxamides as defined above or their salts to be applied to areas where HPPD tolerant plants containing one or more chimeric gene(s) (I) comprising a DNA sequence encoding hydroxyphenylpyruvate dioxygenase (HPPD) derived from a member of a group of organisms consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17, or (II) comprising one or more mutated DNA sequences of HPPD encoding genes of the before defined organisms, preferably mutants as described in WO 2010/085705, U.S. Pat. No. 6,245,968, WO 2009/144079, PCT/

EP2010/070561, PCT/EP2010/070567, PCT/EP2010/070578, PCT/EP2010/070570, or PCT/EP2010/070575 are growing varies as a function of the external conditions such as temperature, humidity, the nature of the herbicide used and the like. It can vary within wide limits, for example between 0.001 and 1.0 kg/ha and more of active substance, but it is preferably between 0.005 and 750 g/ha.

In case of combined applications of N-(tetrazol-4-yl)- or N-(triazol-3-yl)arylcarboxamides as defined above or their salts herbicides that differ from N-(tetrazol-4-yl)- or N-(triazol-3-yl)arylcarboxamides as defined above or their salts to the HPPD tolerant plants containing one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575, these mixtures may cause crop injury, based on the presence herbicides different to N-(tetrazol-4-yl)- or N-(triazol-3-yl)arylcarboxamides as defined above or their salts. In order to reduce/eliminate such crop injuries, appropriate safeners may be added. These safeners, which are employed in antidotically active amounts, reduce the phytotoxic side effects of herbicides/pesticides used, for example in economically important crops, such as cereals (wheat, barley, rye, corn, rice, millet), alfalfa, sugar beet, sugarcane, oilseed rape, cotton and soya spp., preferably corn, cotton, sugarbeet, or soya spp.

The safeners are preferably selected from the group consisting of:

A) compounds of the formula (S-I)

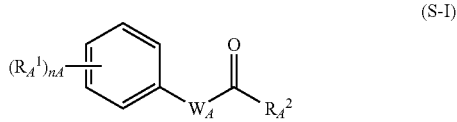

where the symbols and indices have the following meanings:

$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group consisting of partially unsaturated or aromatic five-membered heterocycles having 1 to 3 hetero ring atoms of the type N or O, where at least one nitrogen atom and at most one oxygen atom is present in the ring, preferably a radical from the group consisting of $(W_A^1)$ to $(W_A^4)$,

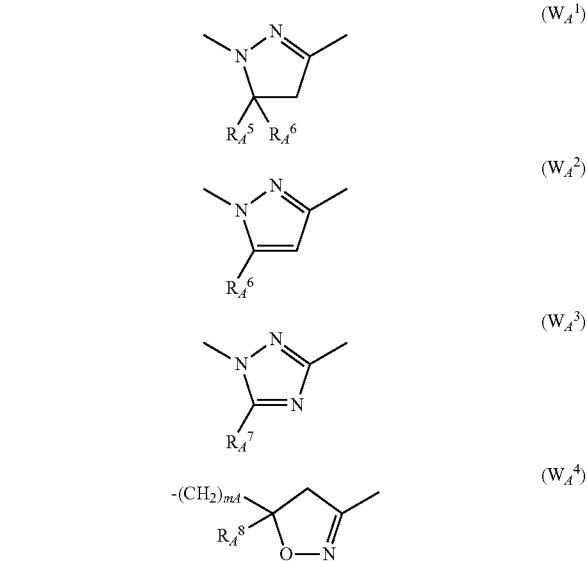

$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S-I) and which is unsubstituted or substituted by radicals from the group consisting of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;
$R_A^3$ is hydrogen or an unsubstituted or substituted aliphatic hydrocarbon radical having preferably a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;
$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:
a) compounds of the type of the dichlorophenylpyrazoline-3-carboxylic acid, preferably compounds such as ethyl 1-(2,4-dichlorophenyl)-5-(ethoxycarbonyl)-5-methyl-2-pyrazoline-3-carboxylate (S1-1) ("mefenpyr-diethyl", see Pestic. Man.), and related compounds, as described in WO 91/07874;
b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds, as described in EP-A-333 131 and EP-A-269 806;

c) compounds of the type of the triazolecarboxylic acids, preferably compounds such as fenchlorazole(-ethyl ester), i.e. ethyl 1-(2,4-dichlorophenyl)-5-trichloro-methyl-(1H)-1,2,4-triazole-3-carboxylate (S1-6), and related compounds, as described in EP-A-174 562 and EP-A-346 620;

d) compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as described in the patent application WO-A-95/07897.

B) Quinoline derivatives of the formula (S-II)

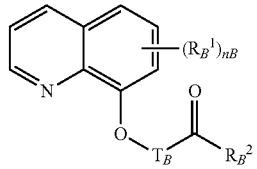

(S-II)

where the symbols and indices have the following meanings:
$R_B^3$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ $OR_B^3$, $SR_B^3$ or $NR_B^3 R_B^4$ or a saturated
or unsaturated 3- to 7-membered heterocycle having at least one nitrogen atom and up to 3 heteroatoms, preferably from the group consisting of O and S, which is attached via the nitrogen atom to the carbonyl group in (S-II) and is unsubstituted or substituted by radicals from the group consisting of $(C_1-C_4)$-alkyl, $(C_1-C_4)$-alkoxy or optionally substituted phenyl, preferably a radical of the formula $OR_B^3$, $NHR_B^4$ or $N(CH_3)_2$, in particular of the formula $OR_B^3$;
$R_B^3$ is hydrogen or an unsubstituted or substituted aliphatic hydrocarbon radical having preferably a total of 1 to 18 carbon atoms;
$R_B^4$ is hydrogen, $(C_1-C_6)$-alkyl, $(C_1-C_6)$-alkoxy or substituted or unsubstituted phenyl;
$T_B$ is a $(C_1-$ or $C_2)$-alkanediyl chain which is unsubstituted or substituted by one or two $(C_1-C_4)$-alkyl radicals or by $[(C_1-C_3)$-alkoxy]carbonyl;
preferably:

a) compounds of the type of the 8-quinolinoxyacetic acid (S2), preferably 1-methylhexyl (5-chloro-8-quinolinoxy) acetate (common name "cloquintocet-mexyl" (S2-1) (see Pestic. Man.), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also their hydrates and salts, as described in WO-A-2002/034048.

b) Compounds of the type of the (5-chloro-8-quinolinoxy) malonic acid, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

C) Compounds of the formula (S-III)

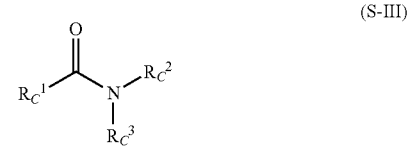

(S-III)

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring,
preferably an oxazolidine, thiazolidine, piperidine, morpholine, hexahydropyrimidine or benzoxazine ring;
preferably:

Active compounds of the type of the dichloroacetamides which are frequently used as pre-emergence safener (soil-acting safeners), such as, for example, "dichlormid" (see Pestic.Man.) (=N,N-diallyl-2,2-dichloroacetamide),
"R-29148" (=3-dichloroacetyl-2,2,5-trimethyl-1,3-oxazolidine from Stauffer), "R-28725" (=3-dichloroacetyl-2,2,-dimethyl-1,3-oxazolidine from Stauffer), "benoxacor" (see Pestic. Man.) (=4-dichloroacetyl-3,4-dihydro-3-methyl-2H-1,4-benzoxazine),
"PPG-1292" (=N-allyl-N-[(1,3-dioxolan-2-Amethyl]dichloroacetamide from PPG Industries),
"DKA-24" (=N-allyl-N-[(allylaminocarbonyl)methyl] dichloroacetamide from Sagro-Chem),
"AD-67" or "MON 4660" (=3-dichloroacetyl-1-oxa-3-azaspiro[4,5]decane from Nitrokemia or Monsanto),
"TI-35" (=1-dichloroacetylazepane from TRI-Chemical RT)
"diclonon" (dicyclonone) or "BAS145138" or "LAB145138" (=3-dichloroacetyl-2,5,5-trimethyl-1,3-diazabicyclo[4.3.0]nonane from BASF) and
"furilazole" or "MON 13900" (see Pestic. Man.) (=(RS)-3-dichloroacetyl-5-(2-furyl)-2,2-dimethyloxazolidine).

D) N-Acylsulfonamides of the formula (I-IV) and their salts

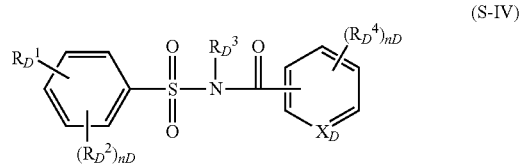

(S-IV)

in which
$X_D$ is CH or N;
$R_D^1$ is CO—$NR_D^5 R_D^6$ or NHCO—$R_D^7$;
$R_D^2$ is halogen, ($C_1$-$C_4$)-haloalkyl, ($C_1$-$C_4$)-haloalkoxy, nitro, ($C_1$-$C_4$)-alkyl, ($C_1$-$C_4$)-alkoxy, ($C_1$-$C_4$)-alkylsulfonyl, ($C_1$-$C_4$)-alkoxycarbonyl or ($C_1$-$C_4$)-alkylcarbonyl;
$R_D^3$ is hydrogen, ($C_1$-$C_4$)-alkyl, ($C_2$-$C_4$)-alkenyl or ($C_2$-$C_4$)-alkynyl;
$R_D^4$ is halogen, nitro, ($C_1$-$C_4$)-alkyl, ($C_1$-$C_4$)-haloalkyl, ($C_1$-$C_4$)-haloalkoxy, ($C_3$-$C_6$)-cycloalkyl, phenyl, ($C_1$-$C_4$)-alkoxy, cyano, ($C_1$-$C_4$)-alkylthio, ($C_1$-$C_4$)-alkylsulfinyl, ($C_1$-$C_4$)-alkylsulfonyl, ($C_1$-$C_4$)-alkoxycarbonyl or ($C_1$-$C_4$)-alkylcarbonyl;
$R_D^5$ is hydrogen, ($C_1$-$C_6$)-alkyl, ($C_3$-$C_6$)-cycloalkyl, ($C_2$-$C_6$)-alkenyl, ($C_2$-$C_6$)-alkynyl, ($C_5$-$C_6$)-cycloalkenyl, phenyl or 3- to 6-membered heterocyclyl containing $V_D$ heteroatoms from the group consisting of nitrogen, oxygen and sulfur, where the seven last-mentioned radicals are substituted by $v_D$ substituents from the group consisting of halogen, ($C_1$-$C_6$)-alkoxy, ($C_1$-$C_6$)-haloalkoxy, ($C_1$-$C_2$)-alkylsulfinyl, ($C_1$-$C_2$)-alkylsulfonyl, ($C_3$-$C_6$)-cycloalkyl, ($C_1$-$C_4$)-alkoxycarbonyl, ($C_1$-$C_4$)-alkylcarbonyl and phenyl and, in the case of cyclic radicals, also ($C_1$-$C_4$)-alkyl and ($C_1$-$C_4$)-haloalkyl;
$R_D^6$ is hydrogen, ($C_1$-$C_6$)-alkyl, ($C_2$-$C_6$)-alkenyl or ($C_2$-$C_6$)-alkynyl, where the three last-mentioned radicals are substituted by $v_D$ radicals from the group consisting of halogen, hydroxy, ($C_1$-$C_4$)-alkyl, ($C_1$-$C_4$)-alkoxy and ($C_1$-$C_4$)-alkylthio, or
$R_D^5$ and $R_D^6$ together with the nitrogen atom carrying them form a pyrrolidinyl or piperidinyl radical;
$R_D^7$ is hydrogen, ($C_1$-$C_4$)-alkylamino, di-($C_1$-$C_4$)-alkylamino, ($C_1$-$C_6$)-alkyl, ($C_3$-$C_6$)-cycloalkyl, where the 2 last-mentioned radicals are substituted by $v_D$ substituents from the group consisting of halogen, ($C_1$-$C_4$)-alkoxy, halogen-($C_1$-$C_6$)-alkoxy and ($C_1$-$C_4$)-alkylthio and, in the case of cyclic radicals, also ($C_1$-$C_4$)-alkyl and ($C_1$-$C_4$)-haloalkyl;
$n_D$ is 0, 1 or 2;
$m_D$ is 1 or 2;
$v_D$ is 0, 1, 2 or 3;
from among these, preference is given to compounds of the type of the N-acylsulfonamides, for example of the formula (S-V) below, which are known, for example, from WO 97/45016

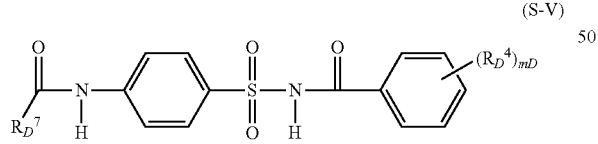

(S-V)

in which
$R_D^7$ is ($C_1$-$C_6$)-alkyl, ($C_3$-$C_6$)-cycloalkyl, where the 2 last-mentioned radicals are substituted by $v_D$ substituents from the group consisting of halogen, ($C_1$-$C_4$)-alkoxy, halogen-($C_1$-$C_6$)-alkoxy and ($C_1$-$C_4$)-alkylthio and, in the case of cyclic radicals, also ($C_1$-$C_4$)-alkyl and ($C_1$-$C_4$)-haloalkyl;
$R_D^4$ is halogen, ($C_1$-$C_4$)-alkyl, ($C_1$-$C_4$)-alkoxy, $CF_3$,
$m_D$ is 1 or 2;
$v_D$ is 0, 1, 2 or 3;
and also
acylsulfamoylbenzamides, for example of the formula (S-VI) below, which are known, for example from WO 99/16744,

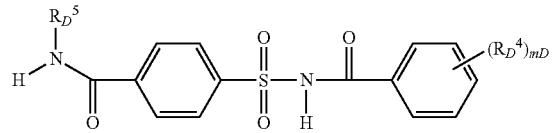

(S-VI)

for example those in which
$R_D^5$=cyclopropyl and ($R_D^4$)=2-OMe ("cyprosulfamide", S3-1),
$R_D^5$=cyclopropyl and ($R_D^4$)=5-Cl-2-OMe (S3-2),
$R_D^5$=ethyl and ($R_D^4$)=2-OMe (S3-3),
$R_D^5$=isopropyl and ($R_D^4$)=5-Cl-2-OMe (S3-4) and
$R_D^5$=isopropyl and ($R_D^4$)=2-OMe (S3-5);
and also
compounds of the type of the N-acylsulfamoylphenylureas of the formula (S-VII), which are known, for example, from EP-A-365484

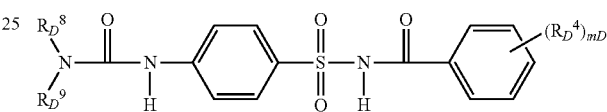

(S-VII)

in which
$R_D^8$ and $R_D^9$ independently of one another are hydrogen, ($C_1$-$C_8$)-alkyl, ($C_3$-$C_8$)-cycloalkyl, ($C_3$-$C_6$)-alkenyl, ($C_3$-$C_6$)-alkynyl,
$R_D^4$ is halogen, ($C_1$-$C_4$)-alkyl, ($C_1$-$C_4$)-alkoxy, $CF_3$
$m_D$ is 1 or 2;
from among these in particular
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
G) active compounds from the class of the hydroxyaromatics and aromatic-aliphatic carboxylic acid derivatives, for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 1,2-dihydro-2-oxo-6-trifluoromethylpyridine-3-carboxamide, 2-hydroxycinnamic acid, 2,4-dichlorocinnamic acid, as described in WO 2004084631, WO 2005015994, WO 2006007981, WO 2005016001;
H) active compounds from the class of the 1,2-dihydroquinoxalin-2-ones, for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO 2005112630,
I) active compounds which, in addition to a herbicidal action against harmful plants, also have safener action on crop plants such as rice, such as, for example,
"dimepiperate" or "MY-93" (see Pestic. Man.) (=S-1-methyl-1-phenylethyl piperidine-1-thiocarboxylate), which is known as safener for rice against damage by the herbicide molinate, "daimuron" or "SK 23" (see Pestic. Man.) (=1-(1-methyl-1-phenylethyl)-3-p-tolyl-urea), which is known as safener for rice against damage by the herbicide imazosulfuron, "cumyluron"="JC-940" (=3-(2-chlorophenylmethyl)-1-(1-methyl-1-phenyl-ethyl)urea, see JP-A-60087254), which is known as safener for rice against damage by a number of herbicides, "methoxyphenone" or "NK 049" (=3,3'-dimethyl-4-methoxybenzophenone), which is known as safener for rice against damage by a number of herbicides, "CSB" (=1-bromo-4-(chloromethylsulfonyl)benzene) (CAS Reg. No. 54091-06-4 from Kumiai), which is known as safener against damage by a number of herbicides in rice, K) compounds of the formula (S-IX),
as described in WO-A-1998/38856

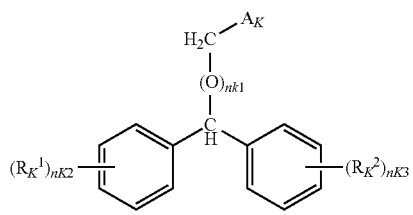

(S-IX)

in which the symbols and indices have the following meanings:

$R_K^1$, $R_K^2$ independently of one another are halogen, $(C_1$-$C_4)$-alkyl, $(C_1$-$C_4)$-alkoxy, $(C_1$-$C_4)$-haloalkyl, $(C_1$-$C_4)$-alkylamino, di-$(C_1$-$C_4)$-alkylamino, nitro;

$A_K$ is $COOR_K^3$ or $COOR_K^4$ $R_K^3$, $R_K^4$ independently of one another are hydrogen, $(C_1$-$C_4)$-alkyl, $(C_2$-$C_6)$-alkenyl, $(C_2$-$C_4)$-alkynyl, cyanoalkyl, $(C_1$-$C_4)$-haloalkyl, phenyl, nitrophenyl, benzyl, halobenzyl, pyridinylalkyl or alkylammonium, $n_K^1$ is 0 or 1, $n_K^2$, $n_K^3$ independently of one another are 0, 1 or 2 preferably: methyl (diphenylmethoxy)acetate (CAS Reg. No.: 41858-19-9),

L) compounds of the formula (S-X), as described in WO A-98/27049

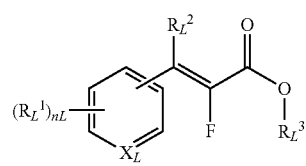

(S-X)

in which the symbols and indices have the following meanings:

$X_L$ is CH or N, $n_L$ is, in the case that X=N, an integer from 0 to 4 and, in the case that X=CH, an integer from 0 to 5, $R_L^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy, nitro, $(C_1$-$C_4)$-alkylthio, $(C_1$-$C_4)$-alkylsulfonyl, $(C_1$-$C_4)$-alkoxycarbonyl, optionally substituted phenyl, optionally substituted phenoxy, $R_L^2$ is hydrogen or $(C_1$-$C_4)$-alkyl, $R_L^3$ is hydrogen, $(C_1$-$C_8)$-alkyl, $(C_2$-$C_4)$-alkenyl, $(C_2$-$C_4)$-alkynyl or aryl, where each of the carbon-containing radicals mentioned above is unsubstituted or substituted by one or more, preferably by up to three, identical or different radicals from the group consisting of halogen and alkoxy; or salts thereof, M) active compounds from the class of the 3-(5-tetrazolylcarbonyl)-2-quinolones, for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999000020, N) compounds of the formula (S-XI) or (S-XII),
as described in WO-A-2007023719 and WO-A-2007023764

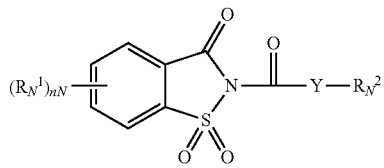

(S-XI)

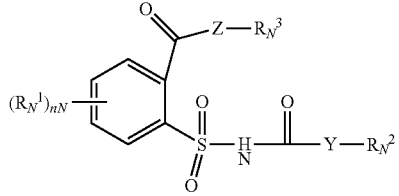

(S-XII)

in which $R_N^1$ is halogen, $(C_1$-$C_4)$-alkyl, methoxy, nitro, cyano, $CF_3$, $OCF_3$ Y, Z independently of one another are O or S, $n_N$ is an integer from 0 to 4, $R_N^2$ is $(C_1$-$C_{16})$-alkyl, $(C_2$-$C_6)$-alkenyl, $(C_3$-$C_6)$-cycloalkyl, aryl, benzyl, halobenzyl, $R_N^3$ is hydrogen, $(C_1$-$C_6)$alkyl, O) one or more compounds from the group consisting of:
1,8-naphthalic anhydride,
O,O-diethyl S-2-ethylthioethyl phosphorodithioate (disulfoton),
4-chlorophenyl methylcarbamate (mephenate),
O,O-diethyl O-phenyl phosphorothioate (dietholate),
4-carboxy-3,4-dihydro-2H-1-benzopyran-4-acetic acid (CL-304415, CAS Reg. No.: 31541-57-8),
2-propenyl 1-oxa-4-azaspiro[4.5]decane-4-carbodithioate (MG-838, CAS Reg. No.: 133993-74-5),
methyl [(3-oxo-1H-2-benzothiopyran-4(3H)-ylidene)methoxy]acetate (from WO-A-98/13361; CAS Reg. No.: 205121-04-6),
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolane (MG-191),
including the stereoisomers, and the salts customary in agriculture.

A mixture N-(tetrazol-4-yl)- or N-(triazol-3-yl)arylcarboxamides as defined above or their salts to be applied in connection with other known active compounds, such as fungicides, insecticides, acaricides, nematicides, bird repellents, plant nutrients and soil structure improvers to transgenic plants containing one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 is likewise possible.

Some of the safeners are already known as herbicides and accordingly, in addition to the herbicidal action against harmful plants, also act by protecting the crop plants. The weight ratios of herbicide (mixture) to safener generally depend on the herbicide application rate and the effectiveness of the safener in question and may vary within wide limits, for example in the range from 200:1 to 1:200, preferably from 100:1 to 1:100, in particular from 20:1 to 1:20. The safeners may be formulated analogously to the compounds of the formula (I) or their mixtures with other herbicides/pesticides and be provided and used as a finished formulation or as a tank mix with the herbicides.

The required application rate of the N-(tetrazol-4-yl)- or N-(triazol-3-yl)arylcarboxamides as defined above to areas where such transgenic plants containing one or more chimeric gene(s) (I) comprising a DNA sequence encoding hydroxyphenylpyruvate dioxygenase (HPPD) derived from a member of a group of organisms, consisting of (a) *Avena*, preferably *Avena sativa*, more preferably comprising a DNA sequence identical to SEQ ID No. 1 encoding HPPD defined by SEQ ID No. 2, (b) *Pseudomonas*, preferably *Pseudomonas fluorescens*, more preferably comprising a DNA sequence identical to SEQ ID No. 3 encoding HPPD defined by SEQ ID No. 4, (c) Synechococcoideae, preferably *Synechococcus* sp., more preferably comprising a DNA sequence identical to SEQ ID No. 6, encoding HPPD defined by SEQ ID No. 7, (d) Blepharismidae, preferably *Blepharisma japonicum*, more preferably comprising a DNA sequence identical to SEQ ID No. 8 encoding HPPD defined by SEQ ID No. 9, (e) *Rhodococcus*, preferably *Rhodococcus* sp. (strain RHA1), isolate ro03041 more preferably comprising a DNA sequence identical to SEQ ID No. 10 encoding HPPD defined by SEQ ID No. 11 or *Rhodococcus* sp. (strain RHA1), isolate ro02040, more preferably comprising a DNA sequence identical to SEQ ID No. 12 encoding HPPD defined by SEQ ID No. 13, (f) Picrophilaceae, preferably *Picrophilus torridus*, more preferably comprising a DNA sequence identical to SEQ ID No. 14 encoding HPPD defined by SEQ ID No. 15, (g) *Kordia*, preferably *Kordia algicida*, more preferably comprising a DNA sequence identical to SEQ ID No. 16 encoding HPPD defined by SEQ ID No. 17 or (II) comprising one or more mutated DNA sequences of HPPD encoding genes of the before defined organisms, preferably mutants as described in WO 2010/085705, U.S. Pat. No. 6,245,968, WO 2009/144079, PCT/EP2010/070561, PCT/EP2010/070567, PCT/EP2010/070578, PCT/EP2010/070570, or PCT/EP2010/070575 varies depending, inter alia, on external conditions such as temperature, humidity and the type of herbicide used. It can vary within wide limits, for example between 0.001 and 10 000 g/ha or more of active substance; however, it is preferably between 0.5 and 5000 g/ha, particularly preferably between 0.5 and 1000 g/ha and very particularly preferably between 0.5 and 500 g/ha.

Sequences Listing

SEQ ID No. 1: Nucleic acid sequence encoding *Avena sativa* HPPD optimized for the expression in *E. coli* cells SEQ ID No. 2: Protein encoded by SEQ ID No. 1

SEQ ID No. 3: Nucleic acid sequence encoding *Pseudomonas fluorescens* HPPD mutated at position 336; mutation Gly=>Trp SEQ ID No. 4: Protein encoded by SEQ ID No. 3

SEQ ID No. 5: Nucleic acid sequence encoding *Pseudomonas fluorescens HPPD mutated at position* 336; mutation Gly=>Trp; optimized for the expression in soybean and cotton SEQ ID No. 6: Nucleic acid sequence encoding *Synechococcus* sp. HPPD SEQ ID No. 7: Protein encoded by SEQ ID No. 6

SEQ ID No. 8: Nucleic acid sequence encoding *Blepharisma japonicum* HPPD

SEQ ID No. 9: Protein encoded by SEQ ID No. 8

SEQ ID No. 10: Nucleic acid sequence encoding *Rhodococcus* sp. (strain RHA1), isolate ro03041 HPPD SEQ ID No. 11: Protein encoded by SEQ ID No. 10

SEQ ID No. 12: Nucleic acid sequence encoding *Rhodococcus* sp. (strain RHA1), isolate ro02040 HPPD SEQ ID No. 13: Protein encoded by SEQ ID No. 12

SEQ ID No. 14: Nucleic acid sequence encoding *Picrophilus torridus* HPPD

SEQ ID No. 15: Protein encoded by SEQ ID No. 14

SEQ ID No. 16: Nucleic acid sequence encoding *Kordia algicida* HPPD

SEQ ID No. 17: Protein encoded by SEQ ID No. 16

SEQ ID No. 18: Nucleic acid sequence encoding *Synechoccus* sp. HPPD optimized for the expression in soybean and cotton SEQ ID No. 19: Nucleic acid sequence encoding *Blepharisma japonicum* HPPD optimized for the expression in soybean and cotton SEQ ID No. 20: Nucleic acid sequence encoding *Rhodococcus* sp. (strain RHA1), isolate ro0341 HPPD optimized for the expression in soybean and cotton SEQ ID No. 21: Nucleic acid sequence encoding *Rhodococcus* sp. (strain RHA1), isolate ro0240 HPPD optimized for the expression in soybean and cotton SEQ ID No. 22: Nucleic acid sequence encoding *Picropphilus torridus* HPPD optimized for the expression in soybean and cotton SEQ ID No. 23: Nucleic acid sequence encoding *Kordia algicida* HPPD optimized for the expression in soybean and cotton I. Cloning of Specific Genes Coding for HPPDs from Various Organisms A. Cloning of *Avena* HPPD (According WO02/46387)

A1—Cloning for Expression in *E. coli* Cells cDNA coding for *Avena sativa* HPPD (AvHPPD; SEQ ID No. 1) was ordered at GeneArt (Regensburg, Germany) using the codon usage optimized for the expression of the gene in *Escherichia coli* cells. Upstream to the start codon ATG, was added the sequence corresponding to the recognition site of the restriction enzyme BamHI, and downstream to the stop codon was added the sequence stretch corresponding to the recognition site of the enzyme HindIII. The synthesized fragment was cloned using the restriction enzymes BamHI and HindIII in the previously opened vector pET32a (Novagen, Darmstadt, Germany), in order to obtain a fusion with the HisTag present in the vector at the N-Terminal extremity from the AvHPPD protein (SEQ ID No. 2). The resulting vector was named pET32a-AvHPPDe.

The protein was produced in *E. coli* and isolated following the standard protocol (as described for example in WO2009/144097).

A2—Cloning of the AvHPPD Gene in the pBin19 Binary Vector for Expression in Tobacco Plants The cDNA corresponding to the gene coding for AvHPPD protein was cut out from the plasmid pET32a-AvHPPDe using the restriction enzymes NcoI and NotI. The overhang sequence resulting from the NotI restriction was filled up, and the consequent fragment was then cloned in the vector pRT100-OTPc (see for example Töpfer (1987), Nucleic Acids Res. 15: 5890, and PCT/EP2010/070561) previously restricted with the enzymes NcoI and SmaI. In this vector, the sequence coding for the AvHPPD was located downstream to the sequence corresponding to an optimized transit peptide responsible for the translocation of the protein to the chloroplast, itself downstream of the sequence corresponding to the CaMV 35S promoter (see for example WO2009/144097). The nucleotide sequence corresponding to the expression cassette CaMV35S-OTPc-AvHPPDe-35S was restricted using the enzyme SbfI and further cloned into the previously opened vector pBin19 with the same enzyme. The resulting plasmid was named pBin19-CaMV35S-OTPc-AvHPPDe-35S, and was used to transform *Agrobacterium tumefaciens* strain ATHV (see for example PCT/EP2010/070561).

B Cloning of PfHPPD-G336W

B1—Cloning of PfHPPD-G336W for the Expression in *E. coli* Cells

The gene coding for the mutant HPPD G336W (SEQ ID No. 3) (U.S. Pat. No. 6,245,968) from *Pseudomonas fluorescens* in the plasmid pKK233-2 (Clontech) (U.S. Pat. No. 6,245,968) was used as template for a PCR to add to the sequence at it 5' extremity the sequence corresponding to the recognition site of the enzyme NcoI and at its 3' extremity the sequence corresponding to the recognition site of the enzyme XbaI. (see WO 2009/144079). The cloning was made in order to obtain a His tag fusion protein at the N-terminal extremity of the *Pseudomonas* HPPD G336W (SEQ ID No. 4) named "pSE420(RI)NX-PfG336W".

B2—Cloning of PfHPPD-G336W for the Expression in Tobacco Plants pFC0117

A binary vector for tobacco or soybean transformation is, for example, constructed with the CaMV35 promoter driving the expression of the gene PfHPPD-G336W (SEQ ID No 5), with a codon usage optimized for the expression in dicotyledoneous plants and at its 5' extremity was added a sequence coding for an OTP, and further upstream a sequence TEV (Tobacco etch virus) to improve the stability of the mRNA in plants followed by the CaMV35S terminator. Additionally, the transformation vector also contains a PAT gene cassette in which the gene is driven by a CaMV35S promoter and followed by a CaMV35S terminator for glufosinate based selection during the transformation process and a 2mEPSPS gene cassette in which the gene is driven by an histone promoter from *Arabidopsis* to confer tolerance to the herbicide glyphosate to the transformed plants. The binary vector was called pFCO117.

C.—Cloning of HPPD Obtained from *Blepharisma* and *Kordia* for Expression in *E. coli* or in Tobacco Plants These clonings were done as described in PCT/EP2010/070567 (*Blepharisma japonicum*, FMP37, Example 1, named "pSE420(RI)NX-FMP37") and PCT/EP2010/070575 (*Kordia algicida*, FMP27, Example 1, named "pSE420(RI)NX-FMP27").

D—Production of HPPD Protein in *E. coli*, Purification Via His-Tag

The *Arabidopsis thaliana* AtHPPD coding sequence (1335 bp; Genebank AF047834; WO 96/38567) was initially cloned into the expression vector pQE-30 (QIAGEN, Hilden, Germany) in between the restriction sites of BamHI and HindIII. The obtained vector was called "pQE30-AtHPPD" (see WO 2009/144079).

The plasmid possesses the trp-lac (trc) promoter and the lacI$^q$ gene that provides the lac repressor in every *E. coli* host strain. The lac repressor binds to the lac operator (lacO) and restricts expression of the target gene; this inhibition can be alleviated by induction with Isopropyl β-D-1-thiogalactopyranoside (IPTG).

All above defined *E. coli* expression vectors were used to transform *Escherichia coli* BL21 cells (Merck, Darmstadt, Germany).

For the AtHPPD (*Arabidopsis thaliana* HPPD) that was used as reference see WO 2009/144079.

Expression of HPPD was carried out in *E. coli* K-12 BL21 containing pQE30-AtHPPD, pET32a-AvHPPDe, pSE420 (RI)NX-PfG336W, pSE420(RI)NX-FMP27 or pSE420(RI) NX-FMP37. Cells were allowed to grow until OD reached 0.5, then expression was initiated from the trp-lac (trc) promoter by induction with 1 mM IPTG which binds to the lac repressor and causes its dissociation from the lac operon. Expression was carried out over 15 h at 28° C.

To prepare the pre-starter culture, 2 mL of TB medium (100 μg*mL$^{-1}$ carbenicillin) were inoculated with 50 μL of an *E. coli* K-12 BL21 glycerol stock. The pre-starter culture was incubated at 37° C. with shaking at 140 rpm for 15 h. 200 μl of the pre-starter culture was used to initiate the starter culture (5 mL TB supplement with 100 μg*L$^{-1}$), which was incubated 3 h at 37° C.

To prepare the main culture, 400 mL of TB medium (100 μg*mL$^{-1}$ carbenicillin) were inoculated with 4 mL of the starter culture. This starter culture was incubated at 37° C. with shaking at 140 rpm until OD$_{600}$ 0.5 was reached. Then recombinant protein expression was induced with 400 μl of 1M IPTG solution. The cells were allowed to grow for an additional hour under these conditions, then the temperature was lowered to 28° C. and the culture was shaken at 140 rpm for 15 h. Cells were harvested by centrifugation at 6000×g for 15 min at 4° C. Then cell pellets were stored at −80° C.

Isolation and Purification of His$_6$-AtHPPD, His$_6$-AvHPPD, His$_6$-PfHPPD-G336W, His$_6$-FMP27 and His$_6$-FMP37 in Native Form Lysis of Cells Cells were lysed using Lysozyme, an enzyme that cleaves the 1,4-β-linkages between N-acetylmuramic acid and N-acetyl-D-glucosamine residues in peptidoglycan which forms the bacterial cell wall. Cell membranes were then disrupted by the internal pressure of the bacterial cell. In addition, the lysis buffer contained Benzonase® Nuclease, an endonuclease that hydrolyzes all forms of DNA and RNA without damaging proteins and thereby largely reduces viscosity of the cell lysate. Lysis under native conditions was carried out on ice.

For purification of His$_6$-tagged proteins the QIAexpress® Ni-NTA Fast Start Kit was used following the user manual instruction.

Purification of His$_6$-tagged Proteins by Immobilized Metal Ion Affinity Chromatography (IMAC)

The cleared cell lysate (10 mL) obtained after centrifugation of the lysis reaction was loaded onto a Ni-NTA Fast Start Column from the QIAexpress® Ni-NTA Fast Start Kit (Qiagen, Hilden, Germany) and purification was carried out according to the instruction manual. The His$_6$-tagged protein was eluted with 2.5 mL of elution buffer.

Desalting of HPPD Solutions by Gel Filtration

HPPD solutions eluted from a Ni-NTA Fast Start Column with 2.5 mL of elution buffer were applied to a Sephadex G-25 PD-10 column (GE Healthcare, Freiburg, Germany) following the user manual instruction. After the whole sample had entered the gel bed, elution was performed with 3.5 mL of storage buffer.

The HPPD solutions eluted from the desalting column were frozen at −80° C. in 1 mL aliquots.

Determination of HPPD Protein Concentration Using the Bradford Protein Assay

Protein concentration was determined using the standard Bradford assay (Bradford, (1976), Anal Biochem 72: 248-254).

Determination of Purity of HPPD Solutions Using SDS-PAGE

The integrity of the eluted protein was checked by SDS-PAGE protein gel electrophoresis using the gel NuPAGE® Novex 4-12% Bis-Tris Gels (Invitrogen, Karlsruhe, Germany), approximately 10 µg of protein were loaded. 10 µL of Laemmli Sample Buffer was added to 1-10 µL of protein solution and the mixture was incubated at 90° C. for 10 min. After short centrifugation step, the whole mixture was loaded into a slot of an SDS gel previously fixed in a XCell Sure-Lock™ Novex Mini-Cell gel chamber filled with NuPAGE® MOPS SDS Running Buffer (diluted from the 20×-solution with ddH$_2$O). A voltage of 150 was then applied to the gel chamber for 1 h. For staining of protein bands, the gel was immersed in Coomassie Brilliant Blue R-250 Staining Solution. For destaining of the polyacrylamide gel, it was immersed in Coomassie Brilliant Blue R-250 Destaining Solution until protein bands appear blue on a white gel.

Evaluation of Tolerance to HPPD Inhibitors of HPPD Enzymes

The HPPD activity was checked by the standard spectrophotmetric assay (method extensively described in WO 2009/144079)

E—Evaluation of Tolerance to HPPD Inhibitor Herbicide

Determination of HPPD Activity in Presence of Several HPPD Inhibitors

Level of tolerance of HPPD proteins obtained from different organisms was determined according to the procedure as described in PCT/EP2010/070575.

On the below Table E1, it can be clearly seen, that the HPPDs obtained from *Kordia algicida* (FMP27), *Blepharisma japonicum* (FMP37), *Avena sativa* (AvHPPD), and from the mutated HPPD-G336W from *Pseudomonas fluorescens* showed superior level of tolerance to all tested HPPD inhibitors than the *Arabidopsis thaliana* HPPD (AtHPPD) at all tested HPPD inhibitor concentrations under identical experimental conditions.

Table E1: Determination of Percentage of Inhibition in Presence of $5.0 \times 10^{-6}$ M of Compound "4-137" Compared to the Activity Measured in Absence of Compound No. "4-137" With HPPD Originated from *Arabidopsis thaliana* (AtHPPD), Mutated *Pseudomonas fluorescens* PfHPPD-G336W, *Avena sativa* (AvHPPD), FMP27 (Derived from *Kordia algicida*) and FMP37 (Derived from *Blepharisma japonicum*).

TABLE E1

| Compound „4-137" | |
|---|---|
| Proteins | Inhibition % |
| AtHPPD | 100 |
| PfHPPD-G336W | 92 |
| AvHPPD | 93 |
| FMP27 | 90 |
| FMP37 | 82 |

These data show that the HPPD derived from *Kordia algicida*, *Blepharisma japonicum*, from *Avena sativa*, and the mutant HPPD-G336W of *Pseudomonas fluorescens* are less sensitive to N-(tetrazol-4-yl)- or N-(triazol-3-yl)arylcarboxamides compared to the inhibition observed with the HPPD derived from *Arabidopsis thaliana*, as shown for Compound "4-137"

F—Evaluation of Tolerance to HPPD Inhibitors of Tobacco Plants Expressing Tolerant HPPD Enzymes Genes coding for the selected HPPD were obtained from a member of the group of organisms consisting of *Avena sativa*, *Pseudomonas fluorescens* mutant G336W, *Blepharisma japonicum* and *Kordia algicida* and cloned into the binary vector pBin19 allowing the integration of DNA into the tobacco genome, under the control of the CaMV35S promoter. For the cloning procedures, see A2 above for *Avena sativa*, see B2 above for *Pseudomonas fluorescens*, mutant G336W, see PCT/EP2010/070567 (published as WO 2011/076882, Example 5; for *Blepharisma japonicum* (FMP37) and see PCT/EP2010/070575, Example 5 for *Kordia algicida* (FMP27). Between the sequence corresponding to the promoter and the sequence coding for the HPPD a DNA sequence coding for a transit peptide to the chloroplast was inserted, in order to add at the N-terminal extremity of the protein a target signal to allow the localization of the HPPD protein into the plant chloroplast.

Seeds harvested from T0 transformants will be put on standard soil for germination. Three weeks later plantlets (T1) will be transferred to single pots and grown under standard cultivation conditions (PCT/EP2010/070575, published as WO 2011/076889). Two weeks later, plants were sprayed with several N-(tetrazol-4-yl)- or N-(triazol-3-yl)arylcarboxamides as defined above. For example, one week after application of compounds "5-148", "4-137", "4-253", "4-278", and "4-25" the symptoms due to the application of the herbicides were evaluated and the transgenic plants showed good tolerance as demonstrated in below Tables F1 to F5, respectively.

Tables F1 to F5: Evaluation of the Symptoms Observed Due to the Application of the Herbicides on Transgenic Tobacco Plants, Expressing the Mutant *Pseudomonas fluorescens* HPPD G336W, the *Avena* HPPD (AvHPPD), the HPPD from *Kordia algicida* FMP27 or the HPPD from *Blepharisma japonicum* (FMP37), Compared to Non-Tranformed Tobacco Plants ("Wt").

The herbicides (with "g AI/ha" meaning "g active ingredient/ha") were applied on 8 to 10 plants originated from 1 to 3 independent transgenic events per transgene.

The symptoms were evaluated and classified as following:

3=Very strong damage
2=Strong damage
1=Light and transient damage
0=No damage

TABLE F1

The compound "5-148"; (WP20 formulation) was mixed with 2 l/ha oilseed rape methyl ester and 1 kg/ha ammonium sulfate, then applied on the transgenic plants using a standard herbicide sprayer at a rate of 25 g AI/ha.

| HPPD | Line | Damage 0 | 1 | 2 | 3 |
|---|---|---|---|---|---|
| Wt | | 0 | 0 | 0 | 10 |
| PfHPPD-G336W | 646 | 0 | 3 | 2 | 4 |
| AvHPPD | 656 | 2 | 1 | 3 | 4 |
| | 659 | 3 | 1 | 0 | 6 |
| | 699 | 1 | 1 | 1 | 7 |
| FMP27 | 733 | 3 | 1 | 4 | 2 |
| | 734 | 4 | 2 | 0 | 4 |
| | 735 | 0 | 4 | 4 | 2 |
| FMP37 | 749 | 2 | 3 | 2 | 3 |
| | 754 | 2 | 1 | 5 | 2 |
| | 795 | 1 | 0 | 6 | 3 |

TABLE F2

The compound "4-137"; 25 g/ha (WP20 formulation) was mixed with 2 l/ha oilseed rape methyl ester and 1 kg/ha ammonium sulfate, then applied on the transgenic plants using a standard herbicide sprayer at a rate of 25 g AI/ha.

| HPPD | Line | Damage 0 | 1 | 2 | 3 |
|---|---|---|---|---|---|
| Wt | | 0 | 0 | 0 | 10 |
| PfHPPD-G336W | 646 | 5 | 2 | 0 | 3 |
| AvHPPD | 656 | 3 | 1 | 1 | 5 |
| | 659 | 3 | 3 | 0 | 4 |
| | 699 | 1 | 2 | 0 | 7 |
| FMP27 | 733 | 4 | 0 | 1 | 5 |
| | 734 | 5 | 2 | 0 | 3 |
| | 735 | 3 | 0 | 4 | 3 |
| FMP37 | 749 | 8 | 2 | 0 | 0 |
| | 754 | 0 | 1 | 1 | 8 |
| | 795 | 2 | 0 | 2 | 6 |

TABLE F3

The compound "4-253"; 50 g/ha (WP20 formulation) was mixed with 2 l/ha oilseed rape methyl ester and 1 kg/ha ammonium sulfate, then applied on the transgenic plants using a standard herbicide sprayer at a rates of 50 g AI/ha.

| HPPD | Line | Damage 0 | 1 | 2 | 3 |
|---|---|---|---|---|---|
| Wt | | 0 | 0 | 0 | 10 |
| PfHPPD-G336W | 646 | 9 | 0 | 0 | 1 |
| AvHPPD | 659 | 3 | 0 | 0 | 7 |
| FMP27 | 733 | 4 | 4 | 2 | 0 |
| | 734 | 6 | 1 | 2 | 1 |
| | 735 | 2 | 5 | 0 | 3 |
| FMP37 | 749 | 7 | 2 | 0 | 1 |
| | 754 | 6 | 2 | 1 | 1 |
| | 795 | 3 | 4 | 0 | 3 |

TABLE F4

The compound "4-278"; 50 g/ha (WP20 formulation) was mixed with 2 l/ha oilseed rape methyl ester and 1 kg/ha ammnium sulfate, then applied on the transgenic plants using a standard herbicides sprayer at a rate of 50 g AI/ha.

| HPPD | Line | Damage 0 | 1 | 2 | 3 |
|---|---|---|---|---|---|
| Wt | | 0 | 0 | 0 | 10 |
| PfHPPD-G336W | 646 | 6 | 3 | 0 | 1 |
| AvHPPD | 659 | 9 | 0 | 0 | 1 |
| FMP27 | 733 | 6 | 4 | 0 | 0 |
| | 734 | 6 | 3 | 0 | 1 |
| | 735 | 6 | 2 | 0 | 2 |
| FMP37 | 749 | 5 | 4 | 0 | 1 |
| | 754 | 5 | 4 | 0 | 1 |
| | 795 | 4 | 3 | 0 | 3 |

TABLE F5

The compound "4-25"; 50 g/ha (WP20 formulation) was mixed with 2 l/ha oilseed rape methyl ester and 1 kg/ha ammnium sulfate, then applied on the transgenic plants using a standard herbicides sprayer at a rate of 50 g AI/ha.

| HPPD | Line | Damage 0 | 1 | 2 | 3 |
|---|---|---|---|---|---|
| Wt | | 0 | 0 | 0 | 10 |
| PfHPPD-G336W | 646 | 10 | 0 | 0 | 0 |
| AvHPPD | 659 | 6 | 1 | 0 | 3 |
| FMP27 | 733 | 9 | 1 | 0 | 0 |
| | 734 | 6 | 3 | 0 | 1 |
| | 735 | 5 | 3 | 0 | 0 |
| FMP37 | 749 | 8 | 0 | 0 | 2 |
| | 754 | 3 | 5 | 1 | 1 |
| | 795 | 7 | 0 | 1 | 2 |

These data show that tobacco plants of all the tested independent lines expressing the HPPD derived from *Kordia algicida*, *Blepharisma japonicum*, from *Avena sativa* and the mutant "G336W" of *Pseudomonas fluorescens* HPPD are less sensitive at agronomically relevant dose to N-(tetrazol-4-yl)- or N-(triazol-3-yl)arylcarboxamides than wild type (wt) plants as shown for Compounds "5-148", "4-137", "4-253", "4-278", and "4-25".

G—Evaluation of Tolerance to HPPD Inhibitors of Soybean Plants Expressing Tolerant HPPD Enzymes, *Pseudomonas fluorescens* "G336W" Mutant, FMP 27, and FMP 37

Genes coding for the selected HPPD were obtained from a member of the group of organisms consisting of *Blepharisma japonicum* and *Kordia algicida* and cloned into an appropriate binary vector allowing the integration of DNA into the soybean genome, under the control of the CaMV35S promoter. For the respective cloning procedures, see WO2011076882 (PCT/EP2010/070567), Example 9; for *Blepharisma japonicum* (FMP37) and WO2011076889 (PCT/EP2010/070575), Example 9 for *Kordia algicida* (FMP27).

Between the sequence corresponding to the promoter and the sequence coding for the HPPD a DNA sequence coding for a transit peptide to the chloroplast was inserted, in order to add at the N-terminal extremity of the protein a target signal to allow the localization of the HPPD protein into the plant chloroplast. By using the vectors "pFCO112" (*Blepharisma japonicum*, WO2011076882), pFCO116 (Korida algicida, WO2011076889), and pFCO117" (see Example B2, above), soybean transformation was achieved as described in Example 10 of WO2011076882 (PCT/EP2010/070567) for *Blepharisma japonicum* (FMP37) and WO2011076889 (PCT/EP2010/070575) for *Kordia algicida* (FMP27). Seeds from T0 events showing tolerance to tembotrione were harvested.

T1 Soybean seeds were transferred to single pots and grown under standard cultivation conditions, see WO2011076882.

Two weeks later, plants will be sprayed with several N-(tetrazol-4-yl)- or N-(triazol-3-yl)arylcarboxamides as defined above. For example, one week after application of compounds "5-148", "4-137", "4-253", "4-278", and "4-25" the symptoms due to the application of the herbicides will be evaluated and the transgenic plants will show superior tolerance compared to the wild-type soybean plants.

H—Evaluation of Tolerance to HPPD Inhibitors of Cotton Plants Expressing Tolerant HPPD Enzymes FMP 27 and FMP 37

Genes coding for the selected HPPD were obtained from a member of the group of organisms consisting of *Blepharisma japonicum* and *Kordia algicida* and cloned into an appropriate binary vector allowing the integration of DNA into the cotton genome, under the control of the CaMV35S promoter. For the respective cloning procedures, see WO2011076882 (PCT/EP2010/070567), Example 11; for *Blepharisma japonicum* (FMP37) and WO2011076889 (PCT/EP2010/070575), Example 11 for *Kordia algicida* (FMP27).

Between the sequence corresponding to the promoter and the sequence coding for the HPPD a DNA sequence coding for a transit peptide to the chloroplast was inserted, in order to add at the N-terminal extremity of the protein a target signal to allow the localization of the HPPD protein into the plant chloroplast. Cotton transformation was achieved as described in Example 12 of WO2011076882 (PCT/EP2010/070567) for *Blepharisma japonicum* (FMP37) and WO2011076889 (PCT/EP2010/070575) for *Kordia algicida* (FMP27). Seeds from T0 events showing tolerance to tembotrione were harvested.

T1 Cotton seeds were transferred to single pots and grown under standard cultivation conditions, see WO2011076882 (PCT/EP2010/070567) for *Blepharisma japonicum* (FMP37) and WO2011076889 (PCT/EP2010/070575) for *Kordia algicida* (FMP27).

At least 4 weeks later, plants will be sprayed with several N-(tetrazol-4-yl)- or N-(triazol-3-yl)arylcarboxamides as defined above. For example, one week after application of compounds "5-148", "4-137", "4-253", "4-278", and "4-25" the symptoms due to the application of the herbicides will be evaluated and the transgenic plants will show superior tolerance compared to the wild-type cotton plants.

The invention claimed is:

1. An N-(tetrazol-4-yl)arylcarboxamide of formula (I) and/or a salt thereof

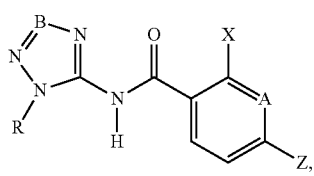

(I)

capable of being used for controlling an unwanted plant in an area of a transgenic crop plant being tolerant to a HPPD inhibitor herbicide by containing at least one chimeric gene comprising:
(I) a DNA sequence encoding hydroxyphenylpyruvate dioxygenase (HPPD) derived from a member of a group of organisms selected from (a) *Avena*, (b) *Pseudomonas*, (c) *Synechococcoideae*, (d) *Blepharismidae*, (e) *Rhodococcus*, (f) Picrophilaceae, and (g) Kordia, or
(II) at least one mutated DNA sequence of HPPD encoding genes of the before defined group of organisms
in which
A is N or CY,
B is N,
X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_3-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OCOR^1$, $OSO_2R^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR^1NR^2$, $P(O)(OR^5)_2$, $CH_2P(O)(OR^5)_2$, $(C_1-C_6)$-alkyl-heteroaryl, or $(C_1-C_6)$-alkyl-heterocyclyl, the two last-mentioned radicals being substituted in each case by s halogen, $(C_1-C_6)$-alkyl, halo-$(C_1-C_6)$-alkyl, $S(O)_n$—$(C_1-C_6)$-alkyl, $(C_1-C_6)$-alkoxy and/or halo-$(C_1-C_6)$-alkoxy radicals, and where heterocyclyl carries from 0 to 2 oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_3-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, the last 6 radicals being substituted in each case by s radical selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_6)$-alkyl and cyanomethyl, and where heterocyclyl carries from 0 to 2 oxo groups, Z is cyano, thiocyanato, halo-$(C_1-C_6)$-alkyl, $(C_2-C_6)$-alkenyl, halo-$(C_2-C_6)$-alkenyl, $(C_3-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, heteroaryl, heterocyclyl or phenyl, the last three radicals being substituted in each case by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy or halo-$(C_1-C_6)$-alkoxy, and where heterocyclyl carries from 0 to 2 oxo groups, or Z is optionally hydrogen, $(C_1-C_6)$-alkyl or $(C_1-C_6)$-alkoxy if Y is the radical $S(O)_nR^2$, R is $(C_1-C_6)$-alkyl, $(C_3-C_7)$-cycloalkyl, halo-$(C_1-C_6)$-alkyl, $(C_2-C_6)$-alkenyl, halo-$(C_2-C_6)$-alkenyl, $(C_3-C_6)$-alkynyl, halo-$(C_3-C_6)$-alkynyl, $CH_2R^6$, heteroaryl, heterocyclyl or phenyl, the last three radicals being substituted in each case by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_3-C_6)$-alkynyl, $(C_3-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, or $(C_1-C_6)$-alkyl-$NR^3$-heterocyclyl, the 21 last-mentioned radicals being substituted in each case by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries from 0 to 2 oxo groups, $R^2$ is $(C_1-C_6)$-alkyl, $C_1-C_6$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, or $(C_1-C_6)$-alkyl-$NR^3$-heterocyclyl, the 21 last-mentioned radicals being substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries from 0 to 2 oxo groups, $R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ is $(C_1-C_6)$-alkyl, $(C_2-C_6)$-alkenyl or $(C_2-C_6)$-alkynyl, $R^5$ is methyl or ethyl, $R^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy or $(C_3-C_6)$-cycloalkyl or is heteroaryl, or phenyl substituted in each case by s radicals selected from the group consisting of methyl, ethyl, methoxy, trifluoromethyl, and halogen, n is 0, 1 or 2, and s is 0, 1, 2 or 3.

2. A N-(tetrazol-4-yl)arylcarboxamide of formula (I) and/or a salt thereof according to claim 1, where, in formula (I)

A is N or CY,

B is N,

X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_3-C_6)$-alkynyl, halo-$(C_3-C_6)$-alkynyl, $(C_3-C_6)$-cycloalkyl, halo-$(C_3-C_6)$-cycloalkyl, $(C_1-C_6)$-alkyl-O—$(C_1-C_6)$-alkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OCOR^1$, $OSO_2R^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-heteroaryl, or $(C_1-C_6)$-alkyl-heterocyclyl, the two last-mentioned radicals being substituted in each case by s halogen, $(C_1-C_6)$-alkyl, halo-$(C_1-C_6)$-alkyl, $S(O)_n$—$(C_1-C_6)$-alkyl, $(C_1-C_6)$-alkoxy and/or halo-$(C_1-C_6)$-alkoxy radicals, and where heterocyclyl carries from 0 to 2 oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_3-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $COOR^1$, $OSO_2R^2$, $S(O)_nR^2$, $SO_2OR^1$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, the last 6 radicals being substituted in each case by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries from 0 to 2 oxo groups, Z is cyano, thiocyanato, halo-$(C_1-C_6)$-alkyl, $(C_2-C_6)$-alkenyl, halo-$(C_2-C_6)$-alkenyl, $(C_3-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $C(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$ or 1,2,4-triazol-1-yl, or Z is optionally hydrogen, $(C_1-C_6)$-alkyl or $(C_1-C_6)$-alkoxy if Y is the radical $S(O)_nR^2$, R is $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, or phenyl or benzyl each substituted by s radicals selected from the group consisting of methyl, methoxy, trifluoromethyl and halogen, $R^1$ is hydrogen, $(C_1-C_6)$-alkyl, $(C_2-C_6)$-alkenyl, $((C_3-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-NR$^3$-heteroaryl, or $(C_1-C_6)$-alkyl-NR$^3$-heterocyclyl, the 16 last-mentioned radicals being substituted in each case by s radicals selected from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries from 0 to 2 oxo groups, $R^2$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-NR$^3$-heteroaryl or $(C_1-C_6)$-alkyl-NR$^3$-heterocyclyl, these radicals being substituted by s radicals selected from the group consisting of cyano, halogen, nitro, $OR^3$, $S(O)_nR^4$, $N(R^3)_2$, $NR^3OR^3$, $NR^3SO_2R^4$, $COR^3$, $OCOR^3$, $NR^3COR^3$, $CO_2R^3$, $CON(R^3)_2$ and $(C_1-C_4)$-alkoxy-$(C_2-C_6)$-alkoxycarbonyl, and where heterocyclyl carries from 0 to 2 oxo groups, $R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ is $(C_1-C_6)$-alkyl, $(C_2-C_6)$-alkenyl or $(C_2-C_6)$-alkynyl, n is 0, 1 or 2, and s is 0, 1, 2 or 3.

3. A N-(tetrazol-4-yl)arylcarboxamide of formula (I) and/or a salt thereof according to claim 1, where, in formula (I)

A is N or CY,

B is N,

X is nitro, halogen, cyano, $(C_1-C_6)$-alkyl, halo-$(C_1-C_6)$-alkyl, $(C_3-C_6)$-cycloalkyl, $(C_1-C_6)$-alkyl-$S(O)_nR^2$, $(C_1-C_6)$-alkyl-$OSO_2R^2$, $(C_1-C_6)$-alkyl-$OR^1$, $(C_1-C_6)$-alkyl-$SO_2N(R^1)_2$, $(C_1-C_6)$-alkyl-$NR^1COR^1$, $(C_1-C_6)$-alkyl-heteroaryl, $(C_1-C_6)$-alkyl-heterocyclyl, the two last-mentioned radicals being substituted in each case by s halogen, $(C_1-C_6)$-alkyl, halo-$(C_1-C_6)$-alkyl, $S(O)_n$—$(C_1-C_6)$-alkyl, $(C_1-C_6)$-alkoxy and/or halo-$(C_1-C_6)$-alkoxy radicals, and where heterocyclyl carries from 0 to 2 oxo groups, Y is hydrogen, nitro, halogen, cyano, $(C_1-C_6)$-alkyl, halo-$(C_1-C_6)$-alkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, the last 6 radicals being substituted in each case by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_6)$-alkyl and cyanomethyl, and where heterocyclyl carries from 0 to 2 oxo groups, Z is cyano, halo-$(C_1-C_6)$-alkyl, $(C_3-C_6)$-cycloalkyl, $S(O)_nR^2$ or 1,2,4-triazol-1-yl, or Z is optionally hydrogen, methyl, methoxy or ethoxy if Y is the radical $S(O)_nR^2$, R is $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl or methoxymethyl, or is phenyl substituted by s radicals selected from the group consisting of methyl, methoxy, trifluoromethyl, and halogen, $R^1$ is hydrogen, $(C_1-C_6)$-alkyl, $(C_1-C_6)$-alkenyl, $((C_3-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-NR$^3$-heteroaryl, or $(C_1-C_6)$-alkyl-NR$^3$-heterocyclyl, the 16 last-mentioned radicals being substituted in each case by s radicals selected from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries from 0 to 2 oxo groups, $R^2$ is $(C_1-C_6)$-alkyl, $(C_3-C_6)$-cycloalkyl or $(C_3-C_6)$-cycloalkyl-$(C_1-C_6)$-alkyl, these three aforementioned radicals being substituted in each case by s radicals selected from the group consisting of halogen and $OR^3$, $R^3$ is hydrogen or $(C_1-C_6)$-alkyl, $R^4$ is $(C_1-C_6)$-alkyl, n is 0, 1 or 2, and s is 0, 1, 2 or 3.

4. A method for controlling an unwanted plant comprising applying at least one N-(tetrazol-4-yl)arylcarboxamide according to claim 1 in an area of a transgenic crop plant being tolerant to a HPPD inhibitor herbicide by containing at least one chimeric gene comprising (I) a DNA sequence encoding hydroxyphenylpyruvate dioxygenase (HPPD) derived from a member of a group of organisms selected from (a) *Avena*, (b) *Pseudomonas*, (c) *Synechococcoideae*, (d) *Blepharismidae*, (e) *Rhodococcus*, (f) Picrophilaceae, and (g) Kordia, or (II) at least one mutated DNA sequence of a HPPD encoding gene of the before defined group of organisms, in which said applying is performed to (a) an unwanted plant, (b) to a seed of an unwanted plant, and/or (c) to an area on which a plant grows.

5. A method according to claim 4, in which the transgenic crop plant belongs to at least one of a group of dicotyledonous crops selected from *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum*, and *Vicia*, and/or to a group of monocotyledonous crops selected from the group *Allium, Ananas, Asparagus, Avena, Hordeum, Oryza, Panicum, Saccharum, Secale, Sorghum, Triticale, Triticum*, and *Zea*.

6. A method according to claim 4, in which at least one N-(tetrazol-4-yl)arylcarboxamide according to claim 1 is applied in combination with at least one HPPD inhibitor herbicide comprising triketone and/or pyrazolinate herbicide in mixed formulation and/or in a tank mix, and/or with any further known active substance which is based on inhibition of acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, and/or acts as a growth regulator.

7. A method according to claim 6, in which at least one N-(tetrazol-4-yl)arylcarboxamide according to claim 1 is applied in combination with at least one HPPD inhibitor herbicide selected from the group consisting of tembotrione, mesotrione, bicyclopyrone, tefuryltrione, pyrasulfotole, pyrazolate, diketonitrile, benzofenap, and sulcotrione.

8. A method according to claim 5, in which at least one N-(tetrazol-4-yl)arylcarboxamide according to claim 1 is applied in combination with at least one HPPD inhibitor herbicide comprising triketone and/or pyrazolinate herbicide in mixed formulation and/or in tank mix, and/or with any further known active substance which is based on inhibition of acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, and/or acts as a growth regulator.

9. An N-(tetrazol-4-yl)arylcarboxamide of formula (I) and/or a salt thereof according to claim 1, where in formula (I)

A is CY,
B is N,
X is halogen or $(C_1-C_6)$-alkyl,
Y is hydrogen, $OR^1$, $(C_1-C_6)$-alkyl-$OR^1$, or $SO_2CH_3$,
Z is halo-$(C_1-C_6)$-alkyl or $SO_2CH_3$,
R is $(C_1-C_6)$-alkyl, and
$R^1$ is $(C_1-C_6)$-alkyl.

10. An N-(tetrazol-4-yl)arylcarboxamide of formula (I) and/or a salt thereof according to claim 1, where in formula (I)

A is CY,
B is N,
X is chlorine or methyl,
Y is hydrogen, ethoxy, methoxymethyl, or $SO_2CH_3$,
Z is trifluoromethyl or $SO_2CH_3$, and
R is methyl or ethyl.

11. An N-(tetrazol-4-yl)arylcarboxamide of formula (I) and/or a salt thereof according to claim 1, where in formula (I)

A is CY,
B is N,
X is methyl,
Y is $SO_2CH_3$,
Z is trifluoromethyl, and
R is methyl.

* * * * *

SEQUENCE LISTING

```
<160> NUMBER OF SEQ ID NOS: 23

<210> SEQ ID NO 1
<211> LENGTH: 1323
<212> TYPE: DNA
<213> ORGANISM: Artificial Sequence
<220> FEATURE:
<223> OTHER INFORMATION: Nucleic acid sequence encoding Avena sativa
      HPPD optimized for the expression in Escherichia coli cells

<400> SEQUENCE: 1
atgcctccga caccggcaac agcaaccggt gcagcagcag cagccgttac accggaacat      60
gcagcacgta gctttccgcg tgttgttcgt gttaatccgc gtagcgatcg ttttccggtt     120
ctgagctttc atcatgttga actgtggtgt gcagatgcag caagcgcagc aggtcgtttt     180
agctttgcac tgggtgcacc tctggcagca cgttctgatc tgagcaccgg taatagcgca     240
catgcaagcc tgctgctgcg tagcggtgca ctggcatttc tgtttaccgc tccgtatgca     300
cctcctccgc aggaagcagc aaccgcagcc gcaaccgcaa gcattccgag ctttagcgca     360
gatgcagccc gtacctttgc agcagcacat ggcctggcag ttcgtagcgt tggtgttcgt     420
gttgcagatg ccgcagaagc atttcgcgtt agcgttgcgg gaggtgcacg tcctgcattt     480
gcaccggcag atctgggtca tggttttggt ctggcagaag ttgaactgta cggcgatgtt     540
gttctgcgtt ttgttagcta tccggatgaa accgatctgc cgtttctgcc tggttttgaa     600
cgtgttagct ctccgggtgc agttgattat ggtctgaccc gttttgatca tgttgttggc     660
```

```
aatgttccgg aaatggcacc ggttattgat tatatgaaag gctttctggg ctttcatgaa    720
tttgcagaat ttaccgcaga agatgttggc accaccgaaa gcggtctgaa tagcgttgtt    780
ctggccaata atagcgaagc agttctgctg ccgctgaatg aaccggtgca tggcaccaaa    840
cgtcgtagcc agattcagac ctatctggaa tatcatggtg gtccgggtgt tcagcatatt    900
gcactggcaa gcaatgatgt tctgcgtacc ctgcgtgaaa tgcgtgcacg taccccgatg    960
ggtggttttg aatttatggc acctccgcag gcaaaatatt atgaaggtgt gcgtcgtatt   1020
gccggtgatg ttctgagcga agagcagatt aaagaatgcc aggaactggg cgttctggtt   1080
gatcgtgatg atcagggtgt tctgctgcag attttttacca aaccggttgg tgatcgtccg   1140 acctttttc tggaaatgat tcagcgtatt ggctgcatgg aaaaagatga agtgggtcag   1200
gaatatcaga aaggcggttg tggtggtttt ggtaaaggca ttttagcga actgtttaaa   1260 agcattgaag attatgaaaa aagcctggaa gttaaacaga gcgttgttgc ccagaaaagc   1320
taa                                                                1323
```

```
<210> SEQ ID NO 2
<211> LENGTH: 440
<212> TYPE: PRT
<213> ORGANISM: Avena sativa

<400> SEQUENCE: 2

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
    130                 135                 140

Ala Glu Ala Phe Arg Val Ser Val Ala Gly Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255
```

```
Asn Ser Val Val Leu Ala Asn Ser Glu Ala Val Leu Leu Pro Leu
            260                 265                 270

Asn Glu Pro Val His Gly Thr Lys Arg Arg Ser Gln Ile Gln Thr Tyr
        275                 280                 285

Leu Glu Tyr His Gly Gly Pro Gly Val Gln His Ile Ala Leu Ala Ser
    290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Glu Gln Ile Lys Glu
            340                 345                 350

Cys Gln Glu Leu Gly Val Leu Val Asp Arg Asp Asp Gln Gly Val Leu
        355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Val Lys
            420                 425                 430

Gln Ser Val Val Ala Gln Lys Ser
        435                 440

<210> SEQ ID NO 3
<211> LENGTH: 1077
<212> TYPE: DNA
<213> ORGANISM: Pseudomonas fluorescens
<220> FEATURE:
<221> NAME/KEY: misc_feature
<222> LOCATION: (1006)..(1008)
<223> OTHER INFORMATION: GGT codon is replaced by codon TGG

<400> SEQUENCE: 3
atggcagatc tatacgaaaa cccaatgggc ctgatgggct ttgaattcat cgaattcgcg      60
tcgccgacgc cgggtaccct ggagccgatc ttcgagatca tgggcttcac caaagtcgcg     120
acccaccgtt ccaagaacgt gcacctgtac cgccagggcg agatcaacct gatcctcaac     180
aacgagccca acagcatcgc ctcctacttt gcggccgaac acggcccgtc ggtgtgcggc     240
atggcgttcc gcgtgaagga ctcgcaaaag gcctacaacc gcgccctgga actcggcgcc     300
cagccgatcc atattgacac cgggccgatg gaattgaacc tgccggcgat caagggcatc     360
ggcggcgcgc cgttgtacct gatcgaccgt ttcggcgaag cagctcgat ctacgacatc     420 gacttcgtgt acctcgaagg tgtggagcgc aatccggtcg gtgcaggtct caaagtcatc     480
gaccacctga cccacaacgt ctatcgcggc cgcatggtct actgggccaa cttctacgag     540
aaattgttca acttccgtga agcgcgttac ttcgatatca agggcgagta caccggcctg     600
acttccaagg ccatgagtgc gccggacgga atgatccgca tcccgctgaa cgaagagtcg     660
tccaagggcg cggggcagat cgaagagttc ctgatgcagt tcaacggcga aggcatccag     720
cacgtggcgt tcctcaccga cgacctggtc aagacctggg acgcgttgaa gaaaatcggc     780
atgcgcttca tgaccgcgcc gccagacact tattacgaaa tgctcgaagg ccgcctgcct     840
gaccacggcg agccggtgga tcaactgcag gcacgcggta tcctgctgga cggatcttcc     900
```

-continued

```
gtggaaggcg acaaacgcct gctgctgcag atcttctcgg aaaccctgat gggcccggtg    960
ttcttcgaat tcatccagcg caagggcgac gatgggtttg cgagtggaa cttcaaggcg   1020 ctgttcgagt ccatcgaacg tgaccaggtg cgtcgtggtg tattgaccgc cgattaa     1077
```

<210> SEQ ID NO 4
<211> LENGTH: 358
<212> TYPE: PRT
<213> ORGANISM: Pseudomonas fluorescens
<220> FEATURE:
<221> NAME/KEY: MISC_FEATURE
<222> LOCATION: (336)..(336)
<223> OTHER INFORMATION: Gly replaced by Trp

<400> SEQUENCE: 4

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
```

```
              325                 330                 335
Asn Phe Lys Ala Leu Phe Glu Ser Ile Glu Arg Asp Gln Val Arg Arg
            340                 345                 350
Gly Val Leu Thr Ala Asp
        355
```

<210> SEQ ID NO 5
<211> LENGTH: 1077
<212> TYPE: DNA
<213> ORGANISM: Artificial Sequence
<220> FEATURE:
<223> OTHER INFORMATION: Nucleic acid sequence encoding Pseudomonas
      fluorescens HPPD mutated at the position 336 (Gly to Trp )
      optimized for the expression in soybean and cotton
<220> FEATURE:
<221> NAME/KEY: misc_feature
<222> LOCATION: (1006)..(1008)
<223> OTHER INFORMATION: GGT codon is replaced by codon TGG

<400> SEQUENCE: 5

```
atggctgatc tttatgagaa ccctatgggt cttatgggct cgagtttat tgagttcgct      60 tctcctaccc ctggtactct tgaaccatat ttcgagatca tgggcttcac taaggttgca    120
actcacaggt ctaagaacgt tcacctttac aggcagggtg agatcaacct tatccttaac    180
aacgagccta actccattgc ttcttatttc gctgctgagc atggtccatc tgtttgcggt    240
atggctttca gagttaagga ttctcagaag cttacaacaa gggctcttga acttggtgct    300
cagcctattc atattgatac cggacctatg aactcaacc ttcctgctat taagggtatt    360
ggtggtgctc tctttacct tattgataga ttcggtgagg gctcctccat ctacgatatt    420
gatttcgttt accttgaggg cgttgagaga aaccctgttg gtgctggtct taaggttatc    480
gatcacctta cccacaacgt ttacagaggt aggatggttt actgggctaa cttctacgag    540
aagttgttca acttcagaga ggctcgttac ttcgatatta agggcgagta cactggtctt    600
acctctaagg ctatgtctgc tcctgatggt atgatcagga ttcctcttaa cgaagagtcc    660
tctaagggtg ctggtcaaat tgaagagttc ctcatgcaat tcaacggtga gggtattcag    720
catgttgctt tcttgaccga tgaccttgtt aagacttggg acgctcttaa gaaaatcggc    780
atgcgtttca tgactgctcc tccagatact tactacgaaa tgcttgaggg taggcttcct    840
gatcatggtg aacctgttga tcaacttcag gctaggggta ttcttcttga tggttcttct    900
gttgagggcg ataagaggct tttgcttcag attttctccg agactcttat gggtcctgtg    960
ttcttcgagt tcattcagag aaagggtgat gatggtttcg tgaatggaa cttcaaggct    1020 cttttcgagt ccattgagag ggatcaagtt agaagggtg ttcttaccgc tgattaa      1077
```

<210> SEQ ID NO 6
<211> LENGTH: 1053
<212> TYPE: DNA
<213> ORGANISM: Synechococcus sp.

<400> SEQUENCE: 6

```
atgaacccgt ccattcgaat tgtccaaggg atccaccacc tgcacttcta cctttgggat      60
ctgccccgtt ggcgggaaca cttttgtcgg gtttgggct ccgggtggc aagcgacgcc    120 ggcaacaccc tggagctgga gcagggatcc ctgcgcttgc gcctgtctca gccggcacgg    180 gcggggacg aggtggaccg ccatttgcag cggcatgggc ggggggtggt ggatgtggcc    240
ttggcggtgg agagcagga gctaccggcc ttggcggagc tgttgcgggg ccgaggcgcc    300
caactggcgt ggatcccggc agcagcggcg ctctgcctcc acccccta cgggatccgg    360
```

```
cattctctga tccctggccc cttggatgcc gccccctgccg aagcgggcct gttttcccac    420
tgggatcacg tggtgttgaa cgtggagcag ggatccctgc aggcggcagc cgactggtat    480
gggcgggtgc tgggctggcg gcggctgtac cgctacagca tcggcaccgc cacctccggc    540
ctggaaagcg tggtggtggg ggatccggaa gcggggatcc aatgggccat caacgagccc    600
acctgtgccg cttcccagat tcaggagttt ttgcatgccc atggcggccc gggcattcag    660
cacgcggcgc tgcacagctc agacattgtt gccagcctgc gccggttgcg caggggggga    720
gtggactttt tgcaagtggc cgcgcagtac tacaccagcc tggaaaggga gctggggttg    780
gcgctccgtt ctgcccttgg gcaggccatc tcctggcaag acctggtgga gcagcagatc    840
cttctggatg ctaccctgcc cgcttctgat ggccaggatc gccccttct gctgcagacc    900 tttacccagc ccctctttgg tcggcccacc ttttctttg aagtcattca acggctaggc    960
ggggccacgg gctttggcga ggccaatttt caggctttgt tcgaggccct ggaacggcaa   1020
cagcgacagc gacaccaggc gctgacccct tag                                1053

<210> SEQ ID NO 7
<211> LENGTH: 350
<212> TYPE: PRT
<213> ORGANISM: Synechococcus sp.

<400> SEQUENCE: 7

Met Asn Pro Ser Ile Arg Ile Val Gln Gly Ile His His Leu His Phe
  1               5                  10                  15

Tyr Leu Trp Asp Leu Pro Arg Trp Arg Glu His Phe Cys Arg Val Trp
             20                  25                  30

Gly Phe Arg Val Ala Ser Asp Ala Gly Asn Thr Leu Glu Leu Glu Gln
         35                  40                  45

Gly Ser Leu Arg Leu Arg Leu Ser Gln Pro Ala Arg Ala Gly Asp Glu
     50                  55                  60

Val Asp Arg His Leu Gln Arg His Gly Pro Gly Val Val Asp Val Ala
 65                  70                  75                  80

Leu Ala Val Gly Glu Gln Glu Leu Pro Ala Leu Ala Glu Leu Leu Arg
                 85                  90                  95

Gly Arg Gly Ala Gln Leu Ala Trp Ile Pro Ala Ala Ala Leu Cys
            100                 105                 110

Leu His Thr Pro Tyr Gly Ile Arg His Ser Leu Ile Pro Gly Pro Leu
        115                 120                 125

Asp Ala Ala Pro Ala Glu Ala Gly Leu Phe Ser His Trp Asp His Val
    130                 135                 140

Val Leu Asn Val Glu Gln Gly Ser Leu Gln Ala Ala Asp Trp Tyr
145                 150                 155                 160

Gly Arg Val Leu Gly Trp Arg Arg Leu Tyr Arg Tyr Ser Ile Gly Thr
                165                 170                 175

Ala Thr Ser Gly Leu Glu Ser Val Val Gly Asp Pro Glu Ala Gly
            180                 185                 190

Ile Gln Trp Ala Ile Asn Glu Pro Thr Cys Ala Ala Ser Gln Ile Gln
        195                 200                 205

Glu Phe Leu His Ala His Gly Gly Pro Gly Ile Gln His Ala Ala Leu
    210                 215                 220

His Ser Ser Asp Ile Val Ala Ser Leu Arg Arg Leu Arg Gln Gly Gly
225                 230                 235                 240

Val Asp Phe Leu Gln Val Ala Pro Gln Tyr Tyr Thr Ser Leu Glu Arg
```

```
                    245                 250                 255
Glu Leu Gly Leu Ala Leu Arg Ser Ala Leu Gly Gln Ala Ile Ser Trp
            260                 265                 270

Gln Asp Leu Val Glu Gln Gln Ile Leu Leu Asp Ala Thr Leu Pro Ala
        275                 280                 285

Ser Asp Gly Gln Asp Arg Pro Leu Leu Leu Gln Thr Phe Thr Gln Pro
    290                 295                 300

Leu Phe Gly Arg Pro Thr Phe Phe Glu Val Ile Gln Arg Leu Gly
305                 310                 315                 320

Gly Ala Thr Gly Phe Gly Glu Ala Asn Phe Gln Ala Leu Phe Glu Ala
                325                 330                 335

Leu Glu Arg Gln Gln Arg Gln Arg His Gln Ala Leu Thr Pro
            340                 345                 350

<210> SEQ ID NO 8
<211> LENGTH: 1149
<212> TYPE: DNA
<213> ORGANISM: Blepharisma japonicum

<400> SEQUENCE: 8
atgacttatt acgacaagca agaaacgcgt ccagatcttg gcgaattcta tggtttccat        60
cacgttcgtt tttacgtctc caactcagag caagccgctt cgttctacac atctcgcttt      120
gggttttctc cggttgccta tgaaggattg aaacaggaa accaaaaatt ctgtaccaat       180
gtcgtccgaa gcaaccatgt agtcatcgct tttacctcag ctctcactcc tgaagacaat      240
gaagtgaacc gtcacgttgg caagcatagt gatggagttc aagacattgc ctttagtgta      300
agtgacgcaa gagggatgta tgagaaagcg atagctaaag gctgtaaaag cttccgtgag      360
ccacaggttt tacaagatca atttggatct gttataatag cgtctctcca gacttatgga      420
gacactgttc acacattagt ccaaaatgtc gactatacag dacccttttt gcctggcttc     480
agagcaatca caaagatga tccattaaac tctgcctttc ctcaggtaaa ttatgacatt      540
attgatcatg ttgtaggaaa tcagcctggt ggcgatatga ctcctacagt agaatggtat      600
gagaaatatc tagaatttca tcgatattgg tctgctgatg agtctgtaat ccataccgat      660
tattcagcat taaggtctgt tgtggttgct gattgggatg aagtgatcaa aatgcctatt      720
aatgagcctg ctgatggact tagaaaaagt caaatccaag aatatgtcga atattatggt      780
ggagcaggcg tacaacatat tgccttaaaa gtcaatgata ttatttcagt aataagcacc      840
ttaagggcta gaggtgtgga attcttagaa gttcctccta atattatga tagcttaaga      900 aaaagacttg cgcattctgc ggtacaaatt gaagaagact taaaagaat tgaagacctt       960 catattttgg ttgactttga cgaccgtggg tatttacttc agattttcac aaaaccagta     1020
gaagacagac ctactctgtt ttatgaaatt attcaaagac ataataacaa tggattcgga     1080
attggaaatt ttaaagccct atttgaatca ttggaacaag agcaagaaag aagaggtaat     1140
ttgatctaa                                                            1149

<210> SEQ ID NO 9
<211> LENGTH: 382
<212> TYPE: PRT
<213> ORGANISM: Blepharisma japonicum

<400> SEQUENCE: 9

Met Thr Tyr Tyr Asp Lys Gln Glu Thr Arg Pro Asp Leu Gly Glu Phe
1               5                   10                  15
```

Tyr Gly Phe His His Val Arg Phe Tyr Val Ser Asn Ser Glu Gln Ala
                    20                  25                  30

Ala Ser Phe Tyr Thr Ser Arg Phe Gly Phe Ser Pro Val Ala Tyr Glu
                35                  40                  45

Gly Leu Glu Thr Gly Asn Gln Lys Phe Cys Thr Asn Val Val Arg Ser
 50                  55                  60

Asn His Val Val Ile Ala Phe Thr Ser Ala Leu Thr Pro Glu Asp Asn
 65                  70                  75                  80

Glu Val Asn Arg His Val Gly Lys His Ser Asp Gly Val Gln Asp Ile
                85                  90                  95

Ala Phe Ser Val Ser Asp Ala Arg Gly Met Tyr Glu Lys Ala Ile Ala
                100                 105                 110

Lys Gly Cys Lys Ser Phe Arg Glu Pro Gln Val Leu Gln Asp Gln Phe
                115                 120                 125

Gly Ser Val Ile Ile Ala Ser Leu Gln Thr Tyr Gly Asp Thr Val His
 130                 135                 140

Thr Leu Val Gln Asn Val Asp Tyr Thr Gly Pro Phe Leu Pro Gly Phe
145                 150                 155                 160

Arg Ala Ile Thr Lys Asp Asp Pro Leu Asn Ser Ala Phe Pro Gln Val
                165                 170                 175

Asn Tyr Asp Ile Ile Asp His Val Val Gly Asn Gln Pro Gly Gly Asp
                180                 185                 190

Met Thr Pro Thr Val Glu Trp Tyr Glu Lys Tyr Leu Glu Phe His Arg
                195                 200                 205

Tyr Trp Ser Ala Asp Glu Ser Val Ile His Thr Asp Tyr Ser Ala Leu
 210                 215                 220

Arg Ser Val Val Val Ala Asp Trp Asp Glu Val Ile Lys Met Pro Ile
225                 230                 235                 240

Asn Glu Pro Ala Asp Gly Leu Arg Lys Ser Gln Ile Gln Glu Tyr Val
                245                 250                 255

Glu Tyr Tyr Gly Gly Ala Gly Val Gln His Ile Ala Leu Lys Val Asn
                260                 265                 270

Asp Ile Ile Ser Val Ile Ser Thr Leu Arg Ala Arg Gly Val Glu Phe
                275                 280                 285

Leu Glu Val Pro Pro Lys Tyr Tyr Asp Ser Leu Arg Lys Arg Leu Ala
 290                 295                 300

His Ser Ala Val Gln Ile Glu Glu Asp Leu Lys Arg Ile Glu Asp Leu
305                 310                 315                 320

His Ile Leu Val Asp Phe Asp Asp Arg Gly Tyr Leu Leu Gln Ile Phe
                325                 330                 335

Thr Lys Pro Val Glu Asp Arg Pro Thr Leu Phe Tyr Glu Ile Ile Gln
                340                 345                 350

Arg His Asn Asn Asn Gly Phe Gly Ile Gly Asn Phe Lys Ala Leu Phe
                355                 360                 365

Glu Ser Leu Glu Gln Glu Gln Glu Arg Arg Gly Asn Leu Ile
 370                 375                 380

<210> SEQ ID NO 10
<211> LENGTH: 1206
<212> TYPE: DNA
<213> ORGANISM: Rhodococcus sp.

<400> SEQUENCE: 10
atgacgatcg agcagactct caccgacaag gaacgcctgg caggtctcga cctcggccag      60

-continued

```
ctcgagcagt tggtcgggct cgtcgagtac gacggcaccc gcgacccgtt cccggtcagc    120
ggctgggatg ccgtcgtctg ggtggtcggc aacgccaccc agaccgccca ctacttccag    180
tccgcgttcg ggatgaccct cgtcgcctac tccggaccca ccaccggcaa ccgcgaccac    240
cacagcttcg tcctcgaatc cggggccgtc cgcttcgtca tcaaaggcgc cgtgaacccg    300
gacagccccc tgatcgacca ccaccgcacc cacggcgacg gcgtcgtcga catcgccctc    360
gccgtccccg acgtcgacaa gtgcatcgcc cacgcccgcg cccagggcgc caccgtcctc    420
gacgaacccc acgacgtgac cgacgaccac ggcaccgtcc gcctcgccgc gatcgccacc    480
tacggcgaca cccgccacac cctcgtcgac cgcagccact acaccggccc ctacctgccc    540
ggctacaccg cccgcacctc cggccacacc aaacgggacg gggcacccaa gcgcctgttc    600
caggccctcg accacgtcgt cggcaacgtc gaactcggca agatggacca ctgggtcgac    660
ttctacaacc gggtcatggg ctttacgaac atggccgagt cgtcggcga ggacatcgcc    720
accgactact ccgcgctgat gagcaaggtc gtctccaacg gcaaccaccg ggtcaagttc    780
cccctcaacg aacccgccct cgccaagaaa cgctcgcaga tcgacgaata cctcgacttc    840
taccgcggcc ccggcgccca gcacctggcc ctggccacca tgacatcct caccgccgtc    900
gaccagctga ccgccgaggg cgtcgagttc ctggccaccc ccgactccta ctacgaggac    960
cccgaactgc gggcccggat cggcaacgtc cgcgccccca tcgccgaact gcagaaacgc   1020
ggcatcctcg tcgaccgcga cgaagacggc tacctgctgc agatcttcac caaacccctc   1080
gtcgaccggc ccaccgtgtt cttcgaactc atcgaacgcc acggctccct cggcttcggc   1140
atcggcaact tcaagccct cttcgaggcc atcgaacgcg aacaagccgc ccgcggaaac   1200
ttctga                                                             1206
```

<210> SEQ ID NO 11
<211> LENGTH: 401
<212> TYPE: PRT
<213> ORGANISM: Rhodococcus sp.

<400> SEQUENCE: 11

```
Met Thr Ile Glu Gln Thr Leu Thr Asp Lys Glu Arg Leu Ala Gly Leu
1               5                   10                  15

Asp Leu Gly Gln Leu Glu Gln Leu Val Gly Leu Val Glu Tyr Asp Gly
            20                  25                  30

Thr Arg Asp Pro Phe Pro Val Ser Gly Trp Asp Ala Val Val Trp Val
        35                  40                  45

Val Gly Asn Ala Thr Gln Thr Ala His Tyr Phe Gln Ser Ala Phe Gly
    50                  55                  60

Met Thr Leu Val Ala Tyr Ser Gly Pro Thr Thr Gly Asn Arg Asp His
65                  70                  75                  80

His Ser Phe Val Leu Glu Ser Gly Ala Val Arg Phe Val Ile Lys Gly
                85                  90                  95

Ala Val Asn Pro Asp Ser Pro Leu Ile Asp His His Arg Thr His Gly
            100                 105                 110

Asp Gly Val Val Asp Ile Ala Leu Ala Val Pro Asp Val Asp Lys Cys
        115                 120                 125

Ile Ala His Ala Arg Ala Gln Gly Ala Thr Val Leu Asp Glu Pro His
    130                 135                 140

Asp Val Thr Asp Asp His Gly Thr Val Arg Leu Ala Ala Ile Ala Thr
145                 150                 155                 160

Tyr Gly Asp Thr Arg His Thr Leu Val Asp Arg Ser His Tyr Thr Gly
```

```
                165                 170                 175
Pro Tyr Leu Pro Gly Tyr Thr Ala Arg Thr Ser Gly His Thr Lys Arg
            180                 185                 190

Asp Gly Ala Pro Lys Arg Leu Phe Gln Ala Leu Asp His Val Val Gly
        195                 200                 205

Asn Val Glu Leu Gly Lys Met Asp His Trp Val Asp Phe Tyr Asn Arg
    210                 215                 220

Val Met Gly Phe Thr Asn Met Ala Glu Phe Val Gly Glu Asp Ile Ala
225                 230                 235                 240

Thr Asp Tyr Ser Ala Leu Met Ser Lys Val Val Ser Asn Gly Asn His
                245                 250                 255

Arg Val Lys Phe Pro Leu Asn Glu Pro Ala Leu Ala Lys Lys Arg Ser
            260                 265                 270

Gln Ile Asp Glu Tyr Leu Asp Phe Tyr Arg Gly Pro Gly Ala Gln His
        275                 280                 285

Leu Ala Leu Ala Thr Asn Asp Ile Leu Thr Ala Val Asp Gln Leu Thr
    290                 295                 300

Ala Glu Gly Val Glu Phe Leu Ala Thr Pro Asp Ser Tyr Tyr Glu Asp
305                 310                 315                 320

Pro Glu Leu Arg Ala Arg Ile Gly Asn Val Arg Ala Pro Ile Ala Glu
                325                 330                 335

Leu Gln Lys Arg Gly Ile Leu Val Asp Arg Asp Glu Asp Gly Tyr Leu
            340                 345                 350

Leu Gln Ile Phe Thr Lys Pro Leu Val Asp Arg Pro Thr Val Phe Phe
        355                 360                 365

Glu Leu Ile Glu Arg His Gly Ser Leu Gly Phe Gly Ile Gly Asn Phe
    370                 375                 380

Lys Ala Leu Phe Glu Ala Ile Glu Arg Glu Gln Ala Ala Arg Gly Asn
385                 390                 395                 400

Phe

<210> SEQ ID NO 12
<211> LENGTH: 1209
<212> TYPE: DNA
<213> ORGANISM: Rhodococcus sp.

<400> SEQUENCE: 12
atgactaccg ccgacattcg cctgacgccc cgcgaggtgg ccgcacatct ggagaccgac      60
gagctccggc agttggtcgg gctcgtcgaa cacgacgacg cgtcggatcc gtttcccgtg     120
gtcgcgatgg atgccgtggt gttcgtgtgc ggcaacgcga cgcagagcac gcagtacttc     180
gtctccacgt ggggcatgac cctcgtcgcc tacgccgggc cggagaccgg tcagcgctcg     240
cacaagtcct tcgtcctcga gtcggggtcg gcacggttcg tgctgcacgg cgccgtcgat     300
ccgaagagcc cgctcgcgga ccatcaccgg gcgcacggcg acggcgtggt ggacctggcg     360
atggaagttc tcgacgtcga ccgctgcatc gcgcatgcac gctcgcaggg ggccaccatt     420
ctcgaggagc cgcgcgacgt cacggatcag ttcggcaccg tgcggctcgc ggcgatcgcc     480
acgtacggca gcacccggca caccatcgtc gaccgaagcc gatacgacgg ccctacctc     540 cccggattcg tcgcgcgctc cagcggtttc gcggcgcgac cgggtaaacc ccgcgattg     600 ttccaggcgc tcgaccacgc cgtcggcaac gtcgagatgg gccggatgga tcactgggtc     660
cggttctaca accgcgtcat gggcttcacg aacatggccg aattcgtcgg cgacgacatc     720
gccacggagt actcggcgct gatgtcgaag gtcgtggcga acggcaatca ccgggtgaag     780
```

```
ttcccgctca acgaacccgc ggtgggaaag aagaagtcgc agatcgacga atatctcgag    840
ttctacggtg agccgggctg ccagcatctg gccctcgcga ccggagacat cctcgcgacg    900
gtggacgcgt tgcgggccga gggtgtcgaa ttcctgaaca cacccgacgc gtactacgag    960
gacccacagc tgcgcgcccg gatcggcagg gtgcgggtgc cggtggagga actgcagaag   1020
cgcggaatcc tcgtcgaccg cgacgaggac ggatacctcc tgcagatctt caccaaaccg   1080
ctcggcgacc ggccgaccgt gttcttcgag gtgatcgaac ggcacggttc gctcgggttc   1140
ggggcgggta acttccaggc cctgttcgaa tccatcgagc gtgagcaggc ggcgcgcggc   1200
aatctgtga                                                           1209
```

<210> SEQ ID NO 13
<211> LENGTH: 402
<212> TYPE: PRT
<213> ORGANISM: Rhodococcus sp.

<400> SEQUENCE: 13

```
Met Thr Thr Ala Asp Ile Arg Leu Thr Pro Arg Glu Val Ala Ala His
  1               5                  10                  15

Leu Glu Thr Asp Glu Leu Arg Gln Leu Val Gly Leu Val Glu His Asp
             20                  25                  30

Asp Ala Ser Asp Pro Phe Pro Val Val Ala Met Asp Ala Val Val Phe
         35                  40                  45

Val Cys Gly Asn Ala Thr Gln Ser Thr Gln Tyr Phe Val Ser Thr Trp
     50                  55                  60

Gly Met Thr Leu Val Ala Tyr Ala Gly Pro Glu Thr Gly Gln Arg Ser
 65                  70                  75                  80

His Lys Ser Phe Val Leu Glu Ser Gly Ser Ala Arg Phe Val Leu His
                 85                  90                  95

Gly Ala Val Asp Pro Lys Ser Pro Leu Ala Asp His His Arg Ala His
            100                 105                 110

Gly Asp Gly Val Val Asp Leu Ala Met Glu Val Leu Asp Val Asp Arg
        115                 120                 125

Cys Ile Ala His Ala Arg Ser Gln Gly Ala Thr Ile Leu Glu Glu Pro
    130                 135                 140

Arg Asp Val Thr Asp Gln Phe Gly Thr Val Arg Leu Ala Ala Ile Ala
145                 150                 155                 160

Thr Tyr Gly Ser Thr Arg His Thr Ile Val Asp Arg Ser Arg Tyr Asp
                165                 170                 175

Gly Pro Tyr Leu Pro Gly Phe Val Ala Arg Ser Ser Gly Phe Ala Ala
            180                 185                 190

Arg Pro Gly Lys Pro Pro Arg Leu Phe Gln Ala Leu Asp His Ala Val
        195                 200                 205

Gly Asn Val Glu Met Gly Arg Met Asp His Trp Val Arg Phe Tyr Asn
    210                 215                 220

Arg Val Met Gly Phe Thr Asn Met Ala Glu Phe Val Gly Asp Asp Ile
225                 230                 235                 240

Ala Thr Glu Tyr Ser Ala Leu Met Ser Lys Val Val Ala Asn Gly Asn
                245                 250                 255

His Arg Val Lys Phe Pro Leu Asn Glu Pro Ala Val Gly Lys Lys Lys
            260                 265                 270

Ser Gln Ile Asp Glu Tyr Leu Glu Phe Tyr Gly Glu Pro Gly Cys Gln
        275                 280                 285
```

His Leu Ala Leu Ala Thr Gly Asp Ile Leu Ala Thr Val Asp Ala Leu
    290                 295                 300

Arg Ala Glu Gly Val Glu Phe Leu Asn Thr Pro Asp Ala Tyr Tyr Glu
305                 310                 315                 320

Asp Pro Gln Leu Arg Ala Arg Ile Gly Arg Val Arg Val Pro Val Glu
                325                 330                 335

Glu Leu Gln Lys Arg Gly Ile Leu Val Asp Arg Asp Glu Asp Gly Tyr
            340                 345                 350

Leu Leu Gln Ile Phe Thr Lys Pro Leu Gly Asp Arg Pro Thr Val Phe
        355                 360                 365

Phe Glu Val Ile Glu Arg His Gly Ser Leu Gly Phe Gly Ala Gly Asn
    370                 375                 380

Phe Gln Ala Leu Phe Glu Ser Ile Glu Arg Glu Gln Ala Ala Arg Gly
385                 390                 395                 400

Asn Leu

<210> SEQ ID NO 14
<211> LENGTH: 1107
<212> TYPE: DNA
<213> ORGANISM: Picrophilus torridus

<400> SEQUENCE: 14
atgtatggca aaatttaat ctcagaacta agggaaaagg agatctttaa acgattacat      60
cacgtggaat tttacgttag cagtgccaaa acatggtcat atttcatgaa cagggggtctt    120 ggatttaaaa cagtggcata tgccggtcca gaaaccggga taagggacaa gatatcctat    180
gttatgtccc agggcactgc aaggatatct tttacatcat caatgaatga tgatagctat    240
atatcgaatc atgttaaaaa acacggggat ggcgtaaagg atatagcact tgaggtcgat    300
gatctggacg aggcaaaaag cctgatagaa aagtatggaa caaaggtttc aaaaataaat    360
gaaataaagg atgaaatgg aaagataaga actgcagaga taaaaacgta cggtgaaacc    420
gttcatacat taatagaaac cggggattac aatggcgtat tcatgcccgg ttatgaggaa    480
tctgaaataa attcaaaaaa cactgggata aaaaagatcg atcatatagt tggaaatgtc    540
tatgagggcg agatggatag ctgggttaat ttttacatag aaaaacttgg ctttgagcat    600 ttaataaccct tgatgataa agatataaga actgattaca gcgcattaag atcaaaggtt    660
gtaaaataca atgacgatat cgtatttcca ataaatgagc ctgcaaaggg cttaagaaaa    720
tcacagatag aggaatatct tgactattac aggtctgagg gcgttcagca catagcactg    780
ttaactgatg atataataaa aactgtatcc atgatggagg aaaacggcat agaattttta    840
aaaacaccag gatcatacta tgaatcccta tcatcaagga taggctcaat agacgaggat    900
ttaaatgaaa tagagaaaca taacatactt gtggatcgtg atgagaacgg atacctatta    960
cagatcttca caaagcctgt tactgacagg ccaacgttct tctttgaggt catacagaga   1020
aagggtgcaa ggtcattcgg caacggtaac tttaaggcac tttttgaggc gatagaaagg   1080
gagcaggcaa agagaggaaa cctatga                                        1107

<210> SEQ ID NO 15
<211> LENGTH: 368
<212> TYPE: PRT
<213> ORGANISM: Picrophilus torridus

<400> SEQUENCE: 15

Met Tyr Gly Lys Asn Leu Ile Ser Glu Leu Arg Glu Lys Glu Ile Phe
1               5                   10                  15

```
Lys Arg Leu His His Val Glu Phe Tyr Val Ser Ser Ala Lys Thr Trp
         20                  25                  30

Ser Tyr Phe Met Asn Arg Gly Leu Gly Phe Lys Thr Val Ala Tyr Ala
             35                  40                  45

Gly Pro Glu Thr Gly Ile Arg Asp Lys Ile Ser Tyr Val Met Ser Gln
 50                  55                  60

Gly Thr Ala Arg Ile Ser Phe Thr Ser Ser Met Asn Asp Asp Ser Tyr
 65                  70                  75                  80

Ile Ser Asn His Val Lys Lys His Gly Asp Gly Val Lys Asp Ile Ala
                 85                  90                  95

Leu Glu Val Asp Asp Leu Asp Glu Ala Lys Ser Leu Ile Glu Lys Tyr
            100                 105                 110

Gly Thr Lys Val Ser Lys Ile Asn Glu Ile Lys Asp Gly Asn Gly Lys
            115                 120                 125

Ile Arg Thr Ala Glu Ile Lys Thr Tyr Gly Glu Thr Val His Thr Leu
130                 135                 140

Ile Glu Thr Gly Asp Tyr Asn Gly Val Phe Met Pro Gly Tyr Glu Glu
145                 150                 155                 160

Ser Glu Ile Asn Ser Lys Asn Thr Gly Ile Lys Lys Ile Asp His Ile
                165                 170                 175

Val Gly Asn Val Tyr Glu Gly Glu Met Asp Ser Trp Val Asn Phe Tyr
            180                 185                 190

Ile Glu Lys Leu Gly Phe Glu His Leu Ile Thr Phe Asp Asp Lys Asp
            195                 200                 205

Ile Arg Thr Asp Tyr Ser Ala Leu Arg Ser Lys Val Val Lys Tyr Asn
210                 215                 220

Asp Asp Ile Val Phe Pro Ile Asn Glu Pro Ala Lys Gly Leu Arg Lys
225                 230                 235                 240

Ser Gln Ile Glu Glu Tyr Leu Asp Tyr Tyr Arg Ser Glu Gly Val Gln
                245                 250                 255

His Ile Ala Leu Leu Thr Asp Asp Ile Ile Lys Thr Val Ser Met Met
            260                 265                 270

Glu Glu Asn Gly Ile Glu Phe Leu Lys Thr Pro Gly Ser Tyr Tyr Glu
            275                 280                 285

Ser Leu Ser Ser Arg Ile Gly Ser Ile Asp Glu Asp Leu Asn Glu Ile
290                 295                 300

Glu Lys His Asn Ile Leu Val Asp Arg Asp Glu Asn Gly Tyr Leu Leu
305                 310                 315                 320

Gln Ile Phe Thr Lys Pro Val Thr Asp Arg Pro Thr Phe Phe Glu
                325                 330                 335

Val Ile Gln Arg Lys Gly Ala Arg Ser Phe Gly Asn Gly Asn Phe Lys
            340                 345                 350

Ala Leu Phe Glu Ala Ile Glu Arg Glu Gln Ala Lys Arg Gly Asn Leu
            355                 360                 365

<210> SEQ ID NO 16
<211> LENGTH: 1164
<212> TYPE: DNA
<213> ORGANISM: Kordia algicida

<400> SEQUENCE: 16
atggcagcag aaataaaaaa cttaaaagat ttacaaaata cagaatacgg actcaaaaaa    60
ttatttgacg aagcagaaga ctttcttcca cttttaggaa cagactacgt agaattatac   120
```

-continued

```
gtcgggaacg ccaaacaatc ggcacatttc tacaaaacgg cttttggttt tcaatcagaa    180
gcttacgcag gattggaaac aggattaacc gacagagttt catacgtatt aaaacaagat    240
aaaattcgct tggtcttaac aacaccatta ggaaaaggtg gcgaaatcaa tgagcatatc    300
gatttacacg gcgatggcgt aaaagtagta gcactttggg tagaagatgc tacaaaagcc    360
tttgaagaaa cgaccaaaag aggcgcaaaa ccgtacatgg aaccaacaaa agaagaagat    420
gaaaacggat atgtaattcg ctcaggaatc tatacgtacg gagaaacggt tcatgttttt    480
gtagaacgta aaaactataa cggagtcttt ttaccaggat atcaaagatg ggaatctcac    540
tacaatccgg agccagttgg cttaaaattc atcgatcaca tggtaggaaa tgtaggttgg    600
ggagaaatga agaatggtg tgaattctac gcgaaagtaa tgggatttgc gcaaattatc    660
tcctttacag atgatgatat ttctaccgat tttactgcgt tgatgagtaa agtaatgagt    720
aatggaaatg gtagaatcaa atttccaatc aatgaacccg cagaaggaaa aaagaaatcg    780
caaattgaag aatatctaga cttttacaat ggttcaggag tacaacatat tgcggttgct    840
acagacaata ttattgatac ggtttcgcaa atgcgcgaac gtggagtaga attcttatac    900
gttccagata catattatga tgacttgtta gaacgtgttg gcgacatcga tgaagatgta    960
gaagaactca aaaacacgg aatcttaatt gatcgtgatg aagaaggata cttattgcag   1020
ttatttacca aaaccattgt agacagacca acaatgttct ttgaagtcat tcagcgtaaa   1080
ggcgcacaat catttggagt aggaaacttt aaagctttat ttgaagcgat agaaagagaa   1140
caagctgctc gcggaacatt gtaa                                         1164
```

<210> SEQ ID NO 17
<211> LENGTH: 387
<212> TYPE: PRT
<213> ORGANISM: Kordia algicida

<400> SEQUENCE: 17

```
Met Ala Ala Glu Ile Lys Asn Leu Lys Asp Leu Gln Asn Thr Glu Tyr
1               5                   10                  15

Gly Leu Lys Lys Leu Phe Asp Glu Ala Glu Asp Phe Leu Pro Leu Leu
                20                  25                  30

Gly Thr Asp Tyr Val Glu Leu Tyr Val Gly Asn Ala Lys Gln Ser Ala
            35                  40                  45

His Phe Tyr Lys Thr Ala Phe Gly Phe Gln Ser Glu Ala Tyr Ala Gly
        50                  55                  60

Leu Glu Thr Gly Leu Thr Asp Arg Val Ser Tyr Val Leu Lys Gln Asp
65                  70                  75                  80

Lys Ile Arg Leu Val Leu Thr Thr Pro Leu Gly Lys Gly Gly Glu Ile
                85                  90                  95

Asn Glu His Ile Asp Leu His Gly Asp Gly Val Lys Val Val Ala Leu
            100                 105                 110

Trp Val Glu Asp Ala Thr Lys Ala Phe Glu Glu Thr Thr Lys Arg Gly
        115                 120                 125

Ala Lys Pro Tyr Met Glu Pro Thr Lys Glu Glu Asp Glu Asn Gly Tyr
    130                 135                 140

Val Ile Arg Ser Gly Ile Tyr Thr Tyr Gly Glu Thr Val His Val Phe
145                 150                 155                 160

Val Glu Arg Lys Asn Tyr Asn Gly Val Phe Leu Pro Gly Tyr Gln Arg
                165                 170                 175

Trp Glu Ser His Tyr Asn Pro Glu Pro Val Gly Leu Lys Phe Ile Asp
            180                 185                 190
```

```
      His Met Val Gly Asn Val Gly Trp Gly Glu Met Lys Glu Trp Cys Glu
              195                 200                 205

Phe Tyr Ala Lys Val Met Gly Phe Ala Gln Ile Ile Ser Phe Thr Asp
          210                 215                 220

Asp Asp Ile Ser Thr Asp Phe Thr Ala Leu Met Ser Lys Val Met Ser
      225                 230                 235                 240

Asn Gly Asn Gly Arg Ile Lys Phe Pro Ile Asn Glu Pro Ala Glu Gly
                      245                 250                 255

Lys Lys Lys Ser Gln Ile Glu Glu Tyr Leu Asp Phe Tyr Asn Gly Ser
                  260                 265                 270

Gly Val Gln His Ile Ala Val Ala Thr Asp Asn Ile Ile Asp Thr Val
                  275                 280                 285

Ser Gln Met Arg Glu Arg Gly Val Glu Phe Leu Tyr Val Pro Asp Thr
              290                 295                 300

Tyr Tyr Asp Asp Leu Leu Glu Arg Val Gly Asp Ile Asp Glu Asp Val
      305                 310                 315                 320

Glu Glu Leu Lys Lys His Gly Ile Leu Ile Asp Arg Asp Glu Glu Gly
                      325                 330                 335

Tyr Leu Leu Gln Leu Phe Thr Lys Thr Ile Val Asp Arg Pro Thr Met
                  340                 345                 350

Phe Phe Glu Val Ile Gln Arg Lys Gly Ala Gln Ser Phe Gly Val Gly
              355                 360                 365

Asn Phe Lys Ala Leu Phe Glu Ala Ile Glu Arg Glu Gln Ala Ala Arg
          370                 375                 380

Gly Thr Leu
      385

<210> SEQ ID NO 18
<211> LENGTH: 1056
<212> TYPE: DNA
<213> ORGANISM: Artificial Sequence
<220> FEATURE:
<223> OTHER INFORMATION: Nucleic acid sequence encoding Synechococcus
      sp. HPPD optimized for the expression in soybean and cotton

<400> SEQUENCE: 18
atggctaacc catccattag gatcgttcag ggaatccatc accttcactt ctacctttgg     60
gatcttccaa ggtggagaga gcatttctgt agagtttggg gattcagagt tgcttctgat    120
gctggaaaca ctcttgaact tgagcaagga tctcttaggc ttaggctttc tcaaccagct    180
agagctggtg atgaagttga taggcatctt caaagacatg gaccaggtgt tgttgatgtt    240
gctcttgctg ttggagaaca agaacttcca gctcttgctg aacttcttag aggaagggt    300 gctcaacttg cttggattcc agctgctgct gtctctttgcc ttcatactcc atacggaatt    360
aggcactccc ttattccagg accacttgat gctgctccag ctgaggctgg acttttttct    420
cattgggatc acgttgttct taatgtggag cagggatctc ttcaagctgc tgctgattgg    480
tatggaagag ttcttggatg gcgtagactt taccgttact ccatcggaac tgctacttca    540
ggacttgagt ctgttgttgt tggagatcca gaggctggca ttcaatgggc tatcaacgaa    600
cctacttgcg ctgcttctca gattcaagag ttccttcatg ctcatggtgg accaggtatt    660
caacatgctg ctctccactc ttcagatatt gtggcttctc ttagaaggct taggcaaggt    720
ggagttgatt ccttcaagt ggctccacag tactatactt ctcttgagag agagcttgga    780
cttgctctta gatctgctct tggacaggct atttcttggc aggatcttgt tgagcagcag    840
```

```
attcttcttg atgctactct tccagcttct gatggacaag ataggccact tttgctccaa    900
actttcactc aaccactttt cggaaggcca acattcttct tcgaagtgat tcaaagactt    960
ggaggtgcta ctggatttgg agaggctaat ttccaagctc ttttcgaggc tcttgaaagg   1020
caacaaaggc aaaggcatca agctcttact ccatga                             1056
```

<210> SEQ ID NO 19
<211> LENGTH: 1152
<212> TYPE: DNA
<213> ORGANISM: Artificial Sequence
<220> FEATURE:
<223> OTHER INFORMATION: Nucleic acid sequence encoding Blepharisma
      japonicum HPPD optimized for the expression in soybean and cotton

<400> SEQUENCE: 19

```
atggctactt actacgataa gcaagagact agaccagatc ttggagagtt ctacggattc     60
caccatgtta ggttctacgt gtctaattct gagcaagctg cttctttcta cacttcccgt    120
ttcggatttt ctccagttgc ttacgaagga cttgagactg aaatcagaa gttctgcact    180 aacgttgtta ggtctaacca cgtggtgatt gcttttactt ctgctctcac tccagaggat    240
aatgaggtta acaggcatgt tggaaagcac tctgatggtg ttcaggatat tgctttctct    300
gtgtctgatg ctagaggaat gtacgagaag gctattgcta agggatgcaa gtcttccaga    360
gagccacaag ttcttcaaga tcagttcgga tcagtgatta ttgcttccct tcagacttac    420
ggtgatactg ttcacactct cgttcagaac gttgattaca ctggaccatt ccttccaggt    480
ttcagggcta tcactaagga tgatccactt aactctgctt ccccacaggt gaactacgat    540
atcattgatc acgttgtggg aaatcagcca ggtggagata tgactccaac tgttgagtgg    600
tacgagaagt accttgagtt tcacaggtat tggagtgctg atgagtctgt gatccacact    660
gattactctg ctcttagatc tgttgttgtg gctgattggg atgaggttat caagatgcct    720
attaacgaac cagctgatgg acttaggaag tcccagattc aagagtacgt tgagtattat    780
ggtggagctg tgttcaaca cattgctctc aaggtgaacg atatcatttc cgtgatttcc    840
actcttagag ctagaggagt tgagtttctt gaagtcccac caaagtacta cgattctctc    900
agaaagaggc ttgctcattc tgctgttcag atcgaagagg atcttaaacg tattgaggac    960
cttcacatcc tcgtggattt tgatgatagg ggatacctc tccagatttt cactaagcca   1020
gttgaggata ggccaacttt gttctacgag atcatccaaa ggcataacaa caacggattc   1080
ggaatcggaa atttcaaggc tcttttcgag tctcttgagc aagaacaaga gagaaggggga   1140 aacctcatct ga                                                      1152
```

<210> SEQ ID NO 20
<211> LENGTH: 1209
<212> TYPE: DNA
<213> ORGANISM: Artificial Sequence
<220> FEATURE:
<223> OTHER INFORMATION: Nucleic acid sequence encoding Rhodococcus sp.
      (strain RHA1), isolate ro03041 HPPD optimized for the expression
      in soybean and cotton

<400> SEQUENCE: 20

```
atggctacta ttgagcagac tctcactgat aaggaaaggc ttgctggact tgatcttgga     60
caacttgagc agcttgttgg acttgttgag tacgatggaa ctagggaccc atttccagtt    120
tctggatggg atgctgttgt ttgggttgtg ggaaatgcta ctcaaactgc tcactacttc    180
caatctgctt tcggaatgac tcttgtggct tactctggac caactactgg aaatagggat    240
```

```
caccactctt tcgttcttga atctggtgct gtgagattcg ttattaaggg tgctgtgaac      300
ccagattctc cacttattga tcaccatagg actcatggtg atggtgttgt ggatattgct      360
cttgctgttc cagatgtgga taagtgcatt gctcatgcta gggctcaagg tgctactgtt      420
cttgatgagc acacgatgt tactgatgat cacggaactg ttaggcttgc tgctattgct       480
acttacggtg atacaaggca cactcttgtt gataggtcac actacactgg accatatctt      540
ccaggataca ctgctagaac ttccggacac actaagaggg atggtgctcc aaagagactt      600
ttccaggctc ttgatcacgt tgttggaaac gttgagcttg aaagatgga tcactgggtg       660 gacttctaca ataggtgat gggattcact aatatgctg agtttgtggg agaagatatc        720
gctactgatt actctgctct catgtctaag gttgtgtcta atggaaacca cagggtgaag      780
ttcccactta atgaaccagc tctcgctaaa aaaggtcac agatcgatga gtacctcgat       840
ttttatcgtg gaccaggtgc tcaacatctt gctctcgcta ctaacgatat tctcactgct      900
gtggatcaac ttactgctga gggtgttgag tttcttgcta ctccagattc ctattacgag      960
gacccagaac ttagagctag gatcggaaat gttagggctc caatcgctga acttcagaag     1020 agggaatac tcgttgatag agatgaggat ggatacctta tccagatctt cactaagcca      1080
ttggttgata ggccaactgt tttcttcgag cttattgaga ggcatggatc tcttggattc     1140
ggaatcggaa acttcaaggc tcttttcgag gctattgaga gagaacaagc tgctagggga     1200
aatttctga                                                            1209
```

<210> SEQ ID NO 21
<211> LENGTH: 1212
<212> TYPE: DNA
<213> ORGANISM: Artificial Sequence
<220> FEATURE:
<223> OTHER INFORMATION: Nucleotide sequence encoding Rhodococcus sp.
     (strain RHA1), isolate ro02040 HPPD optimized optimized for the
     expression in soybean and cotton

<400> SEQUENCE: 21

```
atggctacta ctgctgatat taggcttact ccaagggaag ttgctgctca tcttgagact       60
gatgagctta ggcaacttgt tggacttgtt gagcacgatg atgcttcaga tccattccca      120
gttgttgcta tggatgctgt tgttttttgtt tgcggaaacg ctactcaatc tactcagtac     180
ttcgtgtcta cttggggaat gactcttgtt gcttatgctg accagaaac tggacagaga      240 tctcacaagt ctttcgtgct tgaatctgga tctgctagat tcgttcttca cggtgctgtt      300
gatccaaagt ctccacttgc tgatcatcat agggctcatg gtgatggtgt tgtggatctt     360
gctatggaag tgcttgatgt ggatagatgc attgctcatg ctagatctca gggtgctact     420
attcttgaag aacctcgtga tgtgactgat cagtttggaa ctgttaggct tgctgctatt     480
gctacttacg gctccactag gcacactatt gtggataggt ccagatatga tggaccatac     540
cttccaggat tgttgctag gtcatctgga tttgctgcta gaccaggaaa gccaccaaga      600
cttttccaag ctcttgatca cgctgttgga atgttgaaaa tgggaaggat ggatcattgg     660
gtgaggttct acaataggt gatgggattc actaatatgg ctgagttcgt gggtgatgat     720
attgctactg agtactctgc tcttatgtct aaggttgtgg ctaatggaaa tcacagggtg     780
aagttcccac ttaatgaacc agctgtggga agaagaagt cccagatcga cgagtacctt      840
gagttttacg tgaaccagg atgtcaacat cttgctctcg ctactggtga tattcttgct     900
actgtggatg ctcttagagc tgaaggtgtt gagttcctca atactccaga tgcttactac     960
gaggacccac aacttagagc taggattgga agagttaggg ttccagttga ggaacttcag    1020
```

```
aagaggggaa tactcgttga tagagatgag gatggatacc ttctccagat cttcactaag   1080
ccacttggag ataggccaac tgttttcttc gaagtgattg agaggcatgg atctcttgga   1140
tttggagcag gaaacttcca ggcactttc gagtctattg agagagaaca agctgctagg   1200
ggaaatcttt ga                                                      1212
```

<210> SEQ ID NO 22
<211> LENGTH: 1110
<212> TYPE: DNA
<213> ORGANISM: Artificial Sequence
<220> FEATURE:
<223> OTHER INFORMATION: Nucleic acid sequence encoding Picrophilus
      torridus HPPD optimized for the expression in soybean and cotton

<400> SEQUENCE: 22

```
atggcttacg gaaagaacct tatttctgag cttagagaga aagagatctt caagaggctt     60
catcacgttg agttctacgt ttcttccgct aagacttggt cctacttcat gaataggga    120 ctcggattca agactgttgc ttatgctgga ccagaaactg gaatcaggga taagatctcc    180
tacgttatgt ctcaaggtac tgctaggatt tctttcactt cctccatgaa cgatgattcc    240
tacatttcca accacgttaa gaaacacggt gatggtgtta aggatatcgc tctcgaagtg    300
gatgatcttg atgaggctaa gtctctcatt gagaagtacg gaactaaggt gtccaagatc    360
aacgagatca aggatggaaa cggaaagatt aggactgctg agatcaagac ttacggtgaa    420
actgtgcaca ctcttatcga gactggtgat acaacggtg ttttcatgcc aggatacgaa    480
gagtctgaga tcaactccaa gaacactggt atcaaaaaaa tcgatcacat tgtgggaaat    540
gtttacgagg gtgaaatgga ttcttgggtg aacttctaca ttgagaagtt gggattcgag    600
caccttatca ctttcgatga taaggatatc aggactgatt actctgctct taggtctaag    660
gtggtgaagt acaacgatga tatcgtgttc cctattaacg aaccagctaa gggacttagg    720
aagtcccaaa tcgaagagta cctcgattat taccgttctg agggtgttca acacattgct    780
ttgctcacag acgatatcat caagactgtg tccatgatgg aagagaacgg aattgagttc    840
cttaagactc caggatctta ctacgagtct ttgtcctcta ggattggatc tatcgatgag    900
gatctcaacg aaatcgagaa gcacaacatt cttgtggata gggatgagaa cggatacctt    960
ctccagattt tcactaagcc agtgactgat aggccaacat tcttcttcga agtgatccaa   1020
agaaagggtg ctagatcttt cggaaacgga aacttcaagg ctcttttcga ggctattgag   1080
agagaacaag ctaagagggg aaacctttga                                   1110
```

<210> SEQ ID NO 23
<211> LENGTH: 1167
<212> TYPE: DNA
<213> ORGANISM: Artificial Sequence
<220> FEATURE:
<223> OTHER INFORMATION: Nucleic acid sequence encoding Kordia algicida
      HPPD optimized for the expression in soybean and cotton

<400> SEQUENCE: 23

```
atggctgctg ctgagattaa gaacctcaag gatctccaga atactgagta cggactcaag    60 aaacttttg atgaggctga ggatttcctt ccacttctcg gaactgatta cgttgagctt   120
tatgtgggaa acgcaaagca atctgctcac ttctacaaga ctgctttcgg atttcaatct   180
gaggcttacg ctggacttga aactggactt actgataggg tttcctacgt gcttaagcag   240
gataagatta ggcttgtgct cactactcca cttggaaagg gtggagagat taacgagcac   300
```

```
attgatcttc atggtgatgg tgttaaggtt gtggctcttt gggttgaaga tgctactaag    360
gctttcgaag agactactaa gagaggtgca aagccttata tggaacctac aaaagaagag    420
gacgagaacg gatacgtgat tagatccgga atctacactt acggtgagac tgttcacgtt    480
ttcgtggaga ggaagaacta caacggagtc tttcttcctg gataccaacg atgggagtct    540
cattacaatc cagagccagt gggacttaag ttcatcgatc acatggtggg taatgttgga    600
tggggagaga tgaaggaatg gtgcgagttt tacgctaagg ttatgggatt cgctcagatc    660
atttccttca ctgatgatga tatctccact gatttcactg ctcttatgtc caaggtgatg    720
tctaatggaa acggaaggat caagttccct attaacgaac cagctgaggg aaagaagaag    780
tcccagatcg aagagtacct cgatttctac aacggatctg gtgttcagca tattgctgtg    840
gcaactgata acatcatcga tactgtgtct caaatgagag aaaggggagt ggagtttctt    900
tacgtcccag atacttacta cgatgatctc cttgagagag tgggagatat tgacgaggat    960
gtggaggaac ttaagaagca cggaatcctc attgatagag atgaagaggg ataccttctc   1020
cagcttttca ctaagactat cgtggatagg ccaactatgt tcttcgaagt gatccaaaga   1080
aagggtgctc aatctttcgg agtgggaaac ttcaaggctc ttttcgaggc tattgagaga   1140
gaacaagctg ctagaggaac tctttga                                       1167
```